US011193163B2

(12) United States Patent
Daugharthy et al.

(10) Patent No.: US 11,193,163 B2
(45) Date of Patent: Dec. 7, 2021

(54) METHODS AND SYSTEMS FOR SAMPLE PROCESSING OR ANALYSIS

(71) Applicant: ReadCoor, Inc., Cambridge, MA (US)

(72) Inventors: Evan Daugharthy, Cambridge, MA (US); Richard Terry, Carlisle, MA (US)

(73) Assignee: ReadCoor, LLC, Pleasanton, CA (US)

( * ) Notice: Subject to any disclaimer, the term of this patent is extended or adjusted under 35 U.S.C. 154(b) by 0 days.

(21) Appl. No.: 16/675,756

(22) Filed: Nov. 6, 2019

(65) Prior Publication Data

US 2020/0071751 A1   Mar. 5, 2020

Related U.S. Application Data

(63) Continuation of application No. PCT/US2019/043773, filed on Jul. 26, 2019.

(60) Provisional application No. 62/711,994, filed on Jul. 30, 2018.

(51) Int. Cl.
*C12Q 1/6834* (2018.01)
*C12Q 1/6806* (2018.01)
*C12Q 1/6874* (2018.01)

(52) U.S. Cl.
CPC ......... *C12Q 1/6834* (2013.01); *C12Q 1/6806* (2013.01); *C12Q 1/6874* (2013.01)

(58) Field of Classification Search
CPC .................................. C12Q 1/68; C07H 21/00
See application file for complete search history.

(56) References Cited

U.S. PATENT DOCUMENTS

| | | |
|---|---|---|
| 4,123,610 A | 10/1978 | Summerton et al. |
| 4,683,195 A | 7/1987 | Mullis et al. |
| 4,683,202 A | 7/1987 | Mullis |
| 4,800,159 A | 1/1989 | Mullis et al. |
| 4,844,617 A | 7/1989 | Kelderman et al. |
| 4,883,750 A | 11/1989 | Whiteley et al. |
| 4,886,741 A | 12/1989 | Schwartz |
| 4,965,188 A | 10/1990 | Mullis et al. |
| 4,981,985 A | 1/1991 | Kaplan et al. |
| 5,116,742 A * | 5/1992 | Cech ...................... C12N 15/10 435/199 |
| 5,151,189 A | 9/1992 | Hu et al. |
| 5,174,670 A | 12/1992 | Takagi et al. |
| 5,210,015 A | 5/1993 | Gelfand et al. |
| 5,244,797 A * | 9/1993 | Kotewicz ............. C12N 9/1276 435/194 |
| 5,399,491 A | 3/1995 | Kacian et al. |
| 5,563,056 A * | 10/1996 | Swan ...................... A61L 29/16 435/180 |
| 5,594,235 A | 1/1997 | Lee |
| 5,684,149 A | 11/1997 | Morrow |
| 5,688,670 A * | 11/1997 | Szostak ................ C12N 15/113 435/6.1 |
| 5,695,940 A | 12/1997 | Drmanac et al. |
| 5,795,236 A | 8/1998 | Alberts et al. |
| 5,830,708 A | 11/1998 | Naughton |
| 5,834,758 A | 11/1998 | Trulson et al. |
| 5,866,337 A | 2/1999 | Schon |
| 5,871,921 A | 2/1999 | Landegren et al. |
| 5,942,391 A | 8/1999 | Zhang et al. |
| 6,063,612 A * | 5/2000 | Jayasena ................ A61K 31/70 435/235.1 |
| 6,083,726 A | 7/2000 | Mills, Jr. et al. |
| 6,174,670 B1 | 1/2001 | Wittwer et al. |
| 6,183,960 B1 | 2/2001 | Lizardi |
| 6,183,967 B1 | 2/2001 | Jayasena et al. |
| 6,221,603 B1 * | 4/2001 | Mahtani ............... C12Q 1/6816 435/6.12 |
| 6,235,472 B1 | 5/2001 | Landegren et al. |
| 6,287,778 B1 | 9/2001 | Huang et al. |
| 6,287,825 B1 | 9/2001 | Weissman et al. |
| 6,306,597 B1 | 10/2001 | Macevicz |
| 6,344,239 B1 | 2/2002 | Asai et al. |
| 6,432,360 B1 | 8/2002 | Church |
| 6,485,944 B1 | 11/2002 | Church et al. |
| 6,506,594 B1 | 1/2003 | Barany et al. |
| 6,511,803 B1 | 1/2003 | Church et al. |
| 6,534,266 B1 | 3/2003 | Singer |
| 6,586,176 B1 | 7/2003 | Trnovsky et al. |
| 6,632,655 B1 | 10/2003 | Mehta et al. |
| 6,709,816 B1 | 3/2004 | Huang et al. |
| 6,858,412 B2 * | 2/2005 | Willis ................... C12Q 1/6827 435/6.12 |
| 7,255,994 B2 | 8/2007 | Lao |
| 7,323,305 B2 | 1/2008 | Leamon et al. |
| 7,427,479 B2 | 9/2008 | Karger et al. |
| 7,473,767 B2 | 1/2009 | Dimitrov |
| 7,745,129 B1 | 6/2010 | Schatz |
| 7,906,285 B2 | 3/2011 | Drmanac |
| 8,124,751 B2 | 2/2012 | Pierce et al. |
| 8,268,554 B2 | 9/2012 | Schallmeiner |
| 8,329,404 B2 | 12/2012 | McKernan et al. |

(Continued)

FOREIGN PATENT DOCUMENTS

| | | |
|---|---|---|
| CN | 101636649 A | 1/2010 |
| EP | 2878671 A1 | 6/2015 |

(Continued)

OTHER PUBLICATIONS

Bock, RM. Alkaline Hydrolysis of RNA. Methods in Enzymology 12 : 224-228 (Year: 1967).*

(Continued)

*Primary Examiner* — Ethan C Whisenant

(74) *Attorney, Agent, or Firm* — Wilson Sonsini Goodrich & Rosati

(57) ABSTRACT

The present disclosure provides methods and systems for detecting nucleic acid sequences in a biological sample having a three-dimensional matrix. The present disclosure also provides methods and systems for processing a biological sample for use in nucleic acid sequence detection.

29 Claims, 6 Drawing Sheets

(56) References Cited

U.S. PATENT DOCUMENTS

| | | | |
|---|---|---|---|
| 8,460,865 B2 | 6/2013 | Chee et al. | |
| 8,501,459 B2 | 8/2013 | Chen et al. | |
| 8,551,710 B2 | 10/2013 | Bernitz et al. | |
| 9,201,063 B2 | 12/2015 | Sood et al. | |
| 9,217,151 B2 | 12/2015 | Yin et al. | |
| 9,914,967 B2 | 3/2018 | Church et al. | |
| 10,036,055 B2 | 7/2018 | Church et al. | |
| 10,138,509 B2* | 11/2018 | Church | C12Q 1/6869 |
| 10,179,932 B2 | 1/2019 | Church et al. | |
| 10,227,639 B2 | 3/2019 | Levner et al. | |
| 10,266,888 B2* | 4/2019 | Daugharthy | C12Q 1/68 |
| 10,267,808 B2 | 4/2019 | Cai | |
| 10,494,662 B2 | 12/2019 | Church et al. | |
| 10,494,664 B2* | 12/2019 | Doudna | C12Q 1/6823 |
| 10,494,667 B2 | 12/2019 | Chee | |
| 10,501,791 B2 | 12/2019 | Church et al. | |
| 10,538,795 B2* | 1/2020 | Seitz | C12Q 1/6844 |
| 10,545,075 B2 | 1/2020 | Deisseroth et al. | |
| 2002/0015952 A1 | 2/2002 | Anderson et al. | |
| 2002/0029979 A1 | 3/2002 | Freund et al. | |
| 2002/0049176 A1* | 4/2002 | Anderson | C07K 14/4705 |
| | | | 514/44 R |
| 2002/0117109 A1 | 8/2002 | Hazelton et al. | |
| 2002/0155989 A1 | 10/2002 | Efimov et al. | |
| 2002/0168645 A1 | 11/2002 | Taylor | |
| 2002/0172950 A1 | 11/2002 | Kenny et al. | |
| 2002/0182598 A1 | 12/2002 | Zhang | |
| 2003/0003490 A1 | 1/2003 | Fan et al. | |
| 2003/0018984 A1* | 1/2003 | Coleman | C07K 14/65 |
| | | | 800/4 |
| 2003/0104459 A1 | 6/2003 | Faham et al. | |
| 2003/0148335 A1 | 8/2003 | Shen et al. | |
| 2003/0228611 A1 | 12/2003 | Chruch et al. | |
| 2004/0006035 A1* | 1/2004 | Macejak | A61K 45/06 |
| | | | 514/44 A |
| 2004/0072014 A1 | 4/2004 | Hasz et al. | |
| 2004/0077014 A1 | 4/2004 | Becker | |
| 2004/0081962 A1* | 4/2004 | Chen | C12N 15/1096 |
| | | | 435/6.11 |
| 2004/0086892 A1 | 5/2004 | Crothers et al. | |
| 2004/0101835 A1 | 5/2004 | Willis et al. | |
| 2004/0126770 A1 | 7/2004 | Kumar et al. | |
| 2004/0152072 A1* | 8/2004 | Gerard | C12N 15/1096 |
| | | | 435/5 |
| 2004/0197800 A1 | 10/2004 | Borns | |
| 2004/0248144 A1 | 12/2004 | Mir | |
| 2004/0259190 A1 | 12/2004 | Naughton | |
| 2004/0259226 A1 | 12/2004 | Robey et al. | |
| 2005/0032694 A1* | 2/2005 | Sonderegger | C12N 9/6424 |
| | | | 435/79 |
| 2005/0037393 A1 | 2/2005 | Gunderson et al. | |
| 2005/0064435 A1 | 3/2005 | Su et al. | |
| 2005/0106629 A1 | 5/2005 | McGrath et al. | |
| 2005/0147981 A1 | 7/2005 | Yamakawa et al. | |
| 2005/0164207 A1 | 7/2005 | Shapero | |
| 2005/0176035 A1 | 8/2005 | Crothers | |
| 2005/0191687 A1 | 9/2005 | Wang et al. | |
| 2005/0221304 A1* | 10/2005 | Xiang | C12Q 1/6853 |
| | | | 435/6.12 |
| 2005/0233318 A1 | 10/2005 | Chee et al. | |
| 2006/0019304 A1 | 1/2006 | Hardenbol et al. | |
| 2006/0024711 A1 | 2/2006 | Lapidus et al. | |
| 2006/0077536 A1 | 4/2006 | Bromage et al. | |
| 2006/0177833 A1 | 8/2006 | Brenner | |
| 2006/0183107 A1 | 8/2006 | Melkonyan et al. | |
| 2006/0228733 A1 | 10/2006 | Pierce et al. | |
| 2006/0234261 A1 | 10/2006 | Pierce et al. | |
| 2006/0248349 A1 | 11/2006 | Rathjen et al. | |
| 2006/0292611 A1 | 12/2006 | Berka et al. | |
| 2007/0003949 A1 | 1/2007 | Rava | |
| 2007/0020650 A1 | 1/2007 | Kahvejian | |
| 2007/0087362 A1 | 4/2007 | Church et al. | |
| 2007/0117109 A1 | 5/2007 | Rothemund | |
| 2007/0117177 A1 | 5/2007 | Luo et al. | |
| 2007/0172873 A1* | 7/2007 | Brenner | C12Q 1/6816 |
| | | | 435/6.12 |
| 2007/0206275 A1 | 9/2007 | Hemmer et al. | |
| 2007/0231823 A1 | 10/2007 | McKernan et al. | |
| 2007/0292861 A1 | 12/2007 | Thompson | |
| 2007/0292877 A1 | 12/2007 | Dimitrov | |
| 2008/0050718 A1 | 2/2008 | Gesteland et al. | |
| 2008/0176769 A1 | 7/2008 | Rank et al. | |
| 2008/0269068 A1 | 10/2008 | Church et al. | |
| 2009/0005259 A1 | 1/2009 | Drmanac | |
| 2009/0208965 A1 | 8/2009 | Tafas et al. | |
| 2009/0220968 A1 | 9/2009 | Issadore et al. | |
| 2009/0246879 A1 | 10/2009 | Drmanac et al. | |
| 2010/0009868 A1 | 1/2010 | Yan et al. | |
| 2010/0015607 A1 | 1/2010 | Geiss et al. | |
| 2010/0047924 A1 | 2/2010 | Webster et al. | |
| 2010/0087325 A1 | 4/2010 | Buermann | |
| 2010/0151472 A1 | 6/2010 | Nolan et al. | |
| 2010/0223276 A1 | 9/2010 | Al-Shameri et al. | |
| 2010/0268478 A1 | 10/2010 | Andregg et al. | |
| 2011/0020291 A1 | 1/2011 | Banerjee et al. | |
| 2011/0033520 A1 | 2/2011 | Mather et al. | |
| 2011/0086774 A1 | 4/2011 | Dunaway | |
| 2011/0092376 A1 | 4/2011 | Colston, Jr. et al. | |
| 2011/0104693 A1 | 5/2011 | Seligmann | |
| 2011/0223585 A1 | 9/2011 | Gullberg et al. | |
| 2011/0245111 A1 | 10/2011 | Chee | |
| 2011/0257031 A1 | 10/2011 | Bodeau et al. | |
| 2011/0294135 A1 | 12/2011 | Carlson | |
| 2012/0040397 A1 | 2/2012 | Luo et al. | |
| 2012/0065091 A1 | 3/2012 | Willis et al. | |
| 2012/0122712 A1 | 5/2012 | Goldstein | |
| 2012/0252686 A1 | 10/2012 | Umbarger et al. | |
| 2012/0330636 A1 | 12/2012 | Albou | |
| 2013/0017229 A1 | 1/2013 | Mooney et al. | |
| 2013/0084574 A1 | 4/2013 | Dong et al. | |
| 2013/0245096 A1 | 9/2013 | Abitbol | |
| 2014/0049632 A1 | 2/2014 | Hemmer | |
| 2014/0087378 A1 | 3/2014 | Chatre et al. | |
| 2014/0087427 A1 | 3/2014 | Bujnicki et al. | |
| 2014/0200146 A1 | 7/2014 | Xie et al. | |
| 2014/0220587 A1 | 8/2014 | Green, Jr. et al. | |
| 2014/0270435 A1 | 9/2014 | Dunn | |
| 2014/0364333 A1 | 12/2014 | Wu et al. | |
| 2015/0133319 A1 | 5/2015 | Fu et al. | |
| 2016/0024555 A1 | 1/2016 | Church et al. | |
| 2016/0253584 A1 | 9/2016 | Fodor et al. | |
| 2016/0265046 A1 | 9/2016 | Zhang et al. | |
| 2016/0289740 A1 | 10/2016 | Fu et al. | |
| 2016/0369321 A1* | 12/2016 | Landegren | C12Q 1/6816 |
| 2017/0176338 A1 | 6/2017 | Wu et al. | |
| 2017/0212983 A1 | 7/2017 | Cai et al. | |
| 2018/0010166 A1 | 1/2018 | Pierce et al. | |
| 2018/0051322 A1* | 2/2018 | Church | C12Q 1/6869 |
| 2018/0230533 A1 | 8/2018 | Church et al. | |
| 2018/0282787 A1 | 10/2018 | Walter et al. | |
| 2018/0334705 A1 | 11/2018 | Church et al. | |
| 2019/0024144 A1 | 1/2019 | Church et al. | |
| 2019/0085383 A1 | 3/2019 | Church et al. | |
| 2019/0127786 A1 | 5/2019 | Wu et al. | |
| 2019/0155835 A1 | 5/2019 | Daugharthy et al. | |
| 2019/0177718 A1* | 6/2019 | Church | C12Q 1/6869 |
| 2019/0194709 A1 | 6/2019 | Church et al. | |
| 2019/0218608 A1 | 7/2019 | Daugharthy et al. | |
| 2019/0241938 A1 | 8/2019 | Levner et al. | |
| 2019/0241941 A1 | 8/2019 | Levner et al. | |
| 2019/0241950 A1 | 8/2019 | Daugharthy et al. | |
| 2019/0330617 A1 | 10/2019 | Church et al. | |
| 2020/0071751 A1* | 3/2020 | Daugharthy | C12Q 1/6806 |
| 2020/0080144 A1 | 3/2020 | Church et al. | |
| 2020/0354774 A1 | 11/2020 | Church et al. | |
| 2021/0087611 A1 | 3/2021 | Church et al. | |
| 2021/0102238 A1 | 4/2021 | Church et al. | |

FOREIGN PATENT DOCUMENTS

| | | |
|---|---|---|
| JP | 2001122892 A | 5/2001 |
| JP | 4262799 B2 | 5/2009 |
| JP | 2011517555 A | 6/2011 |

(56) References Cited

FOREIGN PATENT DOCUMENTS

| | | |
|---|---|---|
| JP | 2012514475 A | 6/2012 |
| JP | 2012518430 A | 8/2012 |
| JP | 2012170337 A | 9/2012 |
| KR | 20080003402 A | 1/2008 |
| WO | WO-9746704 A1 | 12/1997 |
| WO | WO-9856955 A1 | 12/1998 |
| WO | WO-0058516 A2 | 10/2000 |
| WO | WO-0126708 A1 | 4/2001 |
| WO | WO-0137266 A1 | 5/2001 |
| WO | WO-02057491 A2 | 7/2002 |
| WO | WO-03044229 A1 | 5/2003 |
| WO | WO-2004104645 A2 | 12/2004 |
| WO | WO-2005082098 A2 | 9/2005 |
| WO | WO-2006138257 A2 | 12/2006 |
| WO | WO-2007001986 A2 | 1/2007 |
| WO | WO-2007076128 A2 | 7/2007 |
| WO | WO-2007086900 A2 | 8/2007 |
| WO | WO-2007121489 A2 | 10/2007 |
| WO | WO-2007123744 A2 | 11/2007 |
| WO | WO-2007149696 A1 | 12/2007 |
| WO | WO-2008069973 A2 | 6/2008 |
| WO | WO-2008157696 A2 | 12/2008 |
| WO | WO-2009046149 A1 | 4/2009 |
| WO | WO-2009046348 A1 | 4/2009 |
| WO | WO-2010080134 A1 | 7/2010 |
| WO | WO-2010087325 A1 | 8/2010 |
| WO | WO-2011143583 A1 | 11/2011 |
| WO | WO-2012005595 A2 | 1/2012 |
| WO | WO-2012058638 A2 | 5/2012 |
| WO | WO-2012110899 A2 | 8/2012 |
| WO | WO-2012150035 A1 | 11/2012 |
| WO | WO-2013055995 A2 | 4/2013 |
| WO | WO-2014048083 A1 | 4/2014 |
| WO | WO2014/163886 * | 9/2014 |
| WO | WO-2014163886 A1 | 10/2014 |
| WO | WO-2014182528 A2 | 11/2014 |
| WO | WO-2015118029 A1 | 8/2015 |
| WO | WO-2015127183 A2 | 8/2015 |
| WO | WO-2015148606 A2 | 10/2015 |
| WO | WO-2016028887 A1 | 2/2016 |
| WO | WO-2016081740 A1 | 5/2016 |
| WO | WO-2017079406 A1 | 5/2017 |
| WO | WO-2017161251 A1 | 9/2017 |

OTHER PUBLICATIONS

Mathews, CK., J. of Biological Chemistry 243(21):5610 (Year: 1968).*
Kotewicz et al., Isolation of MMuLV RT lacking RNase H activity. Nucleic Acids Reseasrch 16(1) :265 (Year: 1988).*
Starnes et al. J. of Biological Chemistry 264(12) : 7073 (Year: 1989).*
Davies et al.Crystal Structure of the ribonuclease H domain of HIV-1 Reverse Transcriptase. Science 252 :88 (Year: 1991).*
Li and Beaker. Kinetics of RNA Degradation by Specific Base Catalysis of Transesterification Involving the 2'-Hydroxyl Group. JACS 121 :5364 (Year: 1999).*
Arezi et al., Novel mutations in Moloney Murine Leukemia Virus reverse transcriptase increase thermostability through tighter binding to template-primer. Nucleic Acids Research 37(2) : 473-481 (Year: 2009).*
Ke et al., In situ sequencing for RNA analysis in preserved tissue and cells. Nature Methods 10(9) : 857 (Year: 2013).*
Search Notes in corresponding PCT application PCT/US2019/43773 (Year: 2014).*
AbouHaidar, et al., Non-enzymatic RNA Hydrolysis promoted by the combined catalytic activity of buffers and magnesium Ions. Verlag der Zeitschrift fur naturforschung. Tubingen. 1999; 54c: 542-548.
Ascano., Identification of RNA-protein interaction networks using PAR-CLIP. Wiley interdisciplinary reviews. RNA 3.2 (Mar. 2012): 159-177, DOI:10.1002/wrna.1103.
Brenner, et al., Gene Expression analysis by massively parallel signature sequencing (MPSS) on microbead arrays. Nature Biotechnology 18.6 (Jun. 2000): 630-634, doi:10.1038/76469.
Cao, et al., In-situ Immuno-PCRto detect antigens. The Lancet 356 (Sep. 2000): 1002-1003.
Choi, et al., Next-Generation in Situ Hybridization Chain Reaction: Higher Gain, Lower Cost, Greater Durability. ACS Nano 8.5 (May 2014): 4284-4294, XP055409053, US.
Dasari, et al., Platform for Spatial Molecular Data by Vivek Dasari 1-7 Signature redacted Thesis Supervisor. (Aug. 2015) XP055559164, URL:http://dspace.mit.edu/bitstream/handle/1721.1/107103/971494098-MIT.pdf?sequence=1.
Doillon, et al., Actin Filaments in Normal Dermis and During Wound Healing. The American Journal of Pathology 126.1 (1987): 164-170.
Eliscovich, et al., mRNA on the move: The road to its biological destiny. Journal of Biological Chemistry 288.28 (Jul. 2013): 20361-20368.
European Patent Application No. 12780609.9, Extended European Search Report dated Sep. 23, 2015.
European Patent Application No. 12860433.7, Extended European Search Report dated Aug. 13, 2015.
European Patent Application No. 16862929.3, Extended European Search Report dated May 13, 2019.
European Patent Application No. 17790240.0, Extended European Search Report dated Sep. 4, 2019.
Extended European Search Report dated May 21, 2019 for European Application No. 16862945.9.
Gao, et al., An Efficient strategy for sequencing-by-synthesis. Journal of Nanoscience and nanotechnology. 2010; 10:2988-2993.
Ginart, et al., RNA Sequencing In Situ. Nat Biotechnol 32.6 (Jun. 2014): 543-544, DOI:10.1038/nbt.2921.
Grompe, The rapid detection of unknown mutations in nucleic acids. Nature Genetics (Oct. 1993): 111-117, DOI: 10.1038/ng1093-111.
Han, et al., Quantum-dot-tagged microbeads for multiplexed optical coding of biomolecules. Nature Biotechnology 19.99 (Jul. 2001): 631-635.
International Patent Application No. PCT/US2012/059873, International Preliminary Report on Patentability dated Apr. 24, 2014.
International Patent Application No. PCT/US2012/071398, International Search Report and Written Opinion dated Apr. 8, 2013.
International Patent Application No. PCT/US2013/044241, International Preliminary Report on Patentability dated Dec. 18, 2014.
International Patent Application No. PCT/US2014/18580, International Search Report dated Jul. 11, 2014.
International Patent Application No. PCT/US2018/027583, International Search Report and Written Opinion dated Jun. 29, 2018.
Jambhekar, et al., Cis-acting Determinants of Asymmetric, Cytoplasmic RNA Transport. RNA 13 (2007): 625-642.
Kalivas, et al., FamRCA-RACE: a Rolling Circle Amplification Race for Isolating a Family of Homologous CDNAS in One Reaction and Its Application to Obtain Nac Genes Transcription Factors From Crocus (*Crocus sativus*) Flower. Preparative Biochemistry and Biotechnology 40.3 (Jul. 2010): 177-187.
Lee, et al., "Fluorescent in situ sequencing (FISSEQ) of RNA for gene expression profiling in intact cells and tissues" Nature Protocols (Feb. 12, 2015) 10(3):442-458. XP055272042, GB ISSN:1754-2189, DOI: 10.1038/nprot.2014.191.
Lee, et al., Highly Multiplexed Subcellular RNA Sequencing in Situ. Science 343.6177 (Mar. 2014): 1360-1363, doi: 10.1126/science.1250212.
Matlin, et al., Spatial Expression of the Genome: the Signal Hypothesis at Forty. Nature Reviews. Molecular Cell Biology 12.5 (May 2011): 333-340.
Meeks, et al., Characterization of Genes Encoding Poly(a) Polymerases in Plants: Evidence for Duplication and Functional Specialization. Pios One 4.11 (Nov. 2009): e8082.
PCT/US2019/043773 International Search Report and Written Opinion dated Dec. 3, 2019.
Polidoros, et al., Rolling circle amplification—RACE: A method for simultaneous isolation of 5' and 3' cDNA ends from amplified

(56) References Cited

OTHER PUBLICATIONS cDNA templates. BioTechniques 41.1 (Jul. 2006):35-42. including p. 1/1 of Supplementary Material.
Ravan, et al., Isothermal RNA Detection Through the Formation of DNA Concatemers Contiaining HRP-mimicking DNAzymes on the Surface of Gold Nanoparticles. Biosensors and Bioelectronics 80 (Jan. 2016): 67-73. XP029441324.
Saliba, et al., Single-cell RNA-Seq: Advances and Future Challenges. Nucleic Acids Research 42.14 (2014): 8845-8860, DOI: 10.1093/nar/gku555.
Sano, et al. Immuno-PCR: Very sensitive antigen detection by means of specific antibody-DNA conjugates. Science. 258 (1992): 120-122.
Schweitzer et al. Immunoassays with rolling circle DNA amplification: a versatile platform for ultrasensitive antigen detection. Proceedings of the National Academy of Sciences.USA. 97(18) (Aug. 2000):10113-10119.
Seo, et al. Four-color DNA sequencing by synthesis on a chip using photocleavable fluorescent nucleotides. Proceeding of the National Academy of Sciences USA. 102.17 (Apr. 2005): 5926-5931.
Shendure, et al., Accurate Multiplex Polony Sequencing of an Evolved Bacterial Genome. Science 309.5741 (Sep. 2005): 1728-1732. XP002427180, ISSN: 0036-8075, DOI: 10.1126/SCIENCE.1117839.
Singer-Kruger, et al., Here, There, Everywhere. RNA Biology 11.8 (Aug. 2014): 1031-1039.
Soderberg, et al., Direct Observation of Individual Endogenous Protein Complexes in Situ by Proximity Ligation. Nature Methods 3.12 (Dec. 2006): 995-1000.
Thisse et al., High-resolution in Situ Hybridization to Whole-mount Zebrafish Embryos. Nature Protocols 3.1 (2008): 59-69, Doi:10.1038/nprot.2007.514.
Tsaflaris, et al., Isolation of Three Homologous AP1-like MADS-box Genes in Crocus (*Crocus sativus* L.) and Characterization of Their Expression. Plant Science 166.5 (May 2004): 1235-1243.
U.S. Appl. No. 16/285,292 Office Action dated Nov. 1, 2019.
Weis, et al., Protein Targeting to Subcellular Organelles via mRNA Localization. Biochimica et Biophysica Acta 1833 available online (Apr. 2012): 260-273.
Zhou, et al., In Situ detection of Messenger RNA using digoxiogenin-labeled oligonucleotides and rolling circle amplification. Experimental and molecular Pathology, 2001; 70: 281-288.
Sep. 26, 2008—International Search Report and Written Opinion received in corresponding Application No. PC/ Us2007/03334.
Feb. 19, 2010—U.S. Non-Final Office Action—U.S. Appl. No. 12/187,460.
Sep. 1, 2010—U.S. Final Office Action—U.S. Appl. No. 12/187,460.
A.D. Bates et al., "DNA gyrase can supercoil DNA circles as small as 174 base pairs," The EMBO Journal, vol. 8, No. 6 pp. 1861-1866, 1989.
Amasino et al., Acceleration of nucleic acid hybridization rate by polyethylene glycol, Analytical biochemistry,vol. 152, No. 2, Feb. 1, 1986.
Ann-Christine Syv?nen, "Toward genome-wide SNP genotyping," Nature Genetics Supplement, vol. 37, Jun. 2005, pp. S5-S10.
Beliveau, Brian J. et al., Versatile design and synthesis platform for visualizing genomes with Oligopaint FISH probes, National Academy of Sciences, vol. 109, No. 52, Dec. 11, 2012, pp. 21301-21306.
Beliveau, Brian J. et al., Visualizing Genomes with Oligopaint Fish Probes: In: "Current Protocols in Molecular Biology", Jan. 6, 2014, Wiley, New York, NY.
Beliveau, et al. Single-molecule super-resolution imaging of chromosomes and in situ haplotype visualization using olligopaint FISH probes. Nat Commun. 2015; 6:7147; Abstract, p. 3 [according to the posted document], Fig 1 and its legend; p. 4, Fig 2 and its legend; p. 6, Fig 3 and its legend.
Bouche et al., The effect of spermidine on endonuclease inhibition by agarose contaminants. Analytical biochemistry, Academic press, vol. 115, No. 1, Jul. 15, 1918, pp. 42-45.
Brown et al., Review Article : In situ Hybridization with Riboprobes :An Overview for Veterinary Pathologists. Veterinary Pathology 35 : 159-167 (Year: 1998.
C.A Hutchison III et al., "Cell-free cloning using 029 DNA polymerase," 17332-17336, PNAS, Nov. 29, 2005, vol. 102, No. 48.
Chen, et al., Expansion Microscopy. Science, Jan. 30, 2015; vol. 347, Issue 6221: 543-549.
Chen et al in "Dynamic Imaging of Genomic Loci in Living Human Cells by an Optimized CRISPR/Cas System" (Cell ;Dec. 19, 2013, vol. 155, No. 7, pp. 1479-1491) (Year: 2013).
Chen, et al., Nanoscale imaging of RNA with expansion microscopy. Nature Methods. Aug. 2016; vol. 13, No. 8: pp. 679-687.
Choi & Love et al., Immune-Hybridization Chain Reaction for Enhancing Detection of Individual Cytokine-Secreting Human Peripheral Mononuclear Cells. Analytical Chemistry 83 : 6890-6895 (Year: 2011).
Choi et ai.,Programmable in situ amplification for multiplexed imaging of mRNA expression. Nature Biotechnology 28(11): 1208 (Year: 2010).
Chozinski, et al., Expansion microscopy with conventional antibodies and fluorescent proteins. Nature Methods. Jun. 2016; vol. 13, No. 6: pp. 485-491.
Clausson et al., Compaction of rolling circle amplification products increases signal integrity and signal-to-noise ratio. Scientific Reports, vol. 5. Jul. 23, 2015. p. 12317.
Co-pending U.S. Appl. No. 16/830,372, filed Mar. 26, 2020.
EP17786521.9 Extended European Search Report dated Sep. 5, 2019.
EP17847555.4 Extended European Search Report dated Apr. 21, 2020.
EP17847559.6 Extended European Search Report dated Mar. 30, 2020.
EP19169540.2 Extended European Search Report dated Oct. 22, 2019.
F. Dahl et al., "Circle-to-circle amplification for precise and sensitive DNA analysis," 4548-4553, PNAS, Mar. 30, 2004, vol. 101, No. 13.
G. Leone et al., "Molecular beacon probes combined with amplification by NASBA enable homogeneous, real-time detection of RNA," Nucleic Acids Research, 1998, vol. 26, No. 9, pp. 2150-2155.
Gu et al. "Multiplex single-molecule interaction profiling of DNA-barcoded proteins," Nature, Sep. 21, 2014 (Sep. 21, 2014), vol. 515, pp. 54-557 and Supplementary Information, entire document.
H. Yan et al., "Allelic Variation in Human Gene Expression," Science, vol. 297, Aug. 16, 2002, p. 1143, www. sciencemag.org.
Hansen et al., Sensitive ligand-based protein quantification using immuno-PCR: A critical review of single-probe and proximity ligation assays. Biotechniques 56:217-228 (Year: 2014).
Hirsch et al. "Easily reversible desthiobiotin binding to streptavidin, avidin, and other biotinbinding proteins: uses for protein labeling, detection, and isolation," Analytical Biochemistry, 2002, vol. 308, p. 343-357. entire document.
Irina Kuznetsova et al: "What Macromolecular Crowding Can Do to a Protein". Int.J.Mol. Sci.. vol. 15. No. 12. Dec. 1, 2014 (Dec. 1, 2014). pp. 23090-23140.
J. B. Fan et al., "Parallel Genotyping of Human SNPs Using Generic High-density Oligonucleotide Tag Arrays," 3enome Research, 2000, 10:853-860.
J. Baner et al., "Signal amplification of padlock probes by rolling circle replication," Nucleic Acids Research, 1998, vol. 26, No. 22, pp. 5073-5078.
J. M. Shumaker et al., "Mutation Detection by Solid Phase Primer Extension," Human Mutation 7:346-354 (1996).
J. Tian et al., "Accurate multiplex gene synthesis from programmable DNA microchips," Nature, vol. 432, Dec. 23-30, 2004, pp. 1050-1054, www.nature.com/nature.
Johan Baner et al., "Parallel gene analysis with allele-specific padlock probes and tag microarrays," Nucleic Acids Research, 2003, vol. 31, No. 17, e103, pp. 1-7.
K. Zhang et al., "Sequencing genomes from single cells by polymerase cloning," Nature Biotechnology, vol. 24, No. 6, Jun. 2006, http://www.nature.com/naturebiotechnology.

(56) References Cited

OTHER PUBLICATIONS

Kuimelis et al., Cleavage properties of an oligonucleotide containing a bridged internucleotide 5-phosphorothioate RNA linkage. Nucleic Acids Research 23 (23) : 4753-4760 (Year: 1999).
Larsson, et al., In situ detection and genotyping of individual mRNA molecules. Nature Methods, vol. 7, No. 5, Apr. 11, 2010. pp. 395-397.
M. Nilsson et al., "Padlock Probes: Circularizing Oligonucleotides for Localized DNA Detection," Science, vol. 25, Sep. 30, 1994, pp. 2085-2088.
Mag et al., Synthesis and selective cleavage of an oligodeoxynucleotide containing a bridged internucleotide 5'-phosphorothioate linkage. Nucleic Acids Research 19(7): 1437 (Year: 1991).
Mei, et al., A comprehensive review and performance evaluation of bioinformatics tools for HLA class I peptide-binding prediction. Briefings in bioinformatics, 00(00), 2019, 1-17.
Mitra, et al., In situ localized amplification and contact replication of many individual DNA molecules. Nucleic Acids Research. Information Retrieval Ltd. GB, vol. 27. No. 24. Dec. 15, 1999. p. e34.
Nadji et ai.,"Photochemically and Photoenzymatically Cleavable DNA," J. Am. Chern. Soc. 1992, 114, 9266-9269.
Nair, S. et al., Natural Killer T cells in cancer immunotherapy. Front. Immunol. Sep. 2017; 8(1178): 1-18.
Nir, Guy et al., "Walking along chromosomes with super-resolution imaging, contact maps, and integrative modeling", PLOS Genetics, vol. 14, No. 12, Dec. 26, 2018 (Dec. 26, 2018).
N.P. Gerry et al., "Universal DNA Microarray Method for Multiplex Detection of Low Abundance Point Mutations," J. Mol. Bioi. (1999), 292, 251-262, http://www.idealibrary.com.
Nuovo, G.J., Co-labeling Using In Situ PCR: A Review, Journal of Histochemistry & Cytochemistry. vol. 49. No. 11, Nov. 1, 2001 (Nov. 1, 2001). pp. 1329-1339.
Ohata et al., "Confocal Imaging Analysis of Intracellular Ions in Mixed Cellular Systems or in Situ Using Two Types of Confocal Microscopic Systems," Methods in Enzymology, vol. 307, pp. 425-441 (1999), particularly p. 437.
Oupicky David et al: "Laterally stabilized complexes of DNA with linear reducible polycations: Strategy for triggered intracellular activation of DNA delivery vectors". Journal of the American Chemical Society. American Chemical Society. US. vol. 124. No. 1. Jan. 9, 2002 (Jan. 9, 2002). pp. 8-9.
P. Hardenbol et al., "Highly multiplexed molecular inversion probe genotyping: Over 10,000 targeted SNPs genotyped in a signle tube assay," Genome Res. 2005, 15: 269-275.
P. Hardenbol et al., "Multiplexed genotyping with sequencing-tagged molecular inversion probes," Nature Biotechnology, vol. 21, No. 6, Jun. 2003, pp. 673-678.
Pjanic et al. "Nuclear Factor I genomic binding associates with chromatin boundaries," BMC Genomics, Feb. 12, 2013 {Feb. 12, 2013), vol. 14, No. 99, pp. 1-18. entire document.
P.M. Lizardi et al., "Mutation detection and single-molecule counting using isothermal rolling-circle amplification," Nature Genetics, vol. 19, Jul. 19, 1998, pp. 225-232.
Richardson et al., Experimental and Theoretical Studies of Light-to-Heat Conversion and Collective Heating Effects in Metal Nanoparticle Solutions. Nano Letters 9(3) : 1139-1146 (Year: 2009).
Rongqin, et al., In situ sequencing for RNA analysis in preserved tissue and cells. Nature Methods, vol. 10. No. 9. Jul. 14, 2013. pp. 857-860.
Son C Nguyen: "Strategies for Studying Chromatin Regulation and Organization", May 1, 2018 (May 1, 2018). XP055684323. Retrieved from the Internet: URL:https://dash.harvard.edu/bitstream/handle/1/33493431/NGUYEN-DISSERTATION-2016.pd f?sequence=4 &isAllowed=y [retrieved on Apr. 8, 2020].
Song et al., Hybridization chain reaction-based aptameric system for the highly selective and sensitive detection of protein. Analyst 137: 1396 (Year: 2012).
Srinivas et al., On the biophysics and kinetics of toehold-mediated DNA strand displacement. Nucleic Acids Research 41 (22) : 10641-10658 (Year: 2013).
Supplemental Material for Schweitzer et al. (PNAS 2000; 97(18):10113-10119) (Year: 2000).
Tran et al. "A Universal DNA-Based Protein Detection System," Journal of American Chemical Society, Sep. 25, 2013 {Sep. 25, 2013), vol. 135, No. 38, pp. 14008-14011 and Supporting Information. entire document.
U.S. Appl. No. 14/284,764 Notice of Allowance dated Mar. 28, 2018.
U.S. Appl. No. 14/284,764 Office Action dated Jan. 30, 2017.
U.S. Appl. No. 14/284,764 Office Action dated Jan. 4, 2018.
U.S. Appl. No. 14/284,764 Office Action dated Jun. 14, 2017.
U.S. Appl. No. 15/128,145 Notice of Allowance dated Jul. 17, 2020.
U.S. Appl. No. 15/128,145 Office Action dated Mar. 6, 2020.
U.S. Appl. No. 15/128,145 Office Action dated May 16, 2019.
U.S. Appl. No. 15/504,421 Office Action dated Mar. 5, 2020.
U.S. Appl. No. 15/786,921 Notice of Allowance dated Apr. 23, 2019.
U.S. Appl. No. 15/886,163 Notice of Allowance dated Jan. 24, 2020.
U.S. Serial No. 15/945,192Office Action dated Mar. 13, 2020.
U.S. Appl. No. 16/170,751 Office Action dated Dec. 26, 2019.
U.S. Appl. No. 16/285,292 Office Action dated Apr. 24, 2020.
Wang et al., "The method of axial drift compensation of laser differential confocal microscopy based on zero-tracking," Proc. of SPIE, vol. 9618, 96180X (2015).
Weibrecht, et al., Simultaneous Visualization of Both Signaling Cascade Activity and End-Point Gene Expression in Single Cells, PLOS One. vol. 6. No. 5, May 25, 2011. p. e20148.
Wright et al., "Dynamic closed-loop system for focus tracking using a spatial light modulator and a deformable membrane mirror," Optics Express, vol. 14, No. 1, pp. 222-228 (Jan. 9, 2006).
Xiao et al., Single-step electronic detection of femtomolar DNA by target-induced strand displacement in an electrode-bound duplex. PNAS 103(45): 16677-16680 (Year: 2006).
Yamaguchi et al. "eDNA display: a novel screening method for functional disulfide-rich peptides by solid-phase synthesis and stabilization of mRNA-protein fusions," Nucleic Acids Research, Jun. 15, 2009 {Jun. 15, 2009), vol. 37, No. 16, e108 {p. 1-13 for citations). entire document.
Yaroslavsky, et al. Fluorescence imaging of single-copy DNA sequences within the human genome using PNA-directed padlock probe assembly. Chemistry & biology 2013, 20(3):445-453; Abstract, p. 447, Figure 1 and its legend; p. 448, Table 1.
Y•Wang et ai.,"Allele quantification using molecular inversion probes {MIP)," Nucleic Acids Research, 2005, vol. 33, No. 21, e183,pp. 1-14.
Zhang et al., Dynamic DNA nanotechnology using strand-displacement reactions. Nature Chemistry 3 : 103-113 (Year: 2011).
Zhao et al., An electrochemical aptasensor based on hybridization chain reaction with enzymesignal amplification for interferon-gamma detection. Biosensors and Bioelectronics 36: 129-134 (Year: 2012).
Achim et al., High-throughput spatial mapping of single-cell RNA-seq data to tissue of origin. Nature Biotechnology, vol. 33, No. 5, May 2015, p. 503-511.
Altshuler D, Daly MJ, Lander ES. 2008. "Genetic mapping in human disease" Science 322: 881-8.
Bakal C, Aach J, Church G, Perrimon N. 2007. "Quantitative morphological signatures define local signaling networks regulating cell morphology" Science 316: 1753-6.
Ball MP, Li JB, Gao Y, Lee J, LeProust E, Park l-H, Xie B, Daley GQ, Church GM. 2009. "Targeted and genome-scale methylomics reveals gene body signatures in human cell lines" Nat Biolechnol 27: 361-8.
Bang D, Church GM. 2008. "Gene synthesis by circular assembly amplification" Nat Methods 5: 37-9.
Bell J. 2004. "Predicting disease using genomics" Nature 429: 453-6.
Brenner S, Williams SR, Vermaas EH, Storck T, Moon K, McCollum C, Mao JI, Luo S, Kirchner JJ, Elelr S, DuBridge RB, Burcham T, Albrecht G. 2000. "In vitro cloning of complex mixtures of DNA

(56) References Cited

OTHER PUBLICATIONS on microbeads: physical separation of differentially expressed cDNAs" Proc Nall Acad Sci US A 97: 1665-70. PMC ID: PMC26493.
Chiang DY, Getz G, Jaffe DB, O'Kelly MJ, Zhao X, Carter SL, Russ C, Nusbaum C, Meyerson M, Lander ES. 2009. High-resolution mapping of copy-number alterations with massively parallel sequencing Nat Methods 6: 99-103. PMC ID: PMC2630795.
Choy E, Yelensky R, Bonakdar S, Plenge RM, Saxena R, De Jager PL, Shaw SY, Wolfish CS, Slavik JM, Cotsapas C, Rivas M, Derrnitzakis ET, Cahir-McFarland E, Kieff E, HafterD, Daly MJ, Altshuler D. 2008. "Genetic analysis of human traits in vitro: drug response and gene expression in lymphoblasloid cell lines" PLoS Genet 4: e1000287. PMC ID: PMC2583954.
Christian AT, Pattee MS, Allix CM, Reed BE, Sorensen KJ, Tucker JD. 2001. "Detection of DNA point mutations and mRNA expression levels by rolling circle amplification in individual cells" Proc Nall Acad Sci U SA 98: 14238-43. PMC ID: PMC64666.
Church et al.; Center for Casual Consequences of Variation {CCV) "An NHGRI Center for Excellence in Genomic Science" http://ccv.med.harvard.edu; Wayback Machine {Jul. 3, 2011).
Church et al.; Center for Casual Consequences of Variation {CCV) "Our four Specific Aims" http://ccv.med.harvard. edu/specific_aims.htm; Wayback Machine {Aug. 13, 2011).
Church GM. 2006. "Genomes for all" Sci Am 294: 46-54.
Church GM, Porreca GJ, Terry RC, Lares M. 2008. "High-Speed Imaging for DNA Sequencing" Biopholonics (http:// NWW.pholonics.com/Conlenl/ReadArticle.aspx? ArticleID=33989).
Church; "Proposal for a Center for the determination of the Casual Transcriptional Consequences of Human Genetic Variation {CTCHGV)" http://ccv.med.harvard.edu/CEGS09_Complete_Proposal_minus_Admin_Sections.09May21.final.pdf; Wayback Machine {Aug. 13, 2011).
Cookson W, Liang L, Abecasis G, Moffatt M, Lathrop M. 2009. "Mapping complex disease traits with global gene expression" Nat Rev Genet 10: 184-94.
de Bakker PI, Yelensky R, Pe'er I, Gabriel SB, Daly MJ, Altshuler D. 2005. "Efficiency and power in genetic associalior studies" Nat Genet 37: 1217-23.
Deng J, Shoemaker R, Xie B, Gore A, LeProust EM, Anlosiewicz-Bourget J, Egli D, Maherali N, Park IH, Yu J, Daley GQ, Eggan K, Hochedlinger K, Thomson J, Wang W, Gao Y, Zhang K. 2009. "Targeted bisulfite sequencing reveals changes in DNA methylalion associated with nuclear reprogramming" Nat Biolechnol 27: 353-60.
Dixon AL, Liang L, Moffatt MF, Chen W, Heath S, Wong KC, Taylor J, Burnell E, Gut I, Farrall M, Lathrop GM, Abecasis GR, Cookson WO. 2007. "A genome-wide association study of global gene expression" Nat Genet 39: 1202-7.
Eberwine J, Kacharmina JE, Andrews C, Miyashiro K, McIntosh T, Becker K, Barrell T, Hinkle D, Deni G, Marciano P. 2001. "mRna expression analysis of tissue sections and single cells" J Neurosci 21: 8310-4.
Eid J, Fehr A, Gray J, Luong K, Lyle J, Otto G, Peluso P, Rank D, Baybayan P, Bettman B, Bibillo A, Bjornson K, Chaudhuri B, Christians F, Cicero R, Clark S, Dalal R, Dewinter A, Dixon J, Foquet M, Gaertner A, Hardenbol P, Heiner C, Hester K, Holden D, Kearns G, Kong X, Kuse R, Lacroix Y, Lin S, Lundquist P, Ma C, Marks P, Maxham M, Murphy D, Park I, Pham T, Phillips M, Roy J, Sebra R, Shen G, Sorenson J, Tomaney A, Travers K, Trulson M, Vieceli J, Wegener J, Wu D, Yang A, Zaccarin D, Zhao P, Zhong F, Korlach J, Turner S. 2009. "Real-time DNA sequencing from single polymerase molecules" Science 323: 133-8.
Emilsson V, Thorleifsson G, Zhang B, Leonardson AS, Zink F, Zhu J, Carlson S, Helgason A, Walters GB, Gunnarsdollir S, Mouy M, Sleinthorsdollir V, Eiriksdottir GH, Bjornsdollir G, Reynisdollir I, Gudbjartsson D, Helgadollir A, Jonasdottir A, Jonasdollir A, Styrkarsdottir U, Grelarsdottir S, Magnusson KP, Slefansson H, Fossdal R, Kristjansson K, Gislason HG, Slefansson T, Leifsson BG, Thorsleinsdollir U, Lamb JR, Gulcher JR, Reitman ML, Kong A, Schadt EE, Slefansson K. 2008; "Genetics of aene exoression and its effect on disease" Nature 452: 423-8.
EP19180827.8 Extended European Search Report dated Dec. 17, 2019.
Gohring et al., Biochem., vol. 36, pp. 8276-8283, Published 1997.
Gusev, et al., Rolling circle amplification: a new approach to increase sensitivity for immunohistochemistry and flow cytometry. Am J Pathol. Jul. 2001;159(1):63-9. doi: 10.1016/S0002-9440(10)61674-4.
Harris TD, Buzby PR, Babcock H, Beer E, Bowers J, Braslavsky I, Causey M, Colonel! J, Dimeo J, Efcavitch JW, Giladi E, Gill J, Healy J, Jarosz M, Lapen D, Moulton K, Quake SR, Steinmann K, Thayer E, Tyurina A, Ward R, Weiss H, Xie Z. 2008. "Single-molecule DNA sequencing of a viral genome" Science 320: 106-9.
International HapMap C. 2005. "A haplotype map of the human genome" Nature 437: 1299-320. PMCID: PMC1880871.
J. H. Lee, M.D. Ph.D. presentation entitled "Population-wide Tissue-specific Functional Analysis of Human iPS Cells Using Single-Cell In Situ Sequencing" George Church Laboratory, Wyss Institute for Biology Inspired Engineering, Harvard Medical School, Boston, Jan. 10, 2010.
Kim JB, Porreca GJ, Song L, Greenway SC, Gorham JM, Church GM, Seidman CE, Seidman JG. 2007. "Polony multiplex analysis of gene expression {PMAGE) in mouse hypertrophic cardiomyopathy" Science 316: 1481-4.
Klein RJ. 2007. "Power analysis for genome-wide association studies" BMC Genet 8: 58. PMC ID: PMC2042984.
Kolb HC, Finn MG, B. SK. 2001. "Click Chemistry: Diverse Chemical Function from a Few Good Reactions" Angew.Chem. Int. 40: 2004-21.
Kurimoto K, Yabuta Y, Ohinata Y, Saitou M. 2007. "Global single-cell cDNA amplification to provide a template for representative high-density oligonucleotide microarray analysis" Nat Protoc 2: 739-52.
Kwan T, Benovoy D, Dias C, Gurd S, Provencher C, Beaulieu P, Hudson TJ, Sladek R, Majewski J_2008. "Genome-wide analysis of transcript isoform variation in humans" Nat Genet 40: 225-31.
Kwiatkowski M, Fredriksson S, Isaksson A, Nilsson M, Landegren U. 1999. "Inversion of in situ synthesized oligonucleolides: improved reagents for hybridization and primer extension in DNA microarrays" Nucleic Acids Res 27: 1710-4. PMC ID: PMC148770.
Li JB, Gao Y, Aach J, Zhang K, Kryukov GV, Xie B, Ahiford A, Yoon J-K, Rosenbaum AM, Wait-Zaranek A, LeProust E, Sunyaev S, Church GM. 2009. "Multiplex padlock capture and sequencing reveal human hypermulable CpG variations" Genome Res in press.
Li JB, Levanon EY, Yoon J-K, Aach J, Xie B, LeProust E, Zhang K, Gao Y, G.M. C. 2009. "Genome-wide Identification of Human RNA Editing Sites by Parallel DNA Capturing and Sequencing" Science in press.
Lizardi, Next-generation sequencing-by-hybridization. Nature Biotechnology, vol. 26, No. 6, Jun. 2008, pp. 649-650.
Markaki et al. "Fluorescence In Situ Hybridization Applications for Super-Resolution 3D Structured Illumination Microscopy" Methods in Microbiology, Jan. 2013.
Mccarroll SA. 2008. "Extending genome-wide association studies to copy-number variation" Hum Mol Genet 17: R135-42.
Meng Q, Kim DH, Bai X, Bi L, Turro NJ, Ju J_2006. "Design and synthesis of a photocleavable fluorescent nucleotide 3'-O-allyl-dGTP-PC-Bodipy-FL-510 as a reversible terminator for DNA sequencing by synthesis" J Org Chem 71: 3248-52.
Mignardi et al., Fourth-generation sequencing in the cell and the clinic. Genome Medicine, 2014, 6:31.
Mitra RD, Bully VL, Shendure J, Williams BR, Housman DE, Church GM. 2003. "Digital genotyping and haplotyping with polymerase colonies" Proc Nall Acad Sci US A 100: 5926-31. PMC ID: PMC156303.
Mitra RD, Shendure J, Olejnik J, Edyta Krzymanska 0, Church GM. 2003. "Fluorescent in situ sequencing on Jolymerase colonies" Anal Biochem 320: 55-65.
Morley M, Molony CM, Weber TM, Devlin JL, Ewens KG, Spielman RS, Cheung VG. 2004. "Genetic analysis of Jenome-wide variation in human gene expression" Nature 430: 743-7.

(56) References Cited

OTHER PUBLICATIONS

Pan X, Urban AE, Palejev D, Schulz V, Grubert F, Hu Y, Snyder M, Weissman SM. 2008. "A procedure for highly specific, sensitive, and unbiased whole-genome amplification" Proc Nall Acad Sci US A 105: 15499-504. PMC ID:PMC2563063.

PCT/US2017/028278 International Search Report dated Jul. 27, 2017.

PI: Piezo Nano Positioning, 2008 (online), retrieved on Aug. 12, 2020, pp. 1-6 https://www.pi-usa.us/fileadmin/user_upload/pi_us/files/product_datasheets/N725_Piezo_Focus_Positioner.pdf.

Pihlak et al., Rapid genome sequencing with short universal tiling probes. Nature biotechnology, vol. 26, No. 6, Jun. 2008, pp. 676-684.

Porreca GJ, Shendure J, Church GM. 2006. "Polony DNA sequencing" Curr Protoc Mol Biol Chapter 7: Unit 7 8.

Porreca GJ, Zhang K, Li JB, Xie B, Austin D, Vassallo SL, LeProust EM, Peck BJ, Emig CJ, Dahl F, Gao Y, Church GM, Shendure J_2007. "Multiplex amplification of large sets of human exons" Nat Methods 4: 931-6.

Rao et al., "A 3D Map of the Human Genome at Kilobase Resolution Reveals Principles of Chromatin Looping," Cell,vol. 159, No. 7, pp. 1665-1680 (Dec. 18, 2014).

Risch N, Merikangas K. 1996. "The future of genetic studies of complex human diseases" Science 273: 1516-7.

Sachidanandam R, Weissman D, Schmidt SC, Kakol JM, Stein LD, Marth G, Sherry S, Mullikin JC, Mortimore BJ, Willey DL, Hunt SE, Cole CG, Coggill PC, Rice CM, Ning Z, Rogers J, Bentley DR, Kwok PY, Mardis ER, Yeh RT, Schultz B, Cook L, Davenport R, Dante M, Fulton L, Hillier L, Waterston RH, McPherson JD, Gilman B, Schaffner S, Van Etten WJ, Reich D, Higgins J, Daly MJ, Blumenstiel B, Baldwin J, Stange-Thomann N, Zody MC, Linton L, Lander ES, Altshuler D, International SNPMWG. 2001. "A map of human genome sequence variation containing 1.42 million single nucleotide polymorphisms" Nature 409: 928-33.

Schadt EE, Molony C, Chudin E, Hao K, Yang X, Lum PY, Kasarskis A, Zhang B, Wang S, Suver C, Zhu J, Millstein J, Sieberts S, Lamb J, GuhaThakurta D, Derry J, Storey JD, Avila-Campillo I, Kruger MJ, Johnson JM, Rohl CA, van Nas A, Mehrabian M, Drake TA, Lusis AJ, Smith RC, Guengerich FP, Strom SC, Schuetz E, Rushmore TH, Ulrich R. 2008. Mapping the genetic architecture of gene expression in human liver PLoS Biol 6: e107. PMC ID: PMC2365981.

Schadt EE, Monks SA, Drake TA, Lusis AJ, Che N, Colinayo V, Ruff TG, Milligan SB, Lamb JR, Cavel G, Linsley PS, Mao M, Stoughton RB, Friend SH. 2003. "Genetics of gene expression surveyed in maize, mouse and man" Nature 122: 297-302.

Serre D, Gurd S, Ge B, Sladek R, Sinnett D, Harmsen E, Bibikova M, Chudin E, Barker DL, Dickinson T, Fan JB, Hudson T J_2008. "Differential allelic expression in the human genome: a robust approach to identify genetic and epigenelic cis-acling mechanisms regulating gene expression" PLoS Genet 4: e1000006. PMC ID: PMC2265535.

Shendure J, Mitra RD, Varma C, Church GM. 2004. "Advanced sequencing technologies: methods and goals" Nat Rev Genet 5: 335-44.

Shendure JA, Porreca GJ, Church GM. 2008. "Overview of DNA sequencing strategies" Curr Protec Mol Biol Chapter 7: Unit 7 1.

Stougaard M, Lohmann JS, Zajac M, Hamilton-Dutoit S, Koch J_2007. "In situ detection of nonpolyadenylated RNA molecules using Turtle Probes and target primed rolling circle PRINS" BMC Biotechnol 7: 69. PMC ID: PMC2203993.

Tang F, Barbacioru C, Wang Y, Nordman E, Lee C, Xu N, Wang X, Bodeau J, Tuch BB, Siddiqui A, Lao K, Surani MA. 2009. "mRNA-Seq whole-transcriptome analysis of a single cell" Nat Methods 6: 377-82.

Terry R, Porreca G, McCarthy K, Church GM. 2008. Polonator Instrument http://www.polonator.org; Wayback Machine (Aug. 7, 2008) "Flow Cells".

Terry R, Porreca G, McCarthy K, Church GM. 2008. Polonator Instrument http://www.polonator.org; Wayback Machine (Aug. 7, 2008) "Instrument Overview".

Terry R, Porreca G, McCarthy K, Church GM. 2008. Polonator Instrument http://www.polonator.org; Wayback Machine (Aug. 7, 2008) "Sollware".

Terry R, Porreca G, McCarthy K, Church GM. 2008. Polonator Instrument http://www.polonator.org; Wayback Machine Aug. 7, 2008) "Open, Affordable, Sequencing_".

Terry R, Porreca G, McCarthy K, Church GM. 2008. Polonator Instrument http://www.polonator.org; Wayback Machine (Aug. 7, 2008) "Protocols".

Terry R, Porreca G, McCarthy K, Church GM. 2008. Polonator Instrument http://www.polonator.org; Wayback Machine (Aug. 7, 2008) "Reagent Kits".

Terry R, Porreca G, McCarthy K, Church GM. 2008. Polonator Instrument http://www.polonator.org; Wayback Machine (Aug. 7, 2008) "The Polonator Ecosystem".

Terry R, Porreca G, McCarthy K, Church GM. 2008. Polonator Instrument http://www.polonator.org; Wayback Machine (Aug. 7, 2008) "The Vision".

Terry R, Porreca G, McCarthy K, Church GM. 2008. Polonator Instrument http://www.polonator.org; Wayback Machine (Jul. 5, 2008) "Polony Sequence Protocols".

Terry R, Porreca G, McCarthy K, Church GM. 2008. Polonator Instrument http://www.polonator.org; Wayback Machine (Sep. 5, 2008) "Bead Capping Protocol".

Terry R, Porreca G, McCarthy K, Church GM. 2008. Polonator Instrument http://www.polonator.org; Wayback Machine (Sep. 5, 2008) "Bead Enrichment Protocol".

Terry R, Porreca G, McCarthy K, Church GM. 2008. Polonator Instrument http://www.polonator.org; Wayback Machine (Sep. 5, 2008) "Coverslip Aminosilanation and Arraying Protocol".

Terry R, Porreca G, McCarthy K, Church GM. 2008. Polonator Instrument http://www.polonator.org; Wayback Machine (Sep. 5, 2008) "Emulsion Breaking Protocol".

Terry R, Porreca G, McCarthy K, Church GM. 2008. Polonator Instrument http://www.polonator.org; Wayback Machine (Sep. 5, 2008) "Emulsion PCR Protocol".

Terry R, Porreca G, McCarthy K, Church GM. 2008. Polonator Instrument http://www.polonator.org; Wayback Machine (Sep. 5, 2008) "Emulsion PCR/Bead Capping Kits".

Terry R, Porreca G, McCarthy K, Church GM. 2008. Polonator Instrument http://www.polonator.org; Wayback Machine (Sep. 5, 2008) "Enrichment Kits".

Terry R, Porreca G, McCarthy K, Church GM. 2008. Polonator Instrument http://www.polonator.org; Wayback Machine (Sep. 5, 2008) "Help Wanted".

Terry R, Porreca G, McCarthy K, Church GM. 2008. Polonator Instrument http://www.polonator.org; Wayback Machine (Sep. 5, 2008) "Paired-Leg Library Kits".

Terry R, Porreca G, McCarthy K, Church GM. 2008. Polonator Instrument http://www.polonator.org; Wayback Machine (Sep. 5, 2008) "PET {Paired End-Tag) Genomic Shotgun Library Construction Protocol".

Terry R, Porreca G, McCarthy K, Church GM. 2008. Polonator Instrument http://www.polonator.org; Wayback Machine (Sep. 5, 2008) "Polony Sequence by Ligation Protocol".

Terry R, Porreca G, McCarthy K, Church GM. 2008. Polonator Instrument http://www.polonator.org; Wayback Machine (Sep. 5, 2008) "Run Kits".

U.S. Appl. No. 15/945,192 Notice of Allowance dated Sep. 16, 2020.

U.S. Appl. No. 16/095,456 Notice of Allowance dated Feb. 12, 2021.

U.S. Appl. No. 16/157,243 Notice of Allowance dated Mar. 24, 2021.

U.S. Appl. No. 16/157,243 Office Action dated Aug. 3, 2020.

U.S. Appl. No. 16/170,751 Office Action dated Jun. 24, 2020.

U.S. Appl. No. 16/255,920 Office Action dated Jul. 2, 2020.

U.S. Appl. No. 16/285,292 Notice of Allowance dated Apr. 9, 2021.

U.S. Appl. No. 16/285,292 Notice of Allowance dated Mar. 15, 2021.

(56) References Cited

OTHER PUBLICATIONS

U.S. Appl. No. 16/285,292 Office Action dated Nov. 10, 2020.
U.S. Appl. No. 16/386,337 Office Action dated Sep. 25, 2020.
U.S. Appl. No. 16/393,215 Notice of Allowance dated Dec. 24, 2020.
U.S. Appl. No. 16/393,215 Office Action dated Aug. 3, 2020.
U.S. Appl. No. 16/830,372 Office Action dated Apr. 29, 2021.
U.S. Appl. No. 16/941,585 Notice of Allowance dated Feb. 17, 2021.
U.S. Appl. No. 16/941,585 Office Action dated Oct. 21, 2020.
U.S. Appl. No. 17/122,1680ffice Action dated Jan. 27, 2021.
Vigneault F, Sismour AM, Church GM. 2008."Efficient microRNA capture and bar-coding via enzymatic oligonucleotide adenylation" Nat Methods 5: 777-9.
Wang Z, Gerstein M, Snyder M. 2009. "RNA-Seq: a revolutionary tool for transcriptomics" Nat Rev Genet 10: 57-63.
Wu J, Zhang S, Meng Q, Cao H, Li Z, Li X, Shi S, Kim DH, Bi L, Turro NJ, Ju J. 2007. "3'-O-modified nucleotides as reversible terminators for pyrosequencing" Proc Natl Acad Sci US A 104: 16462-7. PMC ID: PMC2034218.
Zhang K, Li JB, Gao Y, Egli D, Xie B, Deng J, Li Z, Lee J, Aach J, Leproust E, Eggan K, Church GM. 2009. "Digital RNA Allelotyping Reveals Tissue-specific and Allele-specific Gene Expression in Human" Nat Methods. Aug. 2009; 6(8): 613-618.
Zhang K, Martiny AC, Reppas NB, Barry KW, Malek J, Chisholm SW, Church GM. 2006. "Sequencing genomes from single cells by polymerase cloning" Nat Biotechnol 24: 680-6.
Zhang K, Zhu J, Shendure J, Porreca GJ, Aach JD, Mitra RD, Church GM. 2006. "Long-range polony haplotyping of individual human chromosome molecules" Nat Genet 38: 382-7.

* cited by examiner

METHODS AND SYSTEMS FOR SAMPLE PROCESSING OR ANALYSIS

CROSS-REFERENCE

This application is a continuation of International Application No. PCT/US19/43773, filed Jul. 26, 2019, which claims priority to U.S. Provisional Patent Application No. 62/711,994, filed Jul. 30, 2018, which is entirely incorporated herein by reference.

BACKGROUND

A padlock probe may be a linear circularizable oligonucleotide which has free 5' and 3' ends which are available for ligation, to result in the adoption of a circular conformation. For circularization (e.g., by ligation) to occur, the padlock probe may have a free 5' phosphate group or 5' adenylated end. To allow the juxtaposition of the ends of the padlock probe for ligation, the padlock probe may be configured to have its 5' and 3' terminal regions complementary to its target sequence (e.g., a ribonucleic acid or synthesized complementary deoxyribonucleic acid (cDNA) molecule in the cell sample to be analyzed). These regions of complementarity may allow specific binding of the padlock probe to its target sequence by virtue of hybridization to specific sequences in the target.

SUMMARY

The present disclosure provides methods and systems for nucleic acid sequence detection in a biological sample having a three-dimensional matrix. The present disclosure also provides methods and systems for sample processing for use in target analysis or detection in a downstream application, such as in situ sequencing.

In an aspect, the disclosure provides a method for identification of a nucleic acid sequence in a biological sample. In one embodiment, the method comprises: (a) providing the biological sample comprising a ribonucleic acid (RNA) molecule hybridized to a deoxyribonucleic acid molecule (DNA) in a three-dimensional (3D) matrix, wherein the RNA molecule comprises the nucleic acid sequence; (b) using a reverse transcriptase to degrade or digest at least a portion of the RNA molecule hybridized to the DNA molecule, which DNA molecule comprises an additional nucleic acid sequence that is a reverse complement of the nucleic acid sequence; and (c) detecting the additional nucleic acid sequence in the biological sample, thereby identifying the nucleic acid sequence.

In some embodiments, the DNA molecule is a complementary deoxyribonucleic acid (cDNA) molecule. In some embodiments, the method further comprises, prior to (a), using an additional reverse transcriptase to reverse transcribe the RNA molecule to generate the DNA molecule hybridized to the RNA molecule in the biological sample. In some embodiments, the method further comprises, prior to (a), using the reverse transcriptase to reverse transcribe the RNA molecule to generate the DNA molecule hybridized to the RNA molecule in the biological sample.

In some embodiments, the DNA molecule is immobilized to the 3D matrix. In some embodiments, the DNA molecule comprises a functional moiety, and wherein the DNA molecule is immobilized to the 3D matrix via the functional moiety. In some embodiments, the RNA molecule is immobilized to the 3D matrix. In some embodiments, the RNA molecule comprises a functional moiety, and wherein the RNA molecule is immobilized to the 3D matrix via the functional moiety. In some embodiments, the method further comprises using a matrix-forming material to form the 3D matrix.

In some embodiments, (c) comprises contacting the cDNA molecule with a probe. In some embodiments, the probe comprises a functional moiety, wherein the probe is immobilized to the 3D matrix via the functional moiety. In some embodiments, the probe is a padlock probe, wherein the padlock probe comprises 5' and 3' terminal regions complementary to the cDNA molecule. In some embodiments, the method further comprises hybridizing the 5' and 3' terminal regions of the padlock probe to the cDNA molecule. In some embodiments, the method further comprises circularizing the padlock probe by ligating two ends of the padlock probe together, to yield a circularized padlock probe. In some embodiments, the two ends of the padlock probe are contiguous. In some embodiments, the two ends of the padlock probe are separated by a gap region comprising at least one nucleotide. In some embodiments, the gap region comprises from 2 to 500 nucleotides. In some embodiments, the method further comprises filling the gap region by incorporating at least one nucleotide in an extension reaction. In some embodiments, the method further comprises filling the gap region by at least one additional nucleotide or an additional oligonucleotide sequence. In some embodiments, the additional oligonucleotide sequence is from 2 to 500 nucleotides in length.

In some embodiments, the method further comprises subjecting the circularized padlock probe to rolling circle amplification (RCA) to generate an amplification product of a sequence of the circularized padlock probe, which amplification product comprises a nucleic acid sequence corresponding to the nucleic acid sequence of the RNA molecule. In some embodiments, the method further comprises detecting the nucleic acid sequence of the amplification product, thereby identifying the nucleic acid sequence of the RNA molecule.

In some embodiments, the reverse transcriptase or the additional reverse transcriptase has RNA catalytic cleavage activity. In some embodiments, the reverse transcriptase or the additional reverse transcriptase has RNA catalytic cleavage activity of an RNA/DNA duplex. In some embodiments, the reverse transcriptase or the additional reverse transcriptase is an Avian myeloblastosis virus (AMV) reverse transcriptase, a wild type human immunodeficiency virus-1 (HIV-1) reverse transcriptase, or a Moloney Murine Leukemia Virus (M-MLV) reverse transcriptase.

In some embodiments, the method further comprises, prior to (a), hybridizing a reverse transcription primer to the RNA molecule. In some embodiments, the reverse transcription primer is hybridizable to the 5' terminal region of the padlock probe. In some embodiments, the reverse transcription primer comprises a functional moiety, wherein the cDNA molecule is immobilized to the 3D matrix via the function moiety. In some embodiments, the biological sample comprises a plurality of RNA molecules, which plurality of RNA molecules has a relative 3D spatial relationship.

In some embodiments, (b) is performed under a first set of conditions and using an additional reverse transcriptase or the reverse transcriptase to reverse transcribe the RNA molecule is performed under a second set of conditions, wherein the first set of conditions is different than the second set of conditions. In some embodiments, the first set of conditions or the second set of conditions is selected from the group consisting of pH, temperature, cofactor concentration, and cation concentration. In some embodiments, the cofactor or cation comprises $Mg^{2+}$, $Mn^{2+}$, $Na^+$, ATP, NADPH. In some embodiments, the second set of conditions inhibits RNase activity of the reverse transcriptase. In some embodiments, the second set of conditions comprises an RNase inhibitor. In some embodiments, the RNase inhibitor is a small molecule inhibitor or a polypeptide.

In another aspect, the disclosure provides a method for identification of a nucleic acid sequence in a biological sample. In one embodiment, the method comprises: (a) providing the biological sample comprising a ribonucleic acid (RNA) molecule hybridized to a deoxyribonucleic acid molecule (DNA) in a three-dimensional (3D) matrix, wherein the RNA molecule comprises the nucleic acid sequence; (b) using a deoxyribonucleic acid (DNA) binding protein that is not a reverse transcriptase or a ribonuclease to degrade or digest at least a portion of the RNA molecule hybridized to the DNA molecule, which DNA molecule comprises an additional nucleic acid sequence that is a reverse complement of the nucleic acid sequence; and (c) detecting the additional nucleic acid sequence in the biological sample, thereby identifying the nucleic acid sequence.

In some embodiments, the DNA molecule is a complementary deoxyribonucleic acid (cDNA) molecule. In some embodiments, the method further comprises, prior to (a), using a reverse transcriptase to reverse transcribe the RNA molecule to generate the DNA molecule hybridized to the RNA molecule in the biological sample.

In some embodiments, the DNA molecule is immobilized to the 3D matrix. In some embodiments, the DNA molecule comprises a functional moiety, and wherein the DNA molecule is immobilized to the 3D matrix via the functional moiety. In some embodiments, the RNA molecule is immobilized to the 3D matrix. In some embodiments, the RNA molecule comprises a functional moiety, and wherein the RNA molecule is immobilized to the 3D matrix via the functional moiety. In some embodiments, the method further comprises using a matrix-forming material to form the 3D matrix.

In some embodiments, (c) comprises contacting the cDNA molecule with a probe. In some embodiments, the probe comprises a functional moiety, wherein the probe is immobilized to the 3D matrix via the functional moiety. In some embodiments, the probe is a padlock probe, wherein the padlock probe comprises 5' and 3' terminal regions complementary to the cDNA molecule, and hybridizing the 5' and 3' terminal regions of the padlock probe to the cDNA molecule. In some embodiments, the method further comprises circularizing the padlock probe by ligating two ends of the padlock probe together, to yield a circularized padlock probe. In some embodiments, the two ends of the padlock probe are contiguous. In some embodiments, the two ends of the padlock probe are separated by a gap region comprising at least one nucleotide. In some embodiments, the gap region comprises from 2 to 500 nucleotides. In some embodiments, the method further comprises filling the gap region by incorporating at least one nucleotide in an extension reaction. In some embodiments, the method further comprises filling the gap region by at least one additional nucleotide or an additional oligonucleotide sequence. In some embodiments, the additional oligonucleotide sequence is from 2 to 500 nucleotides in length.

In some embodiments, the method further comprises subjecting the circularized padlock probe to rolling circle amplification (RCA) to generate an amplification product of a sequence of the circularized padlock probe, which amplification product comprises a nucleic acid sequence corresponding to the nucleic acid sequence of the RNA molecule. In some embodiments, the method further comprises detecting the nucleic acid sequence of the amplification product, thereby identifying the nucleic acid sequence of the RNA molecule.

In some embodiments, the DNA binding protein has RNA catalytic cleavage activity. In some embodiments, the DNA binding protein stabilizes the DNA molecule. In some embodiments, the DNA binding protein increases a melting temperature of the DNA molecule. In some embodiments, the DNA binding protein is Sso7d.

In some embodiments, the method further comprises, prior to (a), hybridizing a reverse transcription primer to the RNA molecule. In some embodiments, the reverse transcription primer is hybridizable to the 5' terminal region of the padlock probe. In some embodiments, the reverse transcription primer comprises a functional moiety, wherein the reverse transcription primer or the DNA molecule is immobilized to the 3D matrix via the function moiety. In some embodiments, the biological sample comprises a plurality of RNA molecules, which plurality of RNA molecules has a relative 3D spatial relationship.

In another aspect, the disclosure provides a method for identification of a nucleic acid sequence in a biological sample. In one embodiment, the method comprises: (a) providing the biological sample comprising a ribonucleic acid (RNA) molecule hybridized to a deoxyribonucleic acid molecule (DNA) in a three-dimensional (3D) matrix, wherein the RNA molecule comprises the nucleic acid sequence; (b) non-enzymatically degrading at least a portion of the RNA molecule hybridized to the DNA molecule, which DNA molecule comprises an additional nucleic acid sequence that is a reverse complement of the nucleic acid sequence; (c) contacting the DNA molecule with a probe; and (d) detecting a sequence of the probe or a derivative thereof, thereby identifying the nucleic acid sequence of the RNA molecule.

In some embodiments, the DNA molecule is a complementary deoxyribonucleic acid (cDNA) molecule. In some embodiments, the method further comprises, prior to (a), using a reverse transcriptase to reverse transcribe the RNA molecule to generate the DNA molecule hybridized to the RNA molecule in the biological sample. In some embodiments, the DNA molecule is immobilized to the 3D matrix. In some embodiments, the DNA molecule comprises a functional moiety, wherein the DNA molecule is immobilized to the 3D matrix via the functional moiety. In some embodiments, the RNA molecule is immobilized to the 3D matrix. In some embodiments, the RNA molecule comprises a functional moiety, wherein the RNA molecule is immobilized to the 3D matrix via the functional moiety.

In some embodiments, the probe is a padlock probe. In some embodiments, the probe comprises a functional moiety, wherein the probe is immobilized to the 3D matrix via the functional moiety. In some embodiments, the method further comprises using a matrix-forming material to form the 3D matrix. In some embodiments, the padlock probe comprises 5' and 3' terminal regions complementary to the DNA molecule. In some embodiments, the method further comprises hybridizing the 5' and 3' terminal regions of the padlock probe to the DNA molecule.

In some embodiments, the method further comprises circularizing the padlock probe by coupling two ends of the padlock probe together, to yield a circularized padlock probe, and detecting a nucleic acid sequence of the circularized padlock probe or a derivative thereof, thereby identifying the nucleic acid sequence of the RNA molecule. In some embodiments, the two ends of the padlock probe are contiguous. In some embodiments, the two ends of the padlock probe are separated by a gap region comprising at least one nucleotide. In some embodiments, the gap region comprises from 2 to 500 nucleotides. In some embodiments, the method further comprises filling the gap region by incorporating at least one nucleotide in an extension reaction. In some embodiments, the method further comprises filling the gap region by at least one additional nucleotide or an additional oligonucleotide sequence. In some embodiments, the additional oligonucleotide sequence is from 2 to 500 nucleotides in length.

In some embodiments, (c) comprises subjecting the circularized padlock probe to rolling circle amplification (RCA) to generate an amplification product of a sequence of the circularized padlock probe, which amplification product comprises a nucleic acid sequence corresponding to the nucleic acid sequence of the RNA molecule. In some embodiments, (d) comprises detecting the nucleic acid sequence of the amplification product, thereby identifying the nucleic acid sequence of the RNA molecule.

In some embodiments, the method further comprises, prior to (a), hybridizing a reverse transcription primer to the RNA molecule. In some embodiments, the reverse transcription primer is hybridizable to the 5' terminal region of the padlock probe. In some embodiments, the reverse transcription primer comprises a functional moiety, wherein the DNA molecule is immobilized to the 3D matrix via the function moiety. In some embodiments, (b) comprises subjecting the RNA molecule to chemical degradation under a condition selected from the group consisting of a pH having value from 6 to 14, a temperature from 10° C. to 100° C., in the presence of a heavy metal ion, in the presence of a divalent cation, and any combination thereof.

In another aspect, the disclosure provides a method for processing a biological sample. In one embodiment, the method comprises: (a) providing the biological sample comprising a ribonucleic acid (RNA) molecule in a three-dimensional (3D) matrix, wherein the RNA molecule comprises a nucleic acid sequence; (b) hybridizing a primer to the RNA molecule, which primer does not include a functional moiety for immobilization to the matrix; (c) using a reverse transcriptase to reverse transcribe the RNA molecule by extending the primer to generate a complementary deoxyribonucleic acid (cDNA) molecule hybridized to the RNA molecule in the biological sample, which cDNA molecule comprises a functional moiety that immobilizes the cDNA molecule to the 3D matrix.

In some embodiments, the method further comprises degrading the RNA molecule hybridized to the cDNA molecule, to provide the cDNA molecule immobilized to the 3D matrix through the functional moiety, which cDNA molecule comprises an additional nucleic acid sequence that is a reverse complement of the nucleic acid sequence. In some embodiments, the RNA molecule comprises a functional moiety, wherein the RNA molecule is immobilized to the 3D matrix via the functional moiety.

In some embodiments, degrading comprises degrading the RNA molecule by a non-ribonuclease enzyme. In some embodiments, the non-ribonuclease enzyme is a reverse transcriptase or a DNA binding protein. In some embodiments, degrading comprises degrading the RNA molecule by a non-enzymatic reaction. In some embodiments, the non-enzymatic reaction is under a condition selected from the group consisting of a pH having value from 6 to 14, a temperature from 10° C. to 100° C., in the presence of a heavy metal ion, in the presence of a divalent cation, and any combination thereof.

In some embodiments, the method further comprises contacting the cDNA molecule with a probe. In some embodiments, the probe comprises a region that is not hybridizable with the cDNA molecule. In some embodiments, the probe is a padlock probe, wherein the padlock probe comprises 5' and 3' terminal regions complementary to the cDNA molecule, and hybridizing the 5' and 3' terminal regions of the padlock probe to the cDNA molecule. In some embodiments, the method further comprises circularizing the padlock probe by coupling two ends of the padlock probe together, to yield a circularized padlock probe, and detecting a nucleic acid sequence of the circularized padlock probe or a derivative thereof, thereby identifying the nucleic acid sequence of the RNA molecule. In some embodiments, the two ends of the padlock probe are contiguous. In some embodiments, the two ends of the padlock probe are separated by a gap region comprising at least one nucleotide. In some embodiments, the gap region comprises from 2 to 500 nucleotides. In some embodiments, the method further comprises filling the gap region by incorporating at least one nucleotide in an extension reaction. In some embodiments, the method further comprises filling the gap region by at least one additional nucleotide or an additional oligonucleotide sequence. In some embodiments, the additional oligonucleotide sequence is from 2 to 500 nucleotides in length. In some embodiments, the method further comprises subjecting the circularized padlock probe to rolling circle amplification (RCA) to generate an amplification product of a sequence of the circularized padlock probe, which amplification product comprises a nucleic acid sequence corresponding to the nucleic acid sequence of the RNA molecule. In some embodiments, the method further comprises detecting the nucleic acid sequence of the amplification product, thereby identifying the nucleic acid sequence of the RNA molecule. In some embodiments, the probe comprises a functional moiety, wherein the probe is immobilized to the 3D matrix via the functional moiety. In some embodiments, the functional moiety is directly conjugated on the probe. In some embodiments, the probe hybridizes to a tethering oligonucleotide comprising the functional moiety. In some embodiments, the tethering oligonucleotide hybridizes to the region of the probe that is not hybridizable to the cDNA molecule. In some embodiments, the method further comprises detecting a sequence of the probe or a derivative thereof, thereby identifying the nucleic acid sequence of the RNA molecule.

In some embodiments, (c) comprises using the reverse transcriptase to incorporate a nucleotide analog comprising the functional moiety into a growing strand, to yield the cDNA molecule comprising the nucleotide. In some embodiments, the nucleotide analog comprises amino-allyl dUTP, 5-TCO-PEG4-dUTP, C8-Alkyne-dUTP, 5-Azidomethyl-dUTP, 5-Vinyl-dUTP, 5-Ethynyl dUTP, or a combination thereof. In some embodiments, the method further comprises, subsequent to (b), modifying the primer or the cDNA molecule to include the functional moiety. In some embodiments, the primer is modified to include the functional moiety prior to generating the cDNA molecule. In some embodiments, the primer comprises a region that is not hybridizable to the RNA molecule, wherein the region hybridizes to an additional tethering oligonucleotide that comprises the functional moiety.

In some embodiments, (c) comprises attaching the functional moiety to the cDNA molecule through an enzymatic reaction or a non-enzymatic reaction. In some embodiments, the enzymatic reaction comprises using an enzyme to attach a nucleotide or an oligonucleotide having the functional moiety to the cDNA molecule. In some embodiments, the enzyme is a ligase, a polymerase, or a combination thereof. In some embodiments, the non-enzymatic reaction comprises attaching a chemical reagent having the functional moiety to the cDNA molecule by alkylation or oxymercuration. In some embodiments, the cDNA molecule further hybridizes to a tethering oligonucleotide having the functional moiety. In some embodiments, the tethering oligonucleotide hybridizes to the primer. In some embodiments, the 3D matrix further comprises an additional functional moiety, which additional functional moiety reacts with the function moiety of the cDNA molecule, thereby immobilizing the cDNA molecule.

Another aspect of the present disclosure provides a non-transitory computer readable medium comprising machine executable code that, upon execution by one or more computer processors, implements any of the methods above or elsewhere herein.

Another aspect of the present disclosure provides a system comprising one or more computer processors and computer memory coupled thereto. The computer memory comprises machine executable code that, upon execution by the one or more computer processors, implements any of the methods above or elsewhere herein.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
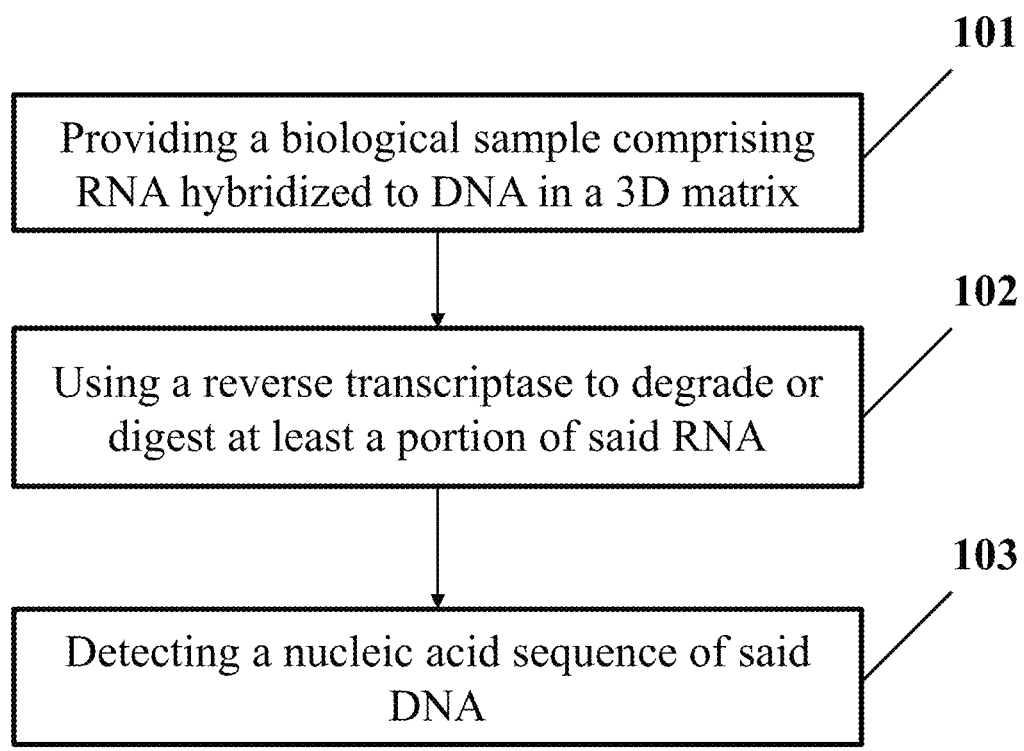
FIG. 1 shows an example of a method for identification of a nucleic acid sequence in a biological sample.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used in the specification and claims, the singular form "a", "an" or "the" includes plural references unless the context clearly dictates otherwise. For example, the term "a cell" includes a plurality of cells, including mixtures thereof.

As used herein, the terms "amplifying" and "amplification" generally refer to generating one or more copies (or "amplified product" or "amplification product") of a nucleic acid. The one or more copies may be generated by nucleic acid extension. Such extension may be a single round of extension or multiple rounds of extension. The amplified product may be generated by polymerase chain reaction (PCR).

The term "reverse transcription," as used herein, generally refers to the generation of deoxyribonucleic acid (DNA) from a ribonucleic acid (RNA) template via the action of a reverse transcriptase. Reverse transcription PCR (or RT-PCR) refers to reverse transcription coupled with PCR.

The term "nucleic acid," as used herein, generally refers to a polymeric form of nucleotides of any length. A nucleic acid may comprise either deoxyribonucleotides (dNTPs) or ribonucleotides (rNTPs), or analogs thereof. A nucleic acid may be an oligonucleotide or a polynucleotide. Nucleic acids may have any three-dimensional structure and may perform any function. Non-limiting examples of nucleic acids include DNA, RNA, coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant nucleic acids, branched nucleic acids, plasmids, vectors, isolated DNA of any sequence, isolated RNA of any sequence, nucleic acid probes, and primers. A nucleic acid may comprise one or more modified nucleotides, such as methylated nucleotides and nucleotide analogs. If present, modifications to the nucleotide structure may be made before or after assembly of the nucleic acid. The sequence of nucleotides of a nucleic acid may be interrupted by non-nucleotide components. A nucleic acid may be further modified after polymerization, such as by conjugation, with a functional moiety for immobilization.

As used herein, the term "subject," generally refers to an entity or a medium that has or may have testable or detectable genetic information. A subject can be a person or an individual. A subject can be a vertebrate, such as, for example, a mammal. Non-limiting examples of mammals include murines, simians, and humans. A subject may be an animal, such as a farm animal. A subject may be a pet, such as dog, cat, mouse, rat, or bird. Other examples of subjects include food, plant, soil, and water. A subject may be displaying or symptomatic with respect to a disease. As an alternative, the subject may be asymptomatic with respect to the disease.

Any suitable biological sample that comprises nucleic acid may be obtained from a subject. Any suitable biological sample that comprises nucleic acid may be used in the methods and systems described herein. A biological sample may be solid matter (e.g., biological tissue) or may be a fluid (e.g., a biological fluid). In general, a biological fluid can include any fluid associated with living organisms. Non-limiting examples of a biological sample include blood (or components of blood—e.g., white blood cells, red blood cells, platelets) obtained from any anatomical location (e.g., tissue, circulatory system, bone marrow) of a subject, cells obtained from any anatomical location of a subject, skin, heart, lung, kidney, breath, bone marrow, stool, semen, vaginal fluid, interstitial fluids derived from tumorous tissue, breast, pancreas, cerebral spinal fluid, tissue, throat swab, biopsy, placental fluid, amniotic fluid, liver, muscle, smooth muscle, bladder, gall bladder, colon, intestine, brain, cavity fluids, sputum, pus, micropiota, meconium, breast milk, prostate, esophagus, thyroid, serum, saliva, urine, gastric and digestive fluid, tears, ocular fluids, sweat, mucus, earwax, oil, glandular secretions, spinal fluid, hair, fingernails, skin cells, plasma, nasal swab or nasopharyngeal wash, spinal fluid, cord blood, emphatic fluids, and/or other excretions or body tissues. A biological sample may be a cell-free sample. Such cell-free sample may include DNA and/or RNA.

Overview

Provided herein are methods and systems for sample processing for use in target analysis or detection. Methods and systems of the present disclosure may be used for various applications, such as in situ sequencing or sequence identification (e.g., sequencing or sequence identification within a sample, such as, for example, a cell). In these methods and systems, probes may be used for target capture and subsequently for analysis or detection in the sample. Such probes may be padlock probes. Padlock probes can be designed or configured to bind specifically to targets. In some cases, padlock probes can be designed to hybridize with targets directly. In some other cases, padlock probes can be designed to bind the target indirectly by hybridizing with molecules derived from the targets. For example, in some applications in which ribonucleic acid (RNA) molecules are the targets, complementary deoxyribonucleic acid (cDNA) molecules can be synthesized from the RNA targets by reverse transcription, and the padlock probes can be designed to bind to the cDNA molecules. By hybridization to the cDNA molecule, the ends of the padlock probe are brought into juxtaposition for ligation. The ligation may be direct or indirect. In other words, the ends of the padlock probe may be ligated directly to each other or they may be ligated to an intervening nucleic acid molecule or a sequence of nucleotides. Thus, the terminal regions of the padlock probe may be complementary to adjacent, or contiguous, regions in the cDNA molecule synthesized from the RNA target molecule, or they may be complementary to non-adjacent or non-contiguous regions of the cDNA. In the cases where the padlock probe is complementary to non-adjacent or non-contiguous regions of the cDNA molecule, for ligation to occur, the "gap" between the two ends of the hybridized padlock probe can be filled by an intervening oligonucleotide molecule or a sequence of nucleotides.

Upon addition to a sample having a target molecule, the ends of the padlock probe may hybridize to complementary regions in a target molecule or derivative thereof (e.g., cDNA molecule). Following hybridization, the padlock probe may be circularized by direct or indirect ligation of the ends of the padlock probe by a ligase enzyme. The circularized padlock probe may be subjected to amplification to generate an amplification product. For example, the circulated padlock probe may be subjected to rolling circle amplification (RCA) to generate a DNA nanoball (i.e., rolony). The circularized padlock probe may be primed by the 3' end of the cDNA (i.e., the RCA is target-primed). A DNA polymerase with 3'-5' exonuclease activity may be used. This can permit the digestion of the cDNA strand in a 3'-5' direction to a point adjacent to the bound padlock probe. Alternatively, the cDNA may be of appropriate length and may act as the primer for the DNA polymerase-mediated amplification reaction without such digestion. As a further alternative, instead of priming the RCA with the cDNA molecule, an additional primer that can hybridize to the padlock probe may be added in the sample and used for amplification reaction.

The amplification product (e.g., rolony) can be used for the purpose of in situ (e.g., within a sample, such as, for example, a cell) molecular detection by fluorescent in situ sequencing (FISSEQ) in a biological sample, such as a cell or a tissue. The biological sample may comprise a three-dimensional matrix (3D matrix). The 3D matrix may be formed by subjecting the biological sample to a fixing agent, such as formaldehyde. The 3D matrix may also be formed by a matrix-forming material, such as polymerizable monomers or cross-linkable polymers. The amplification product can serve as an amplified sequencing template for FISSEQ, in which, for example, sequence features of the amplification product can be detected in situ by fluorescent sequencing, including but not limited to sequencing by synthesis (SBS), sequencing by ligation (SBL), or sequencing by hybridization (SBH). Using a plurality of padlock probes, a number of target nucleic acids can be detected in a multiplex manner.

Methods or systems utilizing a ligation reaction of a DNA-DNA duplex template formed between a cDNA molecule and a DNA padlock probe can be generally more efficient than methods or systems utilizing a ligation reaction of a DNA-RNA "hybrid" duplex template formed between an RNA molecule and a DNA padlock probe. This may be due to the enhanced efficiency of enzymatic ligation between DNA-DNA duplex templates compared to DNA-RNA hybrid duplex templates. Therefore, all or part of a target RNA molecule may be first converted into a cDNA molecule, such as by reverse transcription, prior to hybridization with the padlock probe. After generating the cDNA molecule, the RNA molecule can be degraded. Methods and systems provided herein use several methods to degrade RNA molecule. In some aspects, an enzymatic digestion of the RNA using a non-ribonuclease enzyme with ribonuclease activity is provided. In some other aspects, chemical decomposition of the RNA under conditions wherein cDNA remains substantially chemically stable is provided. In some cases, the target RNA molecule may directly hybridize to a padlock probe without prior reverse transcription.

Furthermore, in some applications, methods and systems for sample processing may preserve spatial information associated with each target molecule. Such spatial information may be preserved in a biological sample having a 3D matrix. To preserve the spatial information associated with each RNA molecule being detected in a padlock probe assay, the cDNA molecule can be spatially immobilized within the biological sample at the original position of the RNA molecule. In the present disclosure, several methods are provided to immobilize the cDNA molecule in a three-dimensional matrix.

Target

Provided herein are methods and systems for sample processing for use in target analysis or detection. The target may be an analyte of interest in a biological sample. In some cases, the target may be a nucleic acid target. In some cases, the target may be a protein. In the cases where the target is a protein, a binding agent which binds to the protein can be linked to a nucleic acid sequence which can then be detected by the methods and systems provided herein. For example, the binding agent can be a nucleic acid barcode conjugated antibody or antibody fragment. The nucleic acid target can be a ribonucleic acid (RNA) or a deoxyribonucleic acid (DNA). The nucleic acid target may be naturally occurring nucleic acids or non-naturally occurring nucleic acids, such as nucleic acids that have been made using synthetic methods.

The nucleic acid targets, whether naturally occurring or synthetic, can be present within a three-dimensional (3D) matrix and covalently attached to the 3D matrix such that the relative position of each nucleic acid is fixed (e.g., immobilized) within the 3D matrix. In this manner, a 3D matrix of covalently bound nucleic acids of any sequence can be provided. Each nucleic acid may have its own three-dimensional coordinates within the matrix material and each nucleic acid may represent information. In this manner, a large amount of information can be stored in a 3D matrix. Individual information-encoding nucleic acid target, such as DNA or RNA can be amplified and sequenced in situ (i.e., within the matrix), thereby enabling a large amount of information to be stored and read in a suitable 3D matrix. Naturally occurring nucleic acid targets can include endogenous DNAs and RNAs. Synthetic nucleic acid targets can include primers, barcodes, amplification products and probes. The synthetic nucleic acid targets may be derived from the endogenous nucleic acid molecules or include sequence information of the endogenous nucleic acid molecules. The synthetic nucleic acid targets can be used to capture endogenous nucleic acid targets to the 3D matrix and can be subsequently sequenced or detected to identity the sequence information and/or positional (or spatial) information of the endogenous nucleic acid molecules. For example, a synthetic nucleic acid target can be a primer having a poly-deoxythymine (dT) sequence, which can hybridize to an endogenous mRNA molecule. The primer may be immobilized to the 3D matrix and may be extended to include sequence information (e.g., a sequence) of the mRNA molecule. The extended primer can then be captured by padlock probes and amplified in situ for detection. In another example, a synthetic nucleic acid target can be a barcode conjugated on an antibody. The barcode may be captured by padlock probes and amplified in situ for detection.

The nucleic acid target can be an endogenous nucleic acid in a biological sample, for example, genomic DNA, messenger RNA (mRNA), ribosomal RNA (rRNA), transfer RNA (tRNA), microRNA (miRNA), small cytoplasmic RNA (scRNA), and small nuclear RNA (snRNA). The nucleic acid target may be a synthetic nucleic acid linked to a binding agent. The binding agent may bind to any biological molecules to be detected in a biological sample. For example, to detect a protein, the binding agent may be an antibody or a portion thereof having a nucleic acid sequence linked thereto. For another example, to detect a protein, the binding agent may be an aptamer.

The nucleic acid target may be amplified to produce amplification products or amplicons within the 3D matrix. The nucleic acid target may be amplified using nucleic acid amplification, such as, for example, polymerase chain reaction (PCR). The nucleic acid target may be bound to a probe and the probe may be subsequently amplified to produce amplification products or amplicons. In some cases, the nucleic acid target is a RNA target, and the RNA target may be reverse transcribed to generate a cDNA. The cDNA may then be subjected to amplification or may be contacted with a probe (e.g., a padlock probe). The probe can hybridize with the cDNA. In some cases, the nucleic acid target is a DNA target, and the DNA target can be subjected to amplification or can be contacted with a probe (e.g., a padlock probe). For example, the DNA target can be amplified directly by an amplification primer. For another example, a padlock probe may be contacted with the DNA target and hybridize to the DNA target. The padlock probe can then be circularized and amplified. The amplification products or amplicons can be attached to the matrix, for example, by copolymerization or cross-linking. This can result in a structurally stable and chemically stable 3D matrix of nucleic acids. The 3D matrix of nucleic acids may allow for prolonged information storage and read-out cycles. The nucleic acid/amplicon matrix may allow for high throughput sequencing of a wide-ranging array of samples in three dimensions.

Three-Dimensional Matrix

The present disclosure provides a three-dimensional (3D) matrix. The 3D matrix may comprise a plurality of nucleic acids. The 3D matrix may comprise a plurality of nucleic acids covalently or non-covalently attached thereto.

In some cases, a matrix-forming material may be used to form the 3D matrix. The matrix forming material may be polymerizable monomers or polymers, or cross-linkable polymers. The matrix forming material may be polyacrylamide, acrylamide monomers, cellulose, alginate, polyamide, agarose, dextran, or polyethylene glycol. The matrix forming materials can form a matrix by polymerization and/or crosslinking of the matrix forming materials using methods specific for the matrix forming materials and methods, reagents and conditions. The matrix forming material may form a polymeric matrix. The matrix forming material may form a polyelectrolyte gel. The matrix forming material may form a hydrogel gel matrix.

The matrix-forming material may form a 3D matrix including the plurality of nucleic acids while maintaining the spatial relationship of the nucleic acids. In this aspect, the plurality of nucleic acids can be immobilized within the matrix material. The plurality of nucleic acids may be immobilized within the matrix material by co-polymerization of the nucleic acids with the matrix-forming material. The plurality of nucleic acids may also be immobilized within the matrix material by crosslinking of the nucleic acids to the matrix material or otherwise cross-linking with the matrix-forming material. The plurality of nucleic acids may also be immobilized within the matrix by covalent attachment or through ligand-protein interaction to the matrix.

According to one aspect, the matrix can be porous thereby allowing the introduction of reagents into the matrix at the site of a nucleic acid for amplification of the nucleic acid. A porous matrix may be made according to various methods. For example, a polyacrylamide gel matrix can be co-polymerized with acrydite-modified streptavidin monomers and biotinylated DNA molecules, using a suitable acrylamide: bis-acrylamide ratio to control the cross-linking density. Additional control over the molecular sieve size and density can be achieved by adding additional cross-linkers such as functionalized polyethylene glycols.

According to one aspect, the 3D matrix may be sufficiently optically transparent or may have optical properties suitable for standard sequencing chemistries and deep three-dimensional imaging for high throughput information readout. Examples of the sequencing chemistries that utilize fluorescence imaging include ABI SoLiD (Life Technologies), in which a sequencing primer on a template is ligated to a library of fluorescently labeled octamers with a cleavable terminator. After ligation, the template can then be imaged using four color channels (FITC, Cy3, Texas Red and Cy5). The terminator can then be cleaved off leaving a free-end to engage in the next ligation-extension cycle. After all dinucleotide combinations have been determined, the images can be mapped to the color code space to determine the specific base calls per template. The workflow can be achieved using an automated fluidics and imaging device (i.e., SoLiD 5500 W Genome Analyzer, ABI Life Technologies). Another example of sequencing platform uses sequencing by synthesis, in which a pool of single nucleotide with a cleavable terminator can be incorporated using DNA polymerase. After imaging, the terminator can be cleaved and the cycle can be repeated. The fluorescence images can then be analyzed to call bases for each DNA amplicons within the flow cell (HiSeq, Illumina).

In some aspects, a biological sample may be fixed in the presence of the matrix-forming materials, for example, hydrogel subunits. By "fixing" the biological sample, it is meant exposing the biological sample, e.g., cells or tissues, to a fixation agent such that the cellular components become crosslinked to one another. By "hydrogel" or "hydrogel network" is meant a network of polymer chains that are water-insoluble, sometimes found as a colloidal gel in which water is the dispersion medium. In other words, hydrogels are a class of polymeric materials that can absorb large amounts of water without dissolving. Hydrogels can contain over 99% water and may comprise natural or synthetic polymers, or a combination thereof. Hydrogels may also possess a degree of flexibility very similar to natural tissue, due to their significant water content. By "hydrogel subunits" or "hydrogel precursors" refers to hydrophilic monomers, prepolymers, or polymers that can be crosslinked, or "polymerized", to form a 3D hydrogel network. Without being bound by any scientific theory, fixation of the biological sample in the presence of hydrogel subunits may crosslink the components of the biological sample to the hydrogel subunits, thereby securing molecular components in place, preserving the tissue architecture and cell morphology.

In some cases, the biological sample (e.g., cell) may be permeabilized or otherwise made accessible to an environment external to the biological sample. In some cases, the biological sample may be fixed and permeabilized first, and then a matrix-forming material can then be added into the biological sample.

Any convenient fixation agent, or "fixative," may be used to fix the biological sample in the absence or in the presence of hydrogel subunits, for example, formaldehyde, paraformaldehyde, glutaraldehyde, acetone, ethanol, methanol, etc. Typically, the fixative may be diluted in a buffer, e.g., saline, phosphate buffer (PB), phosphate buffered saline (PBS), citric acid buffer, potassium phosphate buffer, etc., usually at a concentration of about 1-10%, e.g. 1%, 2%, 3%, 4%, 5%, 6%, 7%, 8%, or 10%, for example, 4% paraformaldehyde/ 0.1M phosphate buffer; 2% paraformaldehyde/0.2% picric acid/0.1M phosphate buffer; 4% paraformaldehyde/0.2% periodate/1.2% lysine in 0.1 M phosphate buffer; 4% paraformaldehyde/0.05% glutaraldehyde in phosphate buffer; etc. The type of fixative used and the duration of exposure to the fixative will depend on the sensitivity of the molecules of interest in the specimen to denaturation by the fixative, and may be readily determined using conventional histochemical or immunohistochemical techniques.

The fixative/hydrogel composition may comprise any hydrogel subunits, such as, but not limited to, poly(ethylene glycol) and derivatives thereof (e.g. PEG-diacrylate (PEG-DA), PEG-RGD), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose and the like. Agents such as hydrophilic nanoparticles, e.g., poly-lactic acid (PLA), poly-glycolic acid (PLG), poly(lactic-co-glycolic acid) (PLGA), polystyrene, poly(dimethylsiloxane) (PDMS), etc. may be used to improve the permeability of the hydrogel while maintaining patternability. Materials such as block copolymers of PEG, degradable PEO, poly(lactic acid) (PLA), and other similar materials can be used to add specific properties to the hydrogel. Crosslinkers (e.g. bis-acrylamide, diazirine, etc.) and initiators (e.g. azobisisobutyronitrile (AIBN), riboflavin, L-arginine, etc.) may be included to promote covalent bonding between interacting macromolecules in later polymerization steps.

The biological sample (e.g., a cell or tissue) may be permeabilized after being fixed. Permeabilization may be performed to facilitate access to cellular cytoplasm or intracellular molecules, components or structures of a cell. Permeabilization may allow an agent (such as a phosphoselective antibody, a nucleic acid conjugated antibody, a nucleic acid probe, a primer, etc.) to enter into a cell and reach a concentration within the cell that is greater than that which would normally penetrate into the cell in the absence of such permeabilizing treatment. In some embodiments, cells may be stored following permeabilization. In some cases, the cells may be contacted with one or more agents to allow penetration of the one or more agent after permeabilization without any storage step and then analyzed. In some embodiments, cells may be permeabilized in the presence of at least about 60%, 70%, 80%, 90% or more methanol (or ethanol) and incubated on ice for a period of time. The period of time for incubation can be at least about 10, 15, 20, 25, 30, 35, 40, 50, 60 or more minutes.

In some embodiments, permeabilization of the cells may be performed by any suitable method. Selection of an appropriate permeabilizing agent and optimization of the incubation conditions and time may be performed. Suitable methods include, but are not limited to, exposure to a detergent (such as CHAPS, cholic acid, deoxycholic acid, digitonin, n-dodecyl-beta-D-maltoside, lauryl sulfate, glycodeoxycholic acid, n-lauroylsarcosine, saponin, and triton X-100) or to an organic alcohol (such as methanol and ethanol). Other permeabilizing methods can comprise the use of certain peptides or toxins that render membranes permeable. Permeabilization may also be performed by addition of an organic alcohol to the cells.

Permeabilization can also be achieved, for example, by way of illustration and not limitation, through the use of surfactants, detergents, phospholipids, phospholipid binding proteins, enzymes, viral membrane fusion proteins and the like; through the use of osmotically active agents; by using chemical crosslinking agents; by physicochemical methods including electroporation and the like, or by other permeabilizing methodologies.

Thus, for instance, cells may be permeabilized using any of a variety of known techniques, such as exposure to one or more detergents (e.g., digitonin, Triton X-100™, NP-40™, octyl glucoside and the like) at concentrations below those used to lyse cells and solubilize membranes (i.e., below the critical micelle concentration). Certain transfection reagents, such as dioleoyl-3-trimethylammonium propane (DOTAP), may also be used. ATP can also be used to permeabilize intact cells. Low concentrations of chemicals used as fixatives (e.g., formaldehyde) may also be used to permeabilize intact cells.

The nucleic acids (e.g., RNA molecule, cDNA molecule, primer, or probe) described herein may comprise a functional moiety. The nucleic acids can be linked to the 3D matrix by the functional moiety. The functional moiety can be reacted with a reactive group on the 3D matrix through conjugation chemistry. In some cases, the functional moiety can be attached to target of interest through conjugation chemistry. In some cases, the functional moiety can be directly attached to a reactive group on the native nucleic acid molecule. In some cases, the functional moiety can be indirectly linked to a target through an intermediate chemical or group. The conjugation strategies described herein are not limited to nucleic acid targets and can be used for protein or small molecule targets as well. A nucleotide analog comprising a functional moiety may be incorporated into a growing chain of the nucleic acid (e.g., cDNA molecule, probe, or primer) during nucleic acid synthesis or an extension reaction.

As used herein, the term "reactive group" or "functional moiety" means any moiety on a first reactant that is capable of reacting chemically with another functional moiety or reactive group on a second reactant to form a covalent or ionic linkage. "Reactive group" and "functional moiety" may be used interchangeably. For example, a reactive group of the monomer or polymer of the matrix-forming material can react chemically with a functional moiety (or another reactive group) on the substrate of interest or the target to form a covalent or ionic linkage. The substrate of interest or the target may then be immobilized to the matrix via the linkage formed by the reactive group and the functional moiety. Examples of suitable reactive groups or functional moieties include electrophiles or nucleophiles that can form a covalent linkage by reaction with a corresponding nucleophile or electrophile, respectively, on the substrate of interest. Non-limiting examples of suitable electrophilic reactive groups may include, for example, esters including activated esters (such as, for example, succinimidyl esters), amides, acrylamides, acyl azides, acyl halides, acyl nitriles, aldehydes, ketones, alkyl halides, alkyl sulfonates, anhydrides, aryl halides, aziridines, boronates, carbodiimides, diazoalkanes, epoxides, haloacetamides, haloplatinates, halotriazines, imido esters, isocyanates, isothiocyanates, maleimides, phosphoramidites, silyl halides, sulfonate esters, sulfonyl halides, and the like. Non-limiting examples of suitable nucleophilic reactive groups may include, for example, amines, anilines, thiols, alcohols, phenols, hyrazines, hydroxylamines, carboxylic acids, glycols, heterocycles, and the like.

The present disclosure provides a method of modifying a nucleic acid in situ to comprise a functional moiety. In some cases, the functional moiety may comprise a polymerizeable group. In some cases, the functional moiety may comprise a free radical polymerizeable group. In some cases, the functional moiety may comprise an amine, a thiol, an azide, an alkyne, a nitrone, an alkene, a tetrazine, a tetrazole, an acrydite or other click reactive group. In some cases, the functional moiety can be subsequently linked to a 3D matrix in situ. The functional moiety may further be used to preserve the absolute or relative spatial relationships among two or more molecules within a sample.

The biological sample within the 3D matrix may be cleared of proteins and/or lipids that are not targets of interest. For example, the biological sample can be cleared of proteins (also called "deproteination") by enzymatic proteolysis. The clearing step may be performed before or after covalent immobilization of any target molecules or derivatives thereof.

In some cases, the clearing step is performed after covalent immobilization of target nucleic acid molecules (e.g., RNA or DNA), primers (e.g., RT primers), derivatives of target molecules (e.g., cDNA or amplicons), probes (e.g., padlock probes) to a synthetic 3D matrix. Performing the clearing step after immobilization can enable any subsequent nucleic acid hybridization reactions to be performed under conditions where the sample has been substantially deproteinated, as by enzymatic proteolysis ("protein clearing"). This method can have the benefit of removing ribosomes and other RNA- or nucleic-acid-target-binding proteins from the target molecule (while maintaining spatial location), where the protein component may impede or inhibit primer binding, reverse transcription, or padlock ligation and amplification, thereby improving the sensitivity and quantitativity of the assay by reducing bias in probe capture events due to protein occupation of or protein crowding/proximity to the target nucleic acid.

The clearing step can comprise removing non-targets from the 3D matrix. The clearing step can comprise degrading the non-targets. The clearing step can comprise exposing the sample to an enzyme (e.g., a protease) able to degrade a protein. The clearing step can comprise exposing the sample to a detergent.

Proteins may be cleared from the sample using enzymes, denaturants, chelating agents, chemical agents, and the like, which may break down the proteins into smaller components and/or amino acids. These smaller components may be easier to remove physically, and/or may be sufficiently small or inert such that they do not significantly affect the background. Similarly, lipids may be cleared from the sample using surfactants or the like. In some cases, one or more of these agents are used, e.g., simultaneously or sequentially. Non-limiting examples of suitable enzymes include proteinases such as proteinase K, proteases or peptidases, or digestive enzymes such as trypsin, pepsin, or chymotrypsin. Non-limiting examples of suitable denaturants include guanidine HCl, acetone, acetic acid, urea, or lithium perchlorate. Non-limiting examples of chemical agents able to denature proteins include solvents such as phenol, chloroform, guanidinium isocyananate, urea, formamide, etc. Non-limiting examples of surfactants include Triton X-100 (polyethylene glycol p-(1,1,3,3-tetramethylbutyl)-phenyl ether), SDS (sodium dodecyl sulfate), Igepal CA-630, or poloxamers. Non-limiting examples of chelating agents include ethylenediaminetetraacetic acid (EDTA), citrate, or polyaspartic acid. In some embodiments, compounds such as these may be applied to the sample to clear proteins, lipids, and/or other components. For instance, a buffer solution (e.g., containing Tris or tris(hydroxymethyl)aminomethane) may be applied to the sample, then removed.

In some cases, nucleic acids that are not target of interest may also be cleared. These non-target nucleic acids may not be captured and/or immobilized to the 3D matrix, and therefore can be removed with an enzyme to degrade nucleic acid molecules. Non-limiting examples of DNA enzymes that may be used to remove DNA include DNase I, dsDNase, a variety of restriction enzymes, etc. Non-limiting examples of techniques to clear RNA include RNA enzymes such as RNase A, RNase T, or RNase H, or chemical agents, e.g., via alkaline hydrolysis (for example, by increasing the pH to greater than 10). Non-limiting examples of systems to remove sugars or extracellular matrix include enzymes such as chitinase, heparinases, or other glycosylases. Non-limiting examples of systems to remove lipids include enzymes such as lipidases, chemical agents such as alcohols (e.g., methanol or ethanol), or detergents such as Triton X-100 or sodium dodecyl sulfate. In this way, the background of the sample may be removed, which may facilitate analysis of the nucleic acid probes or other targets, e.g., using fluorescence microscopy, or other techniques as described herein.

Solid Support

A matrix may be used in conjunction with a solid support. For example, the matrix can be polymerized in such a way that one surface of the matrix is attached to a solid support (e.g., a glass surface, a flow cell, a glass slide, a well), while the other surface of the matrix is exposed or sandwiched between two solid supports. According to one aspect, the matrix can be contained within a container. In some cases, the biological sample may be fixed or immobilized on a solid support.

Solid supports of the present disclosure may be fashioned into a variety of shapes. In certain embodiments, the solid support is substantially planar. Examples of solid supports include plates such as slides, multiwell plates, flow cells, coverslips, microchips, and the like, containers such as microfuge tubes, test tubes and the like, tubing, sheets, pads, films and the like. Additionally, the solid supports may be, for example, biological, non-biological, organic, inorganic, or a combination thereof.

As used herein, the term "solid surface" is intended to mean the surface of a solid support or substrate and includes any material that can serve as a solid or semi-solid foundation for attachment of a biological sample or other molecules such as polynucleotides, amplicons, DNA balls, other nucleic acids and/or other polymers, including biopolymers. Example types of materials comprising solid surfaces include glass, modified glass, functionalized glass, inorganic glasses, microspheres, including inert and/or magnetic particles, plastics, polysaccharides, nylon, nitrocellulose, ceramics, resins, silica, silica-based materials, carbon, metals, an optical fiber or optical fiber bundles, a variety of polymers other than those exemplified above and multiwell plates. Specific types of exemplary plastics include acrylics, polystyrene, copolymers of styrene and other materials, polypropylene, polyethylene, polybutylene, polyurethanes and Teflon™. Specific types of exemplary silica-based materials include silicon and various forms of modified silicon.

Solid surfaces can also be varied in their shape depending on the application in a method described herein. For example, a solid surface useful in the present disclosure can be planar, or contain regions which are concave or convex.

Amplification

Any type of nucleic acid amplification reaction may be used to perform an amplification reaction in the methods or systems described herein and generate an amplification product. Moreover, amplification of a nucleic acid may be linear, exponential, or a combination thereof. Non-limiting examples of nucleic acid amplification methods include transcription (e.g., in vitro transcription), reverse transcription, primer extension, polymerase chain reaction, ligase chain reaction, helicase-dependent amplification, asymmetric amplification, rolling circle amplification, and multiple displacement amplification (MDA). In some cases, the amplified product may be DNA. In cases where a target RNA is amplified, DNA can be obtained by reverse transcription of the RNA and subsequent amplification of the DNA can be used to generate an amplified DNA product. In some cases, a target RNA is reverse transcribed by a reverse transcriptase to generate a cDNA. In some cases, a target DNA is transcribed by an RNA polymerase to generate an RNA. The amplified DNA product may be indicative of the presence of the target RNA in the biological sample. In cases where DNA is amplified, any DNA amplification method may be employed. Non-limiting examples of DNA amplification methods include polymerase chain reaction (PCR), variants of PCR (e.g., real-time PCR, allele-specific PCR, assembly PCR, asymmetric PCR, digital PCR, emulsion PCR, dial-out PCR, helicase-dependent PCR, nested PCR, hot start PCR, inverse PCR, methylation-specific PCR, miniprimer PCR, multiplex PCR, nested PCR, overlap-extension PCR, thermal asymmetric interlaced PCR, touchdown PCR), and ligase chain reaction (LCR). In some cases, DNA amplification is linear. In some cases, DNA amplification is exponential. In some cases, DNA amplification is achieved with nested PCR, which can improve sensitivity of detecting amplified DNA products.

The amplification of nucleic acid sequences may be performed within the matrix. Methods of amplifying nucleic acids may include rolling circle amplification in situ. In certain aspects, methods of amplifying nucleic acids may include the use of PCR, such as anchor PCR, RACE PCR, or a ligation chain reaction (LCR). Alternative amplification methods include but are not limited to self-sustained sequence replication, transcriptional amplification system, Q-Beta Replicase, recursive PCR or any other nucleic acid amplification method.

The nucleic acids within the 3D matrix may be contacted with reagents under suitable reaction conditions sufficient to amplify the nucleic acids. The matrix may be porous to allow migration of reagents into the matrix to contact the nucleic acids. In certain aspects, nucleic acids may be amplified by selectively hybridizing an amplification primer to an amplification site at the 3' end of a nucleic acid sequence using conventional methods. Amplification primers are 6 to 100, and even up to 1,000, nucleotides in length, but typically from 10 to 40 nucleotides, although oligonucleotides of different length are of use. In some cases, the amplification primer can be at least about 5, 6, 7, 8, 9, 10, 11, 12, 13, 14, 15, 16, 17, 18, 19, 20, 21, 22, 23, 24, 25, or more nucleotides in length. In some cases, the amplification primer can be at least about 20, 30, 40, 50, 60, 70, 80, 90, 100, 200, 300, 400, 500, or more nucleotides in length. Amplification primers may hybridize to a nucleic acid probe that hybridizes to a DNA molecule such that the amplification primers can be used to amplify a sequence of the nucleic acid probe. Amplification primers may be present in solution to be added to the matrix or they may be added during formation of the matrix to be present therein sufficiently adjacent to nucleic acids to allow for hybridization and amplification.

A DNA polymerase can be used in an amplification reaction. Any suitable DNA polymerase may be used, including commercially available DNA polymerases. A DNA polymerase generally refers to an enzyme that is capable of incorporating nucleotides to a strand of DNA in a template bound fashion. Non-limiting examples of DNA polymerases include Taq polymerase, Tth polymerase, Tli polymerase, Pfu polymerase, VENT polymerase, DEEP-VENT polymerase, EX-Taq polymerase, LA-Taq polymerase, Expand polymerases, Sso polymerase, Poc polymerase, Pab polymerase, Mth polymerase, Pho polymerase, ES4 polymerase, Tru polymerase, Tac polymerase, Tne polymerase, Tma polymerase, Tih polymerase, Tfi polymerase, Platinum Taq polymerases, Hi-Fi polymerase, Tbr polymerase, Tfl polymerase, Pfutubo polymerase, Pyrobest polymerase, Pwo polymerase, KOD polymerase, Bst polymerase, Sac polymerase, Klenow fragment, and variants, modified products and derivatives thereof. Other enzymes can also be used for an amplification reaction, including but not limited to, an RNA polymerase (e.g., T7 RNA polymerase, SP6 RNA polymerase, T3 RNA polymerase, etc.) and a reverse transcriptase (e.g., Avian myeloblastosis virus (AMV) reverse transcriptase, a wild type human immunodeficiency virus-1 (HIV-1) reverse transcriptase, or a Moloney Murine Leukemia Virus (M-MLV) reverse transcriptase).

Detection

The present disclosure provides methods and systems for sample processing for use in nucleic acid detection. A sequence of the nucleic acid target may be identified. Various methods can be used for nucleic acid detection, including hybridization and sequencing. Nucleic acid detection can comprise imaging the biological sample or the 3D matrix described herein.

Reporter agents may be linked with nucleic acids, including amplified products, by covalent or non-covalent interactions. Non-limiting examples of non-covalent interactions include ionic interactions, Van der Waals forces, hydrophobic interactions, hydrogen bonding, and combinations thereof. Reporter agents may bind to initial reactants and changes in reporter agent levels may be used to detect amplified product. Reporter agents may be detectable (or non-detectable) as nucleic acid amplification progresses. Reporter agents may be optically detectable. An optically-active dye (e.g., a fluorescent dye) may be used as a reporter agent. Non-limiting examples of dyes include SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin, phenanthridines and acridines, ethidium bromide, propidium iodide, hexidium iodide, dihydroethidium, ethidium homodimer-1 and -2, ethidium monoazide, and ACMA, Hoechst 33258, Hoechst 33342, Hoechst 34580, DAPI, acridine orange, 7-AAD, actinomycin D, LDS751, hydroxystilbamidine, SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red), fluorescein, fluorescein isothiocyanate (FITC), tetramethyl rhodamine isothiocyanate (TRITC), rhodamine, tetramethyl rhodamine, R-phycoerythrin, Cy-2, Cy-3, Cy-3.5, Cy-5, Cy5.5, Cy-7, Texas Red, Phar-Red, allophycocyanin (APC), Sybr Green I, Sybr Green II, Sybr Gold, CellTracker Green, 7-AAD, ethidium homodimer I, ethidium homodimer II, ethidium homodimer III, ethidium bromide, umbelliferone, eosin, green fluorescent protein, erythrosin, coumarin, methyl coumarin, pyrene, malachite green, stilbene, lucifer yellow, cascade blue, dichlorotriazinylamine fluorescein, dansyl chloride, fluorescent lanthanide complexes such as those including europium and terbium, carboxy tetrachloro fluorescein, 5 and/or 6-carboxy fluorescein (FAM), 5- (or 6-) iodoacetamidofluorescein, 5-{[2 (and 3)-5-(Acetylmercapto)-succinyl]amino}fluorescein (SAMSA-fluorescein), lissamine rhodamine B sulfonyl chloride, 5 and/or 6 carboxy rhodamine (ROX), 7-amino-methyl-coumarin, 7-Amino-4-methylcoumarin-3-acetic acid (AMCA), BODIPY fluorophores, 8-methoxypyrene-1,3,6-trisulfonic acid trisodium salt, 3,6-Disulfonate-4-amino-naphthalimide, phycobiliproteins, AlexaFluor 350, 405, 430, 488, 532, 546, 555, 568, 594, 610, 633, 635, 647, 660, 680, 700, 750, and 790 dyes, DyLight 350, 405, 488, 550, 594, 633, 650, 680, 755, and 800 dyes, or other fluorophores.

In some embodiments, a reporter agent may be a sequence-specific oligonucleotide probe that is optically active when hybridized with a nucleic acid target or derivative thereof (e.g., an amplified product). A probe may be linked to any of the optically-active reporter agents (e.g., dyes) described herein and may also include a quencher capable of blocking the optical activity of an associated dye. Non-limiting examples of probes that may be useful used as reporter agents include TaqMan probes, TaqMan Tamara probes, TaqMan MGB probes, or Lion probes.

In some aspects, the method for determining the nucleic acid sequence of a target nucleic acid molecule includes sequencing. In some aspects, sequencing by synthesis, sequencing by ligation or sequencing by hybridization is used for determining the nucleic acid sequence of a target nucleic acid molecule. As disclosed herein, various amplification methods can be employed to generate larger quantities, particularly of limited nucleic acid samples, prior to sequencing. For example, the amplification methods can produce a targeted library of amplicons.

For sequencing by ligation, labeled nucleic acid fragments may be hybridized and identified to determine the sequence of a target nucleic acid molecule. For sequencing by synthesis (SBS), labeled nucleotides can be used to determine the sequence of a target nucleic acid molecule. A target nucleic acid molecule can be hybridized with a primer and incubated in the presence of a polymerase and a labeled nucleotide containing a blocking group. The primer can be extended such that the labeled nucleotide is incorporated. The presence of the blocking group may permit the incorporation of a single nucleotide. The presence of the label can permit identification of the incorporated nucleotide. As used herein, a label can be any optically active dye described herein. Either single bases can be added or, alternatively, all four bases can be added simultaneously, particularly when each base is associated with a distinguishable label. After identifying the incorporated nucleotide by its corresponding label, both the label and the blocking group can be removed, thereby allowing a subsequent round of incorporation and identification. Thus, cleavable linkers can link the label to the base. Examples of cleavable linker include, but are not limited to, peptide linkers. Additionally, a removable blocking group may be used so that multiple rounds of identification can be performed, thereby permitting identification of at least a portion of the target nucleic acid sequence. The compositions and methods disclosed herein are useful for such an SBS approach. In addition, the compositions and methods can be useful for sequencing from a solid support (e.g., an array or a sample within a 3D matrix as described herein), where multiple sequences can be "read" simultaneously from multiple positions on the solid support since each nucleotide at each position can be identified based on its identifiable label. Example methods are described in US 2009/0088327; US 2010/0028885; and US 2009/0325172, each of which is incorporated herein by reference.

RNA Degradation

The methods and systems described herein may use a probe for target capture or detection. For example, the probe may be a padlock probe. In the padlock probe capture method, a ligation reaction of a DNA-DNA duplex template formed between a cDNA molecule and the DNA padlock probe can be generally more efficient than a ligation reaction of a DNA-RNA "hybrid" duplex template formed between an RNA molecule and DNA padlock probe, due to the enhanced efficiency of enzymatic ligation between DNA-DNA duplex templates compared to DNA-RNA hybrid duplex templates. Therefore, all or part of a target RNA molecule may be first converted into a cDNA molecule, as by reverse transcription, prior to the capture of target molecule by the padlock probe. In some cases, the padlock probe may be extended via a DNA polymerization reaction, using the cDNA molecule as a template, until the 3' and 5' ends of the padlock probe are proximal for the ligation reaction to occur.

After converting all or part of a target RNA molecule into a cDNA molecule, the RNA molecule may be degraded. In some cases, the RNA may be degraded using a non-ribonuclease enzyme with RNA catalytic cleavage activity. In some other cases, the RNA may be degraded by chemical decomposition under conditions wherein cDNA can remain substantially chemically stable.

In some cases, a target RNA molecule may be directly captured by (e.g., hybridized to) a DNA padlock probe without reverse transcription step. In this case, the padlock probe may be extended using the target RNA molecule as a template or may be circularized while the padlock probe hybridized to the target RNA molecule. The target RNA molecule can then be degraded after circularization of the padlock probe.

Reverse Transcriptases

The RNA molecule may be enzymatically digested via a non-ribonuclease enzyme. According to a certain embodiment, the enzymatic digestion of the RNA molecule can be catalyzed by a reverse transcriptase. Certain reverse transcriptases may possess ribonuclease activity, including but not limited to RNaseH activity. Certain reverse transcriptases may possess the activity of specifically digesting RNA within an RNA-DNA hybrid duplex. For example, Avian myeloblastosis virus (AMV) reverse transcriptase possesses an intrinsic RNase H activity, which can degrade the RNA strand of an RNA/DNA hybrid. Other reverse transcriptases exhibiting ribonuclease activity or RNA catalytic cleavage activity include but are not limited to the wild type HIV-1 and M-MLV reverse transcriptases.

Most reverse transcriptases may not possess ribonuclease activity or RNA catalytic cleavage activity, thereby enhancing the rate of full-length cDNA synthesis. For example, the most popular variant of M-MLV RT is the M-MLV RT RNase H-point mutant, which has a single amino acid substitution that dramatically reduces RNase H activity. However, for the purpose of padlock probe assay as described herein, the reverse transcription reaction may be primed, either specifically by using a substantially complementary primer, or non-specifically, by using a pool of degenerate primers, proximal to the padlock probe capture site along the RNA/cDNA molecule, in which case full-length cDNA synthesis may not be needed for efficient padlock probe capture.

Using a reverse transcriptase to degrade or digest RNA may provide cost and time savings compared to using a separate enzymatic reaction for RNA digestion. The methods described herein may also reduce the number of components and/or steps in a padlock probe assay. Furthermore, using this strategy the ribonuclease activity of the reverse transcriptase may be modulated by varying the composition of the reaction buffer to enable a multi-phase reaction comprising a first phase of efficient reverse transcription, and a subsequent phase of efficient RNA digestion. Aspects of reaction buffer composition modulating ribonuclease activity may include ribonuclease inhibitors, including organic chemicals and polypeptides, cofactors including metal ions, such as $Mg^{2+}$, $Mn^{2+}$, $Na^{1+}$, ATP, NADPH, etc. For example, reverse transcription by HIV-1 RTase may proceed efficiently under low concentrations of Mg2+ ions, despite strongly reduced intrinsic polymerase activity, by decreasing the degradation of RNA template by the RNase activity, while subsequently increasing the concentration of $Mg^{2+}$ can increase the ribonuclease activity to liberate the cDNA from the hybrid duplex.

DNA Binding Proteins

According to another aspect of the present disclosure, the RNA can be digested by another non-ribonuclease enzyme possessing ribonuclease activity or RNA catalytic cleavage activity. In a particular embodiment, a DNA binding protein with ribonuclease activity or RNA catalytic cleavage activity may be used for dual purposes. One of the purposes may be digestion of the RNA molecule. One such other purpose may be stabilization of the single-stranded cDNA molecule, such as by a single-stranded DNA (ssDNA) binding protein. The DNA binding protein may also promote hybridization between the cDNA molecule and the DNA padlock probe molecule. For example, the DNA binding protein Sso7d can be used to promote the annealing of complementary DNA strands above the melting point of the duplex, and may also be used to degrade RNA since Sso7 possesses ribonuclease activity.

Chemical Decomposition

The RNA can be subjected to chemical decomposition under conditions wherein cDNA remains substantially chemically stable. RNA hydrolysis may be a reaction in which a phosphodiester bond in the sugar-phosphate backbone of RNA is broken, cleaving the RNA molecule. RNA can be susceptible to this base-catalyzed hydrolysis because the ribose sugar in RNA has a hydroxyl group at the 2' position. This feature may make RNA chemically unstable compared to DNA, which does not have this 2' OH group and thus may not be susceptible to base-catalyzed hydrolysis. Chemical decomposition of RNA, such as by hydrolysis, may occur under a variety of conditions under which DNA including single-stranded cDNA can remain substantially chemically stable. RNA may be thermolabile and susceptible to metal-catalyzed degradation. Under normal conditions RNA hydrolysis can occur at a low frequency, but RNA hydrolysis can be accelerated under certain conditions, for example, acidic pH, alkaline pH, high temperatures, in the presence of divalent cations, and in the presence of heavy metal ions.

A buffer may be used to provide a condition for chemical decomposition of the RNA. For example, a buffer can comprise Tris HCL with a pH of at least about 7, 7.5, 8, or more. The final concentration of Tris HCL can be at least about 20, 30, 40, 50, or more mM. The buffer can further comprise MgCL$_2$ with a final concentration of at least about 15, 20, 25, 30, 35, 40, 45, 50, or more mM. In some cases, the buffer comprises 50 mM Tris HCL with a pH of 7.5-8 and 20-50 mM MgCL$_2$. For another example, a buffer can comprise sodium borate with a pH of at least about 7, 7.5, 8, or more. The final concentration of sodium borate can be at least about 20, 30, 40, 50, or more mM. The buffer can further comprise MgCL$_2$ with a final concentration of at least about 15, 20, 25, 30, 35, 40, 45, 50, or more mM. In some cases, the buffer comprises 50 mM Sodium Borate at pH 7.5-8 with 20-50 mM MgCl$_2$. The divalent cation may not be limited to Mg$^{2+}$, and can be other types of divalent cations such as Mn$^{2+}$.

The buffer used for chemical decomposition of RNAs may also catalyze a click reaction between click reactive groups. In some cases, a molecule (e.g., a target, a primer, a probe, or a molecule derived from a target such as cDNA) may be tethered via a click reaction to a click reactive group functionalized hydrogel matrix (e.g., click gel). For example, the 5'azidomethyl-dUTP can be incorporated into cDNA and then immobilized to the hydrogel matrix functionalized with alkyne groups. Various click reactions may be used. The buffer described herein can both catalyze the functional immobilization linkage between the molecule and the matrix and hydrolyze the RNA molecule, liberating the DNA from the DNA-RNA hybrid duplex. Using the buffer having both functions in chemical deposition and click reaction catalyzation may provide an improvement in workflow efficiency, reduce workflow time, and reduce the number of assay reagents. For example, the buffer may be a Cu(I)-catalyzed alkyne-azide cycloaddition (abbreviated as CUAAC) click reaction catalyzing buffer, which catalyzes the alkyne-azide bond in the click reaction. The buffer can comprise 1-25 mM copper (II) sulfate solution, 1-50 mM Tris((1-hydroxy-propyl-1H-1,2,3-triazol-4-yl)methyl)amine (abbreviated as THPTA) solution, 5-100 mM 4-(2-hydroxyethyl)-1-piperazineethanesulfonic acid (abbreviated as HEPES) buffer, and 5-100 mM L-ascorbic acid. In some cases, the copper (II) sulfate may be at a final concentration of at least about 1, 5, 10, 15, 20, 25, or more mM. In some cases, the THPTA may be at a final concentration of at least about 1, 5, 10, 15, 20, 25, 30, 35, 40, 45, 50, or more mM. In some cases, the HEPES may be at a final concentration of at least about 2, 5, 10, 15, 20, 25, 30, 35, 40, 45, 50, 55, 60, 65, 70, 75, 80, 85, 90, 95, 100, or more mM. In some cases, the L-ascorbic acid may be at a final concentration of at least about 2, 5, 10, 15, 20, 25, 30, 35, 40, 45, 50, 55, 60, 65, 70, 75, 80, 85, 90, 95, 100, or more mM. Optionally, the buffer may be degassed or argon bubbled to remove dissolved oxygen prior to use.

Using the RNA degradation methods described herein may provide cost and time savings and improve the efficiency of the liberation of the cDNA from the hybrid duplex. The chemical decomposition of RNA can be faster and more efficient than enzymatic digestion. Moreover, the chemical non-enzymatic reagents may be cheaper, easier to synthesize, easier to store, and have longer shelf life compared to reagents used in enzymatic reactions.

Nucleic Acid Immobilization in a 3D Matrix

To preserve the spatial information associated with each RNA molecule being detected in the padlock probe assay, the cDNA molecule within the biological sample (e.g., cell and tissue) may be spatially immobilized at the original position of the RNA molecule. Similarly, in the case of directly capturing target RNA or DNA molecule by a probe (e.g., a padlock probe), the probe may be spatially immobilized at the original position of the target RNA or DNA molecule. The spatial origin of the target RNA or DNA molecule itself may be typically preserved by the formation of chemical or physical crosslinks between the target RNA or DNA molecule and the naturally-occurring 3D matrix of biomolecules (e.g., proteins) within the biological sample. The chemical or physical crosslinks can be formed by temperature, electromagnetic radiation (e.g., microwave), or chemicals such as formaldehyde and glutaraldehyde and others within the cell and tissue. The naturally-occurring 3D matrix may be formed by crosslinking endogenous or native biomolecules, such as proteins and nucleic acids, within a cell or tissue. The spatial origin of the RNA molecule may also be preserved by the formation of chemical or physical crosslinks between the RNA molecule and other natural or synthetic components added to the sample to supplement or replace native cellular components for the purpose of immobilizing the cDNA. For example, a synthetic 3D matrix may be formed in situ throughout the cell and tissue sample in order to preserve a spatial position of the RNA molecule or DNA molecule. The synthetic 3D matrix can be a hydrogel matrix. For example, the 3D matrix may be composed of polyacrylamide or polyethylene glycol (PEG). During cDNA synthesis, the spatial location of the cDNA can be preserved via hydrogen bonding between the RNA and cDNA within the hybrid duplex ("hybridization"). However, the spatial location of the cDNA independent of the RNA molecule can be preserved, for example, to avoid the loss of spatial position after liberation of the cDNA from the hybrid RNA-DNA duplex.

The functional moiety can bind to or react with a cell or cellular component. The affinity binding group can bind to a cell or cellular component. The functional moiety may comprise at least one nucleotide modified with biotin, an amine group, a lower alkylamine group, an acetyl group, DMTO, fluoroscein, a thiol group, or acridine. In the case a synthetic 3D matrix is provided for cDNA cross-linking, the sample may be immersed in a gel solution which upon polymerization can give rise to a gel matrix to which the cDNA molecule or target RNA molecule can be attached. As described herein, approaches to immobilize nucleic acid molecules in a matrix are provided.

Immobilization of cDNA Molecules

Approaches to immobilizing the cDNA molecule independently of its hybridization to the RNA are provided. Generically, these advances can fall into three categories: a) the in situ polymerized component of the cDNA can comprise the functional moiety for immobilization; b) the functional moiety for immobilization can react with a pre-existing (at the time of reverse transcription) in situ matrix of non-cellular origin, i.e. a synthetic or exogenous matrix; and c) the functional immobilization moiety can be associated with the reverse transcription primer by hydrogen bonding via DNA hybridization.

According to the first aspect, the in situ polymerized component of the cDNA can comprise the functional moiety for immobilization, rather than the primer from which reverse transcription is initiated, or primed.

The cDNA molecule may be functionalized during the reverse transcription reaction, such as by adding nucleotide triphosphate analogs comprising functional moieties for immobilization. Such nucleotide triphosphate analogs include, but are not limited to, amino-allyl dUTP, 5-TCO-PEG4-dUTP, C8-Alkyne-dUTP, 5-Azidomethyl-dUTP, 5-Vinyl-dUTP, 5-Ethynyl dUTP, and other nucleotide triphosphate analogs comprising a functional moiety for cDNA immobilization by cross-linking, or forming a chemical bond between the cDNA and in situ matrix, cellular or synthetic. Furthermore, the in situ matrix, cellular or synthetic, may contain or be made to contain chemical moieties (e.g., reactive groups) that can react with the functional moieties in the cDNA through functionalization reactions. For example, amino-allyl dUTP may be cross-linked to endogenous free amine groups present in proteins and other biomolecules present within the endogenous or exogenous cellular matrix, or present in a modified synthetic hydrogel matrix, such as an amine-functionalized polyacrylamide hydrogel formed by copolymerization of polyacrylamide and N-(3-aminopropyl)-methacrylamide; likewise nucleoside analogs containing azide functional moieties may be cross-linked to a synthetic hydrogel matrix comprising alkyne functional moieties, such as that formed by copolymerization of acrylamide and propargyl acrylamide.

The cDNA molecule may be functionalized with moieties for immobilization subsequent to reverse transcription. Mechanisms for post-synthesis cDNA functionalization may include a variety of biochemical and chemical methods. These include, but are not limited to, use of a ligation reaction to conjugate an oligonucleotide bearing a functional moiety for immobilization to the cDNA molecule, use of a DNA polymerization reaction to add templated or un-templated bases to the cDNA, as in the process of A-tailing by Taq polymerize, or by using the reactions mediated by DNA end-repair mechanisms. Alternatively, a chemical method of DNA chemical functionalization may be used to conjugate functional moieties for immobilization. For example, Label-IT Amine and Label-X are bifunctional reagents that can react with nucleic acids via a nitrogen mustard alkylation mechanism for the purpose of conjugating free amine or acryloyl groups to the nucleic acid, which can be used for the purpose of immobilization to the matrix. Other chemistries, including but not limited to, DNA alkylation and oxymercuration, can provide mechanisms for functionalizing DNA.

The approaches for cDNA immobilization provided herein provide several advantages. For example, using the approaches provided herein, unmodified DNA oligonucleotides may be used as reverse transcription primers, simplifying the manufacturing of these reagents and reducing assay cost. Furthermore, by restricting cross-linking functional moieties to newly polymerized components of the cDNA, residual reverse transcription primers which have not participated in a reverse transcription reaction may be easily washed out of the sample and cannot participate in the cDNA immobilization mechanism, which may reduce background signals or improve downstream reaction yields. In addition, using a separate reaction to functionalize the cDNA with functional moieties after reverse transcription may simplify experimental workflows. For example, a DNA functionalization mechanism can be used to simultaneously functionalize cDNA and genomic DNA with functional moieties in a single reaction, facilitating multi-omic in situ assays such as fluorescent in situ sequencing (FISSEQ).

The functional moiety for immobilization may react or cross-link with a pre-existing (at the time of reverse transcription) in situ matrix of non-cellular origin, i.e. a synthetic or exogenous matrix. According to this aspect, a synthetic chemical matrix bearing functional moieties for cDNA immobilization may be formed in situ prior to reverse transcription. Suitable functional moieties include but are not limited to amine and click functional groups. After synthesis of the cDNA molecule, functional moieties present in the cDNA can cross-link with complementary functional moieties with the matrix. By using a pre-formed in situ synthetic matrix for immobilization, all or part of the natural biological matrix of the sample may be degraded, removed, or chemically modified, thereby enhancing the reaction properties, including yield, of the reverse transcription or other reactions.

Modification of Primers

The reverse transcription primer itself may bear no functional moieties for immobilization, but instead may be associated with one or more functional moieties for cDNA immobilization via hydrogen bonding. This approach may enable the use of unmodified reverse transcription primers, thereby simplifying and reducing the cost of assay manufacturing. For example, the primers may bear a functional domain, such as a common domain among a plurality of reverse transcription primers, comprising a tethering oligonucleotide hybridization site, and the tethering oligonucleotide can bear the functional moiety for cDNA immobilization. Furthermore, the tethering oligonucleotide may bear additional features, such as partial complementarity to the domains responsible for binding the RNA and initiating reverse transcription. The tethering oligonucleotide may bear additional sequence used for enhancing the specificity of the reverse transcription primer-cDNA annealing reaction via competitive hybridization mechanisms.

In some other cases, a primer (e.g., a reverse transcription primer) may comprise a functional moiety for immobilization onto the 3D matrix. For example, a primer may not hybridize to a tethering oligonucleotide having a functional moiety, but instead can be directly covalently linked to a functional moiety for immobilization.

Modification of Padlock Probes

The padlock probe may comprise functional moieties for immobilization to the in situ matrix, either directly or indirectly, as via a hybridized oligonucleotide. For example, a tethering oligonucleotide hybridized to the backbone of the padlock probe, e.g., outside the domains responsible for hybridizing to the target cDNA molecule, may serve as a rolling circle amplification primer, thereby serving to tether the padlock probe molecule (and cDNA molecule) via DNA hybridization prior to rolling circle amplification, and subsequently serving to tether the rolling circle amplicon (i.e., rolony) after rolling circle amplification for the purpose of preserving the spatial information associated with the original RNA molecule, cognate cDNA molecule, padlock probe, and rolony.

In some cases, the efficiency, or reaction yield, of establishing the functional immobilization linkage between the target molecule, probe, cDNA, padlock probe, or amplicon to the 3D matrix can be enhanced by the presence of more than one functional moiety within a molecule to be tethered. In the case of functional moiety incorporation into the cDNA during reverse transcription, this is accomplished by titrating the amount of functionally modified dNTP in the mix. In some embodiments, where a tethering oligonucleotide is used to indirectly immobilize the target or probe by hydrogen bonding provided by DNA hybridization, tethering oligonucleotides bearing multiple functional moieties can be synthesized. For example, tethering oligonucleotide bearing multiple functional moieties can be synthesized by incorporation of internal amines during chemical DNA synthesis, and subsequent conversion (e.g., en masse conversion) of amines to azide, acryloyl, or other functional moieties. The conversion can be achieved by amine-reactive chemical groups such as NHS-esters. The inefficiency of single-molecule tethering to the 3D matrix using a single tethering moiety may result from either intrinsic rate of the immobilization reaction (i.e., the chance an acryloyl is incorporated into the in situ polymerizing matrix, or the chance of an azide coming into proximity to the alkyne present in the click gel), or due to "non-ideal" in situ matrix synthesis processes. For example, the "non-ideal" in situ matrix synthesis process can refer to the situation where the single molecule is conjugated to a polymer, but that polymer is not itself stably linked into the larger emergent 3D network architecture generated during formation of the 3D matrix, which merely increases the molecular weight of the molecule but still allows the molecule and the conjugated polymer thereof to diffuse from the 3D matrix. The presence of a plurality of immobilization moieties can mitigate both of these mechanisms by increasing the chance a single molecule is incorporated as the sum total or product of likelihood of each moiety incorporation reaction, and also by providing the potential for linkage to multiple polymer chains within the 3D matrix. These multiple functional moieties may be in close proximity, or alternatively, spaced at regular or irregular intervals within the molecule. For example, multiple functional moieties can be present consecutively within a nucleic acid molecule. For example, multiple functional moieties can be separated by at least 1, 2, 3, 4, 5, 6, 7, or more nucleotides within a nucleic acid molecule.

Methods for Sample Processing

In an aspect, the present disclosure provides a method for identification of a nucleic acid sequence in a biological sample. The method may comprise providing the biological sample comprising a ribonucleic acid (RNA) molecule hybridized to a deoxyribonucleic acid molecule (DNA) in a three-dimensional (3D) matrix. The RNA molecule may comprise the nucleic acid sequence. Next, a reverse transcriptase or a functional derivative thereof may be used to degrade or digest at least a portion of the RNA molecule hybridized to the DNA molecule. The DNA molecule may comprise an additional nucleic acid sequence that is a reverse complement of the nucleic acid sequence. Next, the additional nucleic acid sequence in the biological sample may be detected, thereby identifying the nucleic acid sequence.

The DNA molecule may be a complementary deoxyribonucleic acid (cDNA) molecule. For example, the DNA molecule may be reverse transcribed from the RNA molecule. The cDNA molecule may be reverse transcribed from the RNA molecule and amplified (e.g., by polymerase chain reaction (PCR)) through one or more rounds of amplification to generate one or more copies of a sequence of the cDNA molecule.

In some cases, an additional reverse transcriptase or functional derivative thereof may be used to reverse transcribe the RNA molecule to generate the DNA molecule hybridized to the RNA molecule in the biological sample. As an alternative, the reverse transcriptase or functional derivative thereof, which was used to degrade or digest at least a portion of the RNA molecule, may be used to initially reverse transcribe the RNA molecule to generate the DNA molecule hybridized to the RNA molecule in the biological sample.

The DNA molecule may be immobilized to the 3D matrix. For example, the DNA molecule may be covalently immobilized to the 3D matrix (e.g., by cross-linking, such as using disulfide bonds). The DNA molecule may comprise a functional moiety, and the DNA molecule may be immobilized to the 3D matrix via the functional moiety. Examples of functional moiety include but are not limited to an amine, acrydite, alkyne, biotin, azide, and thiol. The RNA molecule may be immobilized to the 3D matrix. The RNA molecule may comprise a functional moiety, and the RNA molecule may be immobilized to the 3D matrix via the functional moiety. For example, the RNA molecule may be modified with LabelX which can be used to covalently attach the RNA molecule to the 3D matrix. The compound LabelX can be synthesized from Acryloyl-X SE (6-((acryloyl)amino) hexanoic acid, succinimidyl ester) and Label-IT amine (MirusBio) using NHS-ester chemistry and can react with RNA, for example, with the N7 position of guanines. The LabelX reagent can enable development of other attachment chemistries beside free-radical polymerization of acryloyl into polyacrylamide. For example, an NHS-ester-azide compound may be conjugated to Label-IT Amine to create a new linker capable of tethering nucleic acids into a PEG-click hydrogel matrix.

In some cases, a matrix-forming material may be used to form the 3D matrix. The matrix forming material may be polymerizable monomers or polymers, or cross-linkable polymers. The matrix forming material may be polyacrylamide, acrylamide monomers, cellulose, alginate, polyamide, agarose, dextran, or polyethylene glycol. The matrix forming materials can form a matrix by polymerization and/or crosslinking of the matrix forming materials using methods specific for the matrix forming materials and methods, reagents and conditions. The matrix forming material may form a polymeric matrix. The matrix forming material may form a polyelectrolyte gel. The matrix forming material may form a hydrogel gel matrix.

In some cases, the cDNA molecule may be contacted with a probe. The cDNA molecule may hybridize to the probe. The probe may comprise a functional moiety. The probe may be immobilized to the 3D matrix via the functional moiety. The cDNA molecule can be indirectly immobilized to the 3D matrix via the functional moiety by hybridizing to the probe. The functional moiety can bind to or react with a cell or cellular component, or can be an affinity binding group capable of binding to a cell or cellular component. The functional moiety may comprise at least one nucleotide modified with biotin, an amine group, a lower alkylamine group, an acetyl group, DMTO, fluoroscein, a thiol group, or acridine. The probe may be a padlock probe, wherein the padlock probe comprises 5' and 3' terminal regions complementary to the cDNA molecule. The 5' and 3' terminal regions of the padlock probe can be hybridized to the cDNA molecule. After hybridizing with the cDNA molecule, the 5' and 3' ends can be brought into juxtaposition. The two ends of the padlock probe may be contiguous or separated by a gap region of the cDNA molecule. The gap region may be of various lengths. For example, the gap region can comprise at least 1, at least 5, at least 10, at least 15, at least 20, at least 25, at least 30, at least 35, at least 40, at least 45, or at least 50 nucleotide(s). For another example, the gap region can comprise from 2 to 10, from 10 to 20, from 20 to 50, from 50 to 100, from 100 to 150, from 150 to 200, from 200 to 300, from 300 to 400, or from 400 to 500 nucleotides. A circularized padlock probe can be generated by ligating two ends of the padlock probe together. In the cases where the two ends are contiguous, the two ends can be ligated directly. In the cases where the two ends are separated by a gap region, the gap region can be filled in before ligation. The gap region can be filled in by incorporating one or more nucleotides in an extension reaction, for example, by extending from the 3' end of the two ends. The extension reaction can be performed by a polymerase. The extension reaction can be carried out using the cDNA molecule as a template since the 5' end and 3' end of the padlock probe are hybridized to the cDNA molecule, thereby capturing sequence information of the cDNA molecule into the padlock probe. The gap region can also be filled in by hybridizing an additional nucleotide or an additional oligonucleotide sequence to the gap region. The length of the additional oligonucleotide sequence can be determined based on the length of the gap region. For example, the additional oligonucleotide sequence can be of the same length as the gap region such that after hybridizing with the gap region, the 5' end of the additional oligonucleotide sequence is adjacent to the 3' end of the padlock probe and the 3' end of the additional oligonucleotide sequence is adjacent to the 5' end of the padlock probe. For example, the additional oligonucleotide sequence can comprise from 2 to 10, from 10 to 20, from 20 to 50, from 50 to 100, from 100 to 150, from 150 to 200, from 200 to 300, from 300 to 400, or from 400 to 500 nucleotides. The circularized padlock probe can then be generated by ligating the ends of the additional oligonucleotide sequence with the ends of the padlock probe.

The circularized padlock probe may be further subjected to rolling circle amplification (RCA) to generate an amplification product of a sequence of the circularized padlock probe. The amplification product can comprise a nucleic acid sequence corresponding to the nucleic acid sequence of the RNA molecule. The nucleic acid sequence of the amplification product can be detected, thereby identifying the nucleic acid sequence of the RNA molecule. Different detection methods may be used for nucleic acid detection including sequencing and hybridization. Examples of sequencing methods include sequencing by synthesis (SBS), sequencing by ligation (SBL), and sequencing by hybridization (SBH).

The reverse transcriptase or functional derivative thereof may have RNA catalytic cleavage activity. For example, the reverse transcriptase or functional derivative thereof may have ribonuclease (RNase) activity. The reverse transcriptase or functional derivative thereof may cleave RNA of a RNA/DNA duplex. The additional reverse transcriptase or functional derivative thereof may also have RNA catalytic cleavage activity. The reverse transcriptase or the additional reverse transcriptase may be an Avian myeloblastosis virus (AMV) reverse transcriptase, a wild type human immunodeficiency virus-1 (HIV-1) reverse transcriptase, or a Moloney Murine Leukemia Virus (M-MLV) reverse transcriptase.

To reverse transcribe the RNA molecule, a reverse transcription primer may be hybridized to the RNA molecule. The reverse transcription primer may be hybridizable to the 5' terminal region of the padlock probe. The reverse transcription primer may not be hybridizable to the 5' terminal region of the padlock probe. In the situation where the reverse transcription primer is not hybridizable to the 5' terminal region of the padlock probe, the region of the generated cDNA molecule that is complementary to the 5' terminal region of the padlock probe may be downstream of the reverse transcription primer by a distance of at least 1, at least 5, at least 10, at least 50, at least 100, at least 200, at least 500, or more nucleotides. As used herein, the distance between a region A (e.g., the region of the cDNA molecule complementary to the 5' terminal region of the padlock probe) and a region B (e.g., reverse transcription primer) of the same nucleic acid strand, wherein the region A is downstream of the region B, refers to the number of nucleotides between the 5' end of region A and the 3' end of the region B. As used herein, downstream refers to the direction from 5' end to 3' end of a nucleic acid strand.

The reverse transcription primer may comprise a functional moiety. The reverse transcription primer or an extension product thereof (e.g., cDNA molecule) can be immobilized to the 3D matrix via the function moiety. Examples of functional moiety include but are not limited to an amine, acrydite, alkyne, biotin, azide, and thiol.

The biological sample may comprise a plurality of target molecules. For example, the target molecules can be DNA molecules, RNA molecules, or protein molecules. The target molecules may have a relative 3D spatial relationship in the 3D matrix. In some cases, the biological sample comprises a plurality of RNA molecules. The plurality of RNA molecules may have a relative 3D spatial relationship in the 3D matrix.

In some cases, the RNA molecule or a portion thereof may be degraded or digested by the reverse transcriptase under a first set of conditions and the RNA molecule may be reverse transcribed by the same reverse transcriptase or an additional reverse transcriptase under a second set of conditions. The first set of conditions can be different than the second set of conditions. The first set of conditions may be the same as the second set of conditions. The first set of conditions or the second set of conditions can be selected from the group consisting of pH, temperature, cofactor concentration, and cation concentration. Examples of cofactor or cation include but are not limited to $Mg^{2+}$, $Mn^{2+}$, $Na^+$, ATP, and NADPH. The second set of conditions may inhibit RNase activity of the reverse transcriptase that is used to reverse transcribe the RNA molecule. For example, the second set of conditions may comprise an RNase inhibitor. The RNase inhibitor may be a small molecule inhibitor or a polypeptide.

The cDNA molecule may comprise a functional moiety. The cDNA molecule can be immobilized to the 3D matrix via the functional moiety. The functional moiety can be covalently crosslinked, copolymerize with or otherwise non-covalently bound to the matrix. The functional moiety can react with a crosslinker. The functional moiety can be part of a ligand-ligand binding pair. DNTP or dUTP can be modified with the functional group, so that the function moiety can be introduced into the DNA during amplification. Examples of functional moiety include but are not limited to an amine, acrydite, alkyne, biotin, azide, and thiol. In the case of crosslinking, the functional moiety can be crosslinked to modified dNTP or dUTP or both. Examples of crosslinker reactive groups include but are not limited to imidoester (DMP), succinimide ester (NHS), maleimide (Sulfo-SMCC), carbodiimide (DCC, EDC) and phenyl azide. Crosslinkers within the scope of the present disclosure may include a spacer moiety. Such spacer moieties may be functionalized. Such spacer moieties may be chemically stable. Such spacer moieties may be of sufficient length to allow amplification of the nucleic acid bound to the matrix. Examples of spacer moieties include but are not limited to polyethylene glycol, carbon spacers, photo-cleavable spacers and other spacers and the like.

In another aspect, the present disclosure provides a method for identification of a nucleic acid sequence in a biological sample. The method may comprise providing the biological sample comprising a RNA molecule hybridized to a DNA in a 3D matrix. The RNA molecule may comprise the nucleic acid sequence. Next, a DNA binding protein may be used to degrade or digest at least a portion of the RNA molecule hybridized to the DNA molecule. The DNA binding protein may not be a reverse transcriptase, a ribonuclease, or both. The DNA molecule may comprise an additional nucleic acid sequence that is a reverse complement of said nucleic acid sequence. Next, the additional nucleic acid sequence in the biological sample may be detected, thereby identifying the nucleic acid sequence. In some cases, a reverse transcriptase may be used to reverse transcribe the RNA molecule to generate the DNA molecule hybridized to the RNA molecule in the biological sample.

The DNA binding protein or functional derivative thereof may have RNA catalytic cleavage activity. For example, the DNA binding protein or functional derivative thereof may have ribonuclease (RNase) activity. The DNA binding protein or functional derivative thereof may cleave the RNA of a RNA/DNA duplex. The DNA binding protein may stabilize the DNA molecule. The DNA binding protein may stabilize the DNA of a RNA/DNA duplex. The DNA binding protein may increase a melting temperature of the DNA molecule. The DNA binding protein may stabilize the DNA molecule by increasing the melting temperature of the DNA molecule. In some cases, the DNA binding protein is Sso7d.

In another aspect, the present disclosure provides a method for identification of a nucleic acid sequence in a biological sample. The method may comprise providing the biological sample comprising a RNA molecule hybridized to a DNA molecule in a 3D matrix. The RNA molecule may comprise the nucleic acid sequence. Next, at least a portion of said RNA molecule hybridized to the DNA molecule may be non-enzymatically degraded. The DNA molecule may comprise an additional nucleic acid sequence that is a reverse complement of the nucleic acid sequence. Next, the DNA molecule may be contacted with a probe. The DNA molecule may hybridize with the probe upon contacting with the probe. Next, a sequence of the probe or a derivative thereof may be detected, thereby identifying the nucleic acid sequence of the RNA molecule.

The RNA molecule may be subjected to chemical degradation. The RNA molecule may be degraded or hydrolyzed in the absence of an enzyme. For example, RNA can be susceptible to base-catalyzed hydrolysis because the ribose sugar in RNA has a hydroxyl group at the 2' position. RNA hydrolysis can occur when the deprotonated 2' OH of the ribose, acting as a nucleophile, attacks the adjacent phosphorus in the phosphodiester bond of the sugar-phosphate backbone of the RNA. As used herein, RNA hydrolysis refers to a reaction in which a phosphodiester bond in the sugar-phosphate backbone of RNA is broken, cleaving the RNA molecule. Inorganic and organic compounds may be used to degrade or cleave RNA. In some cases, a metal complex may be used to degrade or cleave RNA. In some cases, a heavy metal ion may be used to degrade or cleave RNA. Both the transesterification step, where a 2',3'-cyclic phosphate may be formed with concomitant cleavage of RNA, and the hydrolysis step, where the 2',3'-cyclic phosphate may be converted to a phosphate monoester, can be catalyzed by inorganic or organic compounds.

The chemical degradation may be performed under a neutral to alkaline pH condition. For example, the pH may have a value of at least 6, at least 6.5, at least 7, at least 7.5, at least 8, at least 8.5, at least 9, at least 9.5, at least 10, at least 10.5, at least 11, at least 11.5, at least 12, at least 12.5, at least 13, at least 13.5, or 14. For another example, the pH may be from 6 to 7, from 7 to 8, from 8 to 9, from 9 to 10, from 10 to 11, from 11 to 12, from 12 to 13, or from 13 to 14. The chemical degradation may be performed under an acidic to neutral pH condition. For example, the pH may have a value of 0, at most 1, at most 2, at most 3, at most 4, at most 5, at most 6, or at most 7. For another example, the pH may be from 0 to 1, from 1 to 2, from 2 to 3, from 3 to 4, from 4 to 5, from 5 to 6, or from 6 to 7. The chemical degradation may be performed under a temperature condition in which RNA is unstable. For example, the temperature condition suitable for RNA degradation may be at least 5° C., at least 10° C., at least 20° C., at least 30° C., at least 40° C., at least 50° C., at least 60° C., at least 70° C., at least 80° C., at least 90° C., at least 100° C., or more. For another example, the temperature condition suitable for RNA degradation may be from 5° C. to 10° C., from 10° C. to 20° C., from 20° C. to 30° C., from 30 to 40° C., from 40 to 50° C., from 50 to 60° C., from 60 to 70° C., from 70 to 80° C., from 80 to 90° C., or from 90 to 100° C. The chemical degradation may be performed in the presence of a heavy metal ion. The term heavy metal refers to any metallic chemical element that has a relatively high density and may be toxic or poisonous at low concentrations. The heavy metal ion may be part of a metal complex. As used herein, the metal complex refers to a macrocyclic complex formed by the union of a central metal ion with a non-metallic ion or molecule. The metal ion can comprise copper, zinc, cobalt, nickel, palladium, lead, iridium, manganese, iron, molybdenum, vanadium, titanium, ruthenium, bismuth, cadmium, magnesium, rhodium, uranium, a transition metal, yttrium and the Lanthanide metals. The non-metallic ion can comprise a ligand, chelate or complexing agent. For large metal ions such as the lanthanides(III), ligands that provide six or more donor atoms may be used. Ligands for any of the metal ions within the scope of the present disclosure need not form thermodynamically stable complexes with the metal ions. It may be sufficient that they are kinetically inert to metal ion release. Accordingly, macrocyclic ligands can form kinetically inert complexes with labile metal ions if properly designed. Also, tetraazamacrocycle ligands strongly chelate the transition metal ions and Zn(II). The chemical degradation may be performed in the presence of a divalent cation, for example, $Mg^{2+}$ and $Zn^{2+}$. The chemical degradation may be performed under a condition selected from the group consisting of a pH having value from 6 to 14, a pH having value from 0 to 6, a temperature from 10° C. to 100° C., in the presence of a heavy metal ion, in the presence of a divalent cation, and any combination thereof.

In yet another aspect, the present disclosure provides a method for processing a biological sample. The method may comprise providing the biological sample comprising a RNA molecule in a 3D matrix. The RNA molecule may comprise a nucleic acid sequence. Next, a primer may be hybridized to the RNA molecule. The primer may be a reverse transcription primer. The primer may not include a functional moiety for immobilization to the 3D matrix. Next, a reverse transcriptase may be used to reverse transcribe the RNA molecule by extending the primer to generate a cDNA molecule hybridized to the RNA molecule in the biological sample. The cDNA molecule may comprise a functional moiety that can immobilize the cDNA molecule to the 3D matrix.

In some cases, the RNA molecule hybridized to the cDNA molecule may be degraded to provide the cDNA molecule immobilized to the 3D matrix through the functional moiety. The cDNA molecule may comprise an additional nucleic acid sequence that is a reverse complement of the nucleic acid sequence.

The RNA molecule may comprise a functional moiety. The RNA molecule may be immobilized to the 3D matrix via the functional moiety.

Various methods may be used to degrade the RNA molecule. For example, the RNA molecule may be degraded by a non-ribonuclease enzyme. The non-ribonuclease enzyme can be a reverse transcriptase or a DNA binding protein. For another example, the RNA molecule may be degraded by a non-enzymatic reaction. The non-enzymatic reaction may be performed under a condition selected from the group consisting of a pH having value from 6 to 14, a temperature from 10° C. to 100° C., in the presence of a heavy metal ion, and any combination thereof.

The cDNA molecule may be contacted with a probe. The probe may comprise a region that is not hybridizable with said cDNA molecule. The region that is not hybridizable with said cDNA molecule may be a terminal region or an internal region between two terminal regions.

The probe may be a padlock probe, wherein the padlock probe comprises 5' and 3' terminal regions complementary to the cDNA molecule. The 5' and 3' terminal regions of the padlock probe may be hybridized to the cDNA molecule. The padlock probe may be circularized by coupling two ends of the padlock probe together to yield a circularized padlock probe. For example, the two ends of the padlock probe can be ligated together by a ligase. A nucleic acid sequence of the circularized padlock probe or a derivative thereof may be detected, thereby identifying the nucleic acid sequence of the RNA molecule. For example, the nucleic acid sequence of the circularized padlock probe or a derivative thereof can be detected by nucleic acid hybridization or sequencing.

Upon hybridizing the two ends of padlock probe and the cDNA molecule, the two ends of the padlock probe may be contiguous or separated by a gap region of the cDNA molecule. The gap region may be of various lengths. For example, the gap region can comprise at least 1, at least 5, at least 10, at least 15, at least 20, at least 25, at least 30, at least 35, at least 40, at least 45, or at least 50 nucleotide(s). For another example, the gap region can comprise from 2 to 10, from 10 to 20, from 20 to 50, from 50 to 100, from 100 to 150, from 150 to 200, from 200 to 300, from 300 to 400, from 400 to 500 nucleotides. A circularized padlock probe can be generated by ligating two ends of the padlock probe together. In the cases where the two ends are contiguous, the two ends can be ligated directly. In the cases where the two ends are separated by a gap region, the gap region can be filled in before ligation. The gap region can be filled in by incorporating one or more nucleotides in an extension reaction, for example, by extending from the 3' end of the two ends. The extension reaction can be performed by a polymerase. The gap region can also be filled in by hybridizing an additional nucleotide or an additional oligonucleotide sequence to the gap region. The length of the additional oligonucleotide sequence can be determined based on the length of the gap region. For example, the additional oligonucleotide sequence can be of the same length as the gap region such that after hybridizing with the gap region, the 5' end of the additional oligonucleotide sequence is adjacent to the 3' end of the padlock probe and the 3' end of the additional oligonucleotide sequence is adjacent to the 5' end of the padlock probe. For example, the additional oligonucleotide sequence can comprise from 2 to 10, from 10 to 20, from 20 to 50, from 50 to 100, from 100 to 150, from 150 to 200, from 200 to 300, from 300 to 400, or from 400 to 500 nucleotides. The circularized padlock probe can then be generated by ligating the ends of the additional oligonucleotide sequence with the ends of the padlock probe.

The circularized padlock probe may be further subjected to amplification to generate an amplification product of a sequence of the circularized padlock probe. For example, the circularized padlock probe may be subjected to rolling circle amplification (RCA). The amplification product may comprise a nucleic acid sequence corresponding to the nucleic acid sequence of the RNA molecule. The nucleic acid sequence of the amplification product may be detected, thereby identifying the nucleic acid sequence of the RNA molecule.

The probe may comprise a functional moiety. The probe may be immobilized to the 3D matrix via the functional moiety. The functional moiety may be directly conjugated on the probe. The functional moiety may be introduced to the probe during synthesis of the probe. For example, a nucleotide analog having a functional moiety or a precursor of the functional moiety may be incorporated to a growing chain of the probe during synthesis. The functional moiety may be introduced to the probe through a tethering oligonucleotide. The probe may hybridize to the tethering oligonucleotide comprising the functional moiety. The tethering oligonucleotide may hybridize to the region of the probe that is not hybridizable to the cDNA molecule. A sequence of the probe or a derivative thereof may be detected, thereby identifying the nucleic acid sequence of the RNA molecule.

The cDNA molecule may comprise a functional moiety. The reverse transcriptase may be used to incorporate a nucleotide analog comprising the functional moiety into a growing strand, to yield the cDNA molecule comprising the nucleotide analog. For example, the nucleotide analog comprises amino-allyl dUTP, 5-TCO-PEG4-dUTP, C8-Alkyne-dUTP, 5-Azidomethyl-dUTP, 5-Vinyl-dUTP, 5-Ethynyl dUTP, or a combination thereof.

The primer or the cDNA molecule may be modified, after generating the cDNA molecule, to include the functional moiety. The primer may be modified to include the functional moiety prior to generating the cDNA molecule. For example, the primer may be modified with the functional moiety through conjugation chemistry. The primer may comprise a region that is not hybridizable to the RNA molecule. The region that is not hybridizable to the RNA molecule may be coupled to a tethering oligonucleotide that comprises a functional moiety. For example, the region may hybridize to the tethering oligonucleotide that comprises the functional moiety.

The functional moiety may be attached to the cDNA molecule through an enzymatic reaction or a non-enzymatic reaction. The enzymatic reaction may comprise using an enzyme to attach a nucleotide or an oligonucleotide having the functional moiety to the cDNA molecule. The enzyme can be a ligase, a polymerase, or a combination thereof. The non-enzymatic reaction may comprise attaching a chemical reagent having the functional moiety to the cDNA molecule by alkylation or oxymercuration. The cDNA molecule may be coupled to a tethering oligonucleotide having a functional moiety. For example, the cDNA molecule may hybridize to a tethering oligonucleotide having a functional moiety. The tethering oligonucleotide may hybridize to the primer.

The 3D matrix may further comprise an additional functional moiety. The additional functional moiety may react with the function moiety of the cDNA molecule, thereby immobilizing the cDNA molecule.

In a further aspect, the present disclosure features a kit comprising some or all of the reagents, enzymes, probes, and primers necessary to perform the methods described herein. The items comprising the kit may be supplied in separate vials or may be mixed together, where appropriate.

FIG. 1 shows an example of a method for identification of a nucleic acid sequence in a biological sample. In a first operation 101, the biological sample comprising a ribonucleic acid (RNA) molecule hybridized to a deoxyribonucleic acid molecule (DNA) in a three-dimensional (3D) matrix may be provided. The RNA molecule may comprise a nucleic acid sequence to be identified. Next, in a second operation 102, a reverse transcriptase may be used to degrade or digest at least a portion of the RNA molecule hybridized to the DNA molecule. The DNA molecule may comprise an additional nucleic acid sequence that is a reverse complement of the nucleic acid sequence. Next, in a third operation 103, the additional nucleic acid sequence in the biological sample may be detected, thereby identifying the nucleic acid sequence.

Figure 2:
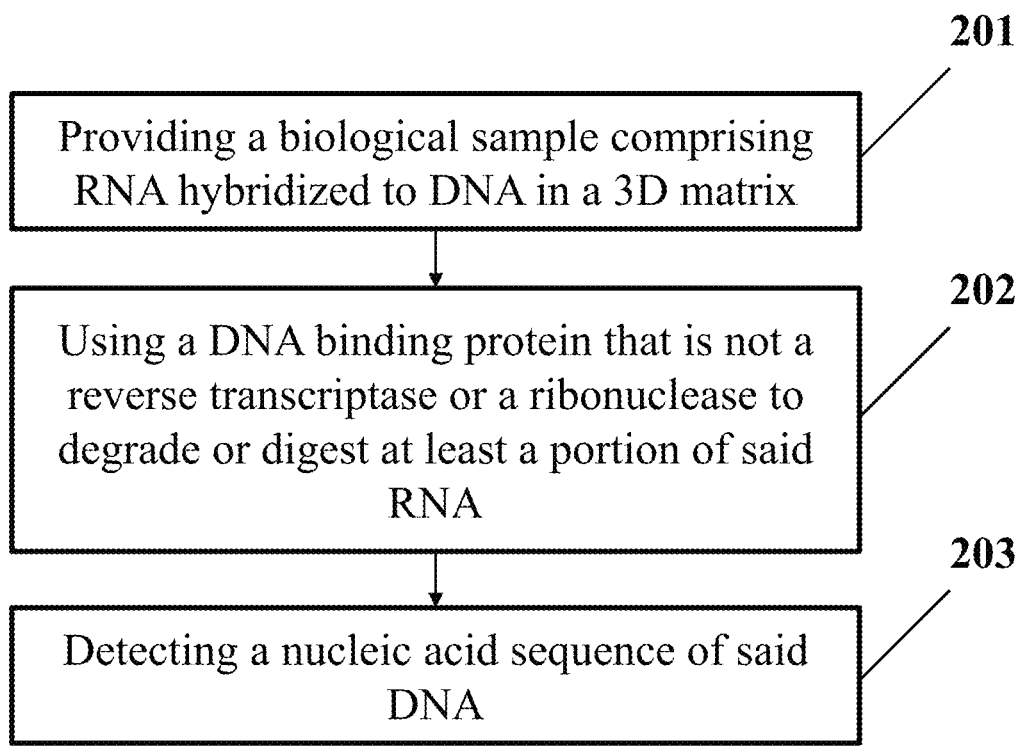
FIG. 2 shows an example of a method for identification of a nucleic acid sequence in a biological sample.

FIG. 2 shows an example of a method for identification of a nucleic acid sequence in a biological sample. In a first operation 201, the biological sample comprising a ribonucleic acid (RNA) molecule hybridized to a deoxyribonucleic acid molecule (DNA) in a three-dimensional (3D) matrix may be provided. The RNA molecule may comprise a nucleic acid sequence to be identified. Next, in a second operation 202, a deoxyribonucleic acid (DNA) binding protein that is not a reverse transcriptase or a ribonuclease may be used to degrade or digest at least a portion of the RNA molecule hybridized to the DNA molecule. The DNA molecule may comprise an additional nucleic acid sequence that is a reverse complement of the nucleic acid sequence. Next, in a third operation 203, the additional nucleic acid sequence in the biological sample may be detected, thereby identifying the nucleic acid sequence.

Figure 3:
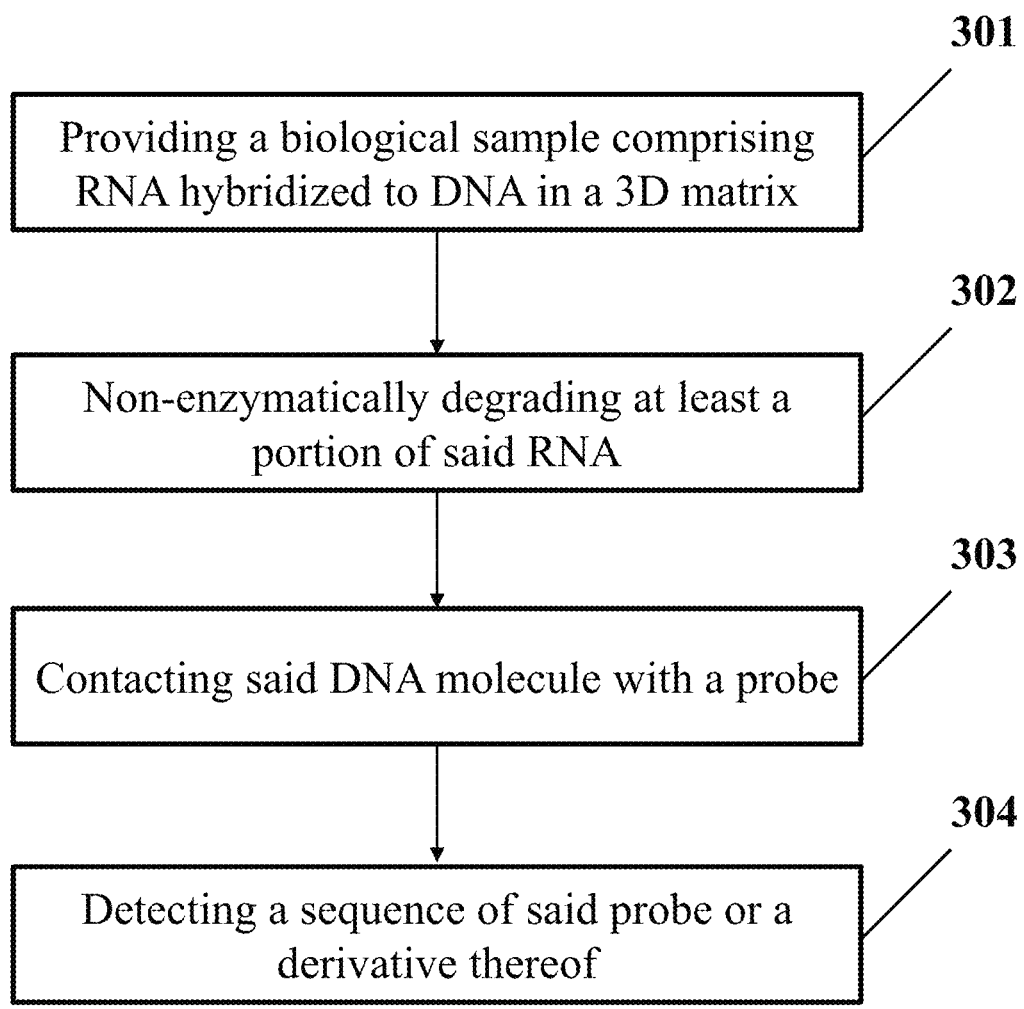
FIG. 3 shows an example of a method for identification of a nucleic acid sequence in a biological sample.

FIG. 3 shows an example of a method for identification of a nucleic acid sequence in a biological sample. In a first operation 301, the biological sample comprising a ribonucleic acid (RNA) molecule hybridized to a deoxyribonucleic acid molecule (DNA) in a three-dimensional (3D) matrix may be provided. The RNA molecule may comprise a nucleic acid sequence to be identified. Next, in a second operation 302, at least a portion of the RNA molecule hybridized to the DNA molecule may be degraded non-enzymatically. The DNA molecule may comprise an additional nucleic acid sequence that is a reverse complement of the nucleic acid sequence. Next, in a third operation 303, the cDNA molecule may be contacted by a probe. Next, in a fourth operation 304, a sequence of the probe or a derivative thereof may be detected, thereby identifying the nucleic acid sequence of the RNA molecule.

Figure 4:
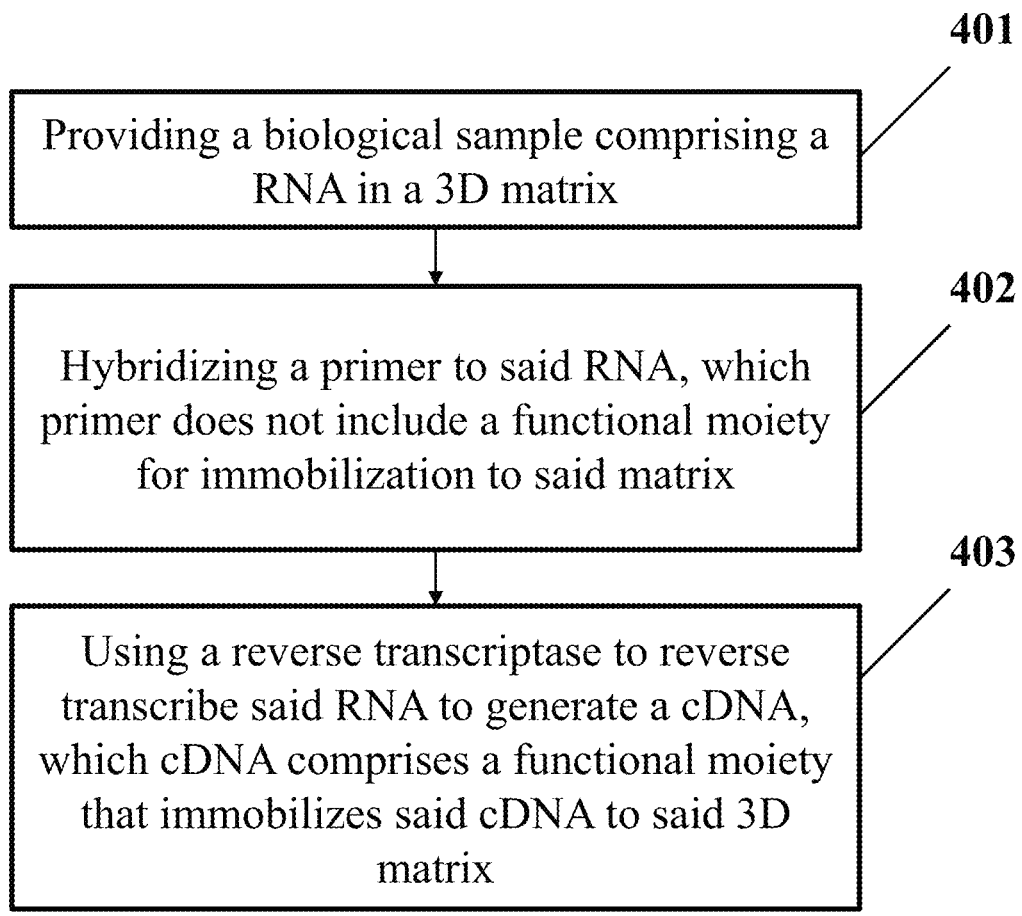
FIG. 4 shows an example of a method for processing a biological sample.

FIG. 4 shows an example of a method for processing a biological sample. In a first operation 401, the biological sample comprising a ribonucleic acid (RNA) molecule in a three-dimensional (3D) matrix may be provided. The RNA molecule may comprise a nucleic acid sequence. Next, in a second operation 402, a primer may be hybridized to the RNA molecule, which primer does not include a functional moiety for immobilization to the matrix. Next, in a third operation 403, a reverse transcriptase may be used to reverse transcribe the RNA molecule by extending the primer to generate a complementary deoxyribonucleic acid (cDNA) molecule hybridized to the RNA molecule in the biological sample. The cDNA molecule may comprise a functional moiety that immobilizes the cDNA molecule to the 3D matrix.

In various embodiments, a target DNA or RNA molecule can hybridize to a primer or a probe in the present of a hybridization reaction enhancing agent. The hybridization reaction enhancing agent can enhance a rate of the hybridization reaction between a target nucleic acid molecule and a probe having sequence complementarity with the target sequence of the target molecule, as compared to another hybridization reaction conducted between the target nucleic acid molecule and the probe in the absence of the hybridization reaction enhancing agent. An example of a hybridization reaction enhancing agent may be dextran sulfate. However, enzymes may be strongly inhibited by dextran sulfate, and being a highly charged, high molecular weight polymer, it may be difficult to wash dextran sulfate from the sample to the point where the downstream enzymatic reactions, e.g., reverse transcription, ligation, DNA polymerization, are not strongly inhibited. In the absence of a hybridization reaction enhancing agent, however, the kinetics of in situ hybridization may be orders of magnitude slower. Therefore, a hybridization reaction enhancing agent that does not strongly inhibit enzymatic reactions can be used in the methods described herein. The hybridization reaction enhancing agents may be high-molecular weight, high valency charged polymers. For example, hybridization reaction enhancing agent may be polymers such as polyacrylic acid, polyvinylsulfonic acid, and alginate. The hybridization reaction enhancing agents may be polymers similar to dextran sulfate.

In some instances, an intermolecular organization of the hybridization reaction enhancing agents may be a factor in determining its effectiveness as a hybridization reaction enhancing agent. As an example, dextran sulfate can aid in the formation of networks (e.g., highly localized concentrations of probes) during hybridization, thus expediting the annealing process. The G-blocks of alginate can participate in intermolecular cross-linking with divalent cations (e.g., $Ca^{2+}$) to form hydrogels. Dextran sulfate may not form hydrogels other than under exogenous chemical cross-linking reactions and in the presence of chitosan, neither of which may be present during typical nucleic acid hybridization reactions. In some instances, the hybridization reaction enhancing agent may self-associate in the formation of hydrogels. Alternatively, the hybridization reaction enhancing agent may not self-associate in the formation of hydrogels. The difference in the ability to self-associate in the formation of hydrogels may explain the difference between dextran sulfate and alginate in improving the kinetics of nucleic acid DNA hybridization reactions.

For example, polyacrylic acid and polyvinylsulfonic acid may both effectively function as a hybridization reaction enhancing agent while alginate may not. This may be due to the intermolecular organization, which can reduce its effectiveness in crowding DNA. In some instances, polyacrylic acid may inhibit enzymatic reactions, but polyvinylsulfonic acid may exhibit much less inhibition. As an example, one mechanism of inhibition may be via chelation of essential metal or charged cofactors, such as $Mg^{2+}$, $Ca^{2+}$, $Mn^{2+}$, $Na^+$, phosphate, and other metal and charged ions, which are required for enzyme function. A polyion salt such as sodium polyacrylic acid may exchange sodium ions for magnesium ions in the presence of a magnesium-containing enzyme reaction buffer, reducing the effective concentration of the essential cofactor. Another mechanism of inhibition may be binding and structural damage to the enzyme, e.g. the charge attraction and binding between charged domains of the enzyme and the ionic polymer, which may cause effective sequestration of the enzyme within the reaction, as well as disrupt electrostatic or charge interactions within the enzyme, which may be required for enzyme structure and related function. Wettability, or hydrophobicity, charge, and structure may alternatively, or additionally contribute to the strength of polyion-protein interactions. Protein absorption on the polyion or within the polyionic network may contribute to effective decrease in enzyme concentration.

In some embodiments, the property or activity of the hybridization reaction enhancing agent can be controlled (e.g., inactivated). For example, some polymers that function as the hybridization reaction enhancing agent can comprise charged groups and subsequently the charged groups can be cleaved off or neutralized. This process can convert the polymers into neutral polymers such as PEG, which can enhance the efficiency of enzymatic reactions. In some embodiments, polymers that function as the hybridization reaction enhancing agents can be specifically degraded into small monomers and can be easily removed from the sample such as by washing away from the sample. The chemistry of passivation or degradation of the hybridization reaction enhancing agent may need to be orthogonal to nucleic acids, i.e., not degrading nucleic acids or rendering nucleic acids incompatible. Some of these functional groups include alpha-hydroxy acids, which can be cleaved by sodium periodate; beta-keto acids, which can be cleaved with heat; phosphorothioate linkages, which can be cleaved with silver ions; disulfide linkages, which can be cleaved by reduction into thiols; and other types of chemical linkages which may be cleaved by photo- or chemical treatment.

Examples of polyions or polyelectrolytes for enzyme-compatible enhancement of nucleic acid hybridization kinetics include polycondensation reactions of Cys(Lys)nCys, polymers such as PEG, PVA, or PAA, which may be subsequently modified via a cleavable linker to include chemical groups conferring ionic charge, or polymers formed from monomers including cleavable linkages, such that the polymer may be degraded subsequent to functioning as a hybridization reaction enhancing agent. As an alternative to ionic charge, these polymers may include non-ionic groups that become hydrated in solution, which can enhance nucleic acid hybridization rates by molecular crowding and/or sequestration of water.

In some cases, the hybridization reaction enhancing agent may not be controlled. For example, the hybridization reaction enhancing agent may not comprise a cleavable functional group such that it can be inactivated or degraded into monomers. In these cases, the hybridization reaction enhancing agents may be removed from the sample after functioning as the hybridization reaction enhancing agent to enhance nucleic acid hybridizations. For example, the hybridization reaction enhancing agent can be washed away from the sample or the 3D matrix. The wash step may be performed after hybridizing a primer or a probe to a target nucleic acid molecule and before any subsequent enzymatic reactions such as reverse transcription, ligation, and amplification.

The present disclosure provides methods to enhance the hybridization of probes for capturing RNA, cDNA, and DNA species onto the 3D matrix for detection via FISSEQ. The hybridization reaction enhancing agent can be added in the hybridization buffer. In some embodiments, a hybridization buffer containing high salt, such as SSC (sodium chloride sodium citrate buffer), can be used. In some embodiments, a hybridization buffer containing blocking agents can be used. The blocking agents can reduce non-specific binding of probes to off-target sequences and/or by preventing electrostatic interactions with other components of the sample, such as yeast tRNA, salmon sperm, detergents such as Triton-X, Tween 20, SPAN, peptides such as BSA, and other agents such as Ficoll. In some embodiments, a hybridization buffer containing agents which alter the annealing properties of DNA, such as the melting temperature. An example of agents that can alter the annealing temperature includes formamide. The hybridization reaction enhancing agent can have an average molecular weight of at least about 1, 2, 3, 4, 5, 6, 7, 8, 9, 10, 20, 30, 40, 50, 60, 70, 80, 90, 100, 200, 500, 1000, or more kDa. In some embodiments, a hybridization reaction enhancing agent can present in at least about 1%, 5%, 10%, 15%, 20%, or more weight per volume in the reaction.

The hybridization reaction enhancing agent can be a polyionic, a polyelectrolyte, a hydrophilic or a hydrating polymer. The hybridization reaction enhancing agent can comprise a polymer backbone and one or more hydrating groups. The hydrating groups can be ionic, electrolytic, or hydrophilic. In some embodiments, the hydrating groups may be specifically inactivated, e.g., as by rendering an ionic group to have neutral charge, or as by rendering a strongly hydrating group to be weakly hydrating. The inactivation chemistry can be substantially nonreactive with RNA, DNA, proteins, and/or other types of biomolecules. The inactivated polymer is compatible with enzymatic reactions.

The hybridization reaction enhancing agent can comprise a cleavable linkage between the polymer backbone and the hydrating group. The cleavable linkages can comprise alpha-hydroxy acids, which can be cleaved by sodium periodate. The cleavable linkages comprise beta-keto acids, which can be cleaved with heat. The cleavable linkages can comprise phosphorothioate linkages, which can be cleaved with silver ions. The cleavable linkages can comprise disulfide linkages, which can be cleaved by reduction into thiols. Other types of chemical linkages may be cleaved by photo- or chemical treatment. In some cases, the hybridization reaction enhancing agent can comprise cleavable linkages along the backbone of the polymer, where the cleavable linkages can be any types of cleavable linkages described herein.

The methods provided herein can comprise the use of a hybridization reaction enhancing agent in sample processing for targeted RNA or DNA detection. In some cases, a plurality of probes can be hybridized in situ using a hybridization buffer containing one of the hybridization reaction enhancing agents described herein.

The methods described herein may comprise hybridizing a plurality of probes in situ using a hybridization buffer containing one of the hybridization reaction enhancing agents described herein. In some embodiments, the methods further comprise triggering cleavage of the cleavable groups of the hybridization reaction enhancing agents to inactivate the hybridization reaction enhancing agent. In some other embodiments, the methods further comprise removing the hybridization reaction enhancing agents from the sample or the 3D matrix without inactivating the hybridization reaction enhancing agents.

Computer Systems

Figure 5:
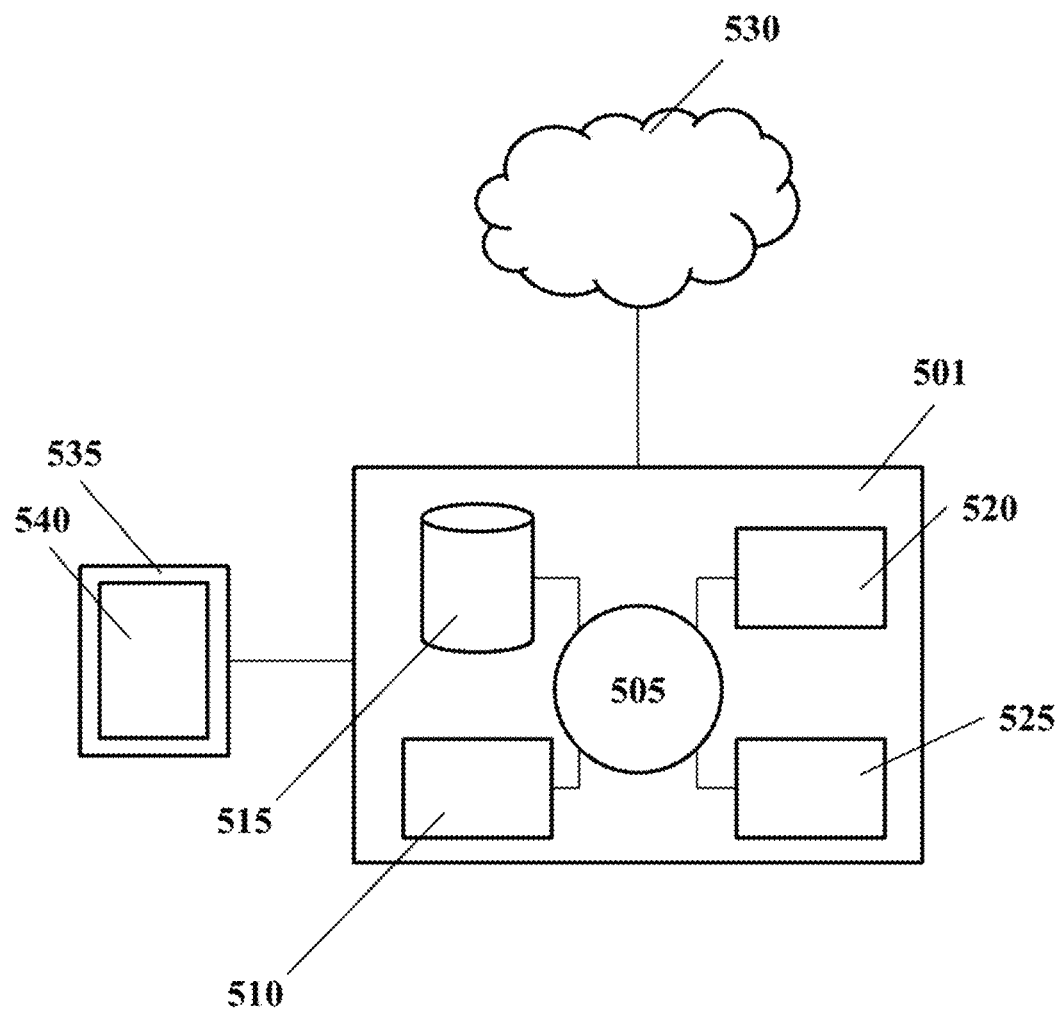
FIG. 5 shows a computer system that is programmed or otherwise configured to implement methods provided herein.

The present disclosure provides computer systems that are programmed to implement methods of the disclosure. FIG. 5 shows a computer system 501 that is programmed or otherwise configured to process a biological sample and/or identify a nucleic acid sequence in a biological sample. The computer system 501 can regulate various aspects of components and/or devices of the present disclosure utilized in detection of nucleic acid sequences in a biological sample and/or sample processing, such as, for example, light sources, detectors (e.g., light detectors), devices or components utilized for releasing agents, devices or components utilized in providing conditions for reactions (e.g., hybridization, sequencing, enzymatic reactions), etc. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515

(e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 1115 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user (e.g., a user performing sample processing or nucleic acid sequence detection of the present disclosure). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540 for providing, for example, protocols to perform the sample processing methods and/or nucleic acid sequence detection methods described in the present disclosure. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, be executed so as to detect a nucleic acid sequence utilizing methods and systems disclosed in the present disclosure. Optionally, the algorithms may be executed so as to control or effect operation of a component (e.g., light source, detector, reagent flow, etc) of the systems described herein to effect detection of a nucleic acid sequence.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

EXAMPLE

Example I

Immobilizing, Amplifying and Imaging DNA/RNA Molecules within Cells

Human iPS cells or human primary fibroblasts will be grown on a 1.5 cover slip. They will be fixed using 4% formaldehyde in PBS for 15 min, followed by three washes of 70% ethanol. The reverse transcription mixture containing 1 µM random hexamer or 0.1 µM polydT(18)V primer with additional adapter sequences (TCTCGGGAACGCT-GAAGA), 250 µM dNTP, 40 µM aminoallyl dUTP (Anaspec), 20 U RNase inhibitor and 100 U MMuLV reverse transcriptase (Enzymatics) will then be added to the fixed cells and incubated overnight at 37° C. The sample will then be washed using PBS, and cross-linked using 100 µM BS(PEG)9 (Thermo-Fisher Scientific) in PBS for 1 hour, followed by 1M Tris treatment for 15 min. The circularization mixture containing 25 U CircLigase (Epicentre), 1 mM MnCl and 1 M Betaine will be added, and the sample will be incubated at 60° C. for 2 hours. The RNA will be degraded using Avian myeloblastosis virus (AMV) reverse transcriptase at 37° C. for 1 hour. Alternatively, the RNA will be degraded using a solution having a pH from 8 to 10, or by heating the sample at 100° C. for about 20 min. The RCA primer is then hybridized to the sample at 60° C. for 15 min and washed. For rolling circle amplification, 100 U phi29 DNA polymerase (Enzymatics), 250 µM dNTP and 40 µM aminoallyl dNTP will be added to the sample and incubated at 30° C. overnight. The sample will then be washed using PBS, and cross-linked using 100 µM BS(PEG)9 in PBS for 1 hour, followed by 1M Tris treatment for 15 min. For the DNA amplicon detection, 1 µM fluorescently label oligonucleotides will be diluted in 2×SSC and hybridized to the matrix containing the DNA amplicons at 60° C. and washed. Imaging can be done using Leica SP5 scanning confocal microscope using 10×, 20× or 63× objectives in four color channels (FITC, Cy3, Texas Red and Cy5). The image stacks containing up to 50 optical sections can then be visualized using Imaris Bitplane software for three-dimensional reconstruction of the DNA amplicons within the sample matrix.

Methods described herein allow one to immobilize, amplify and image single DNA/RNA molecules in a three-dimensional space without perturbing the structure. DNA/RNA can be amplified in situ. The DNA/RNA can be co-polymerized into a matrix material in situ, and individual amplicons can be interrogated/hybridized with fluorescent oligonucleotides and imaged. When viewed under much higher magnification, individual amplicons can be imaged using confocal microscopy. This allows one to find out where different DNA/RNA molecules reside, how they are compartmentalized among different cell types and morphologies and how their representation changes over time in developing tissues. The similar concept can be used for many other specimens in both natural and synthetic materials, as long as they can be co-polymerized and/or encapsulated by the DNA amplicons.

According to one specific aspect, inside individual mammalian cells, 20 to 500K mRNA molecules may be distributed throughout the cytoplasm. Cells can be fixed and permeabilized. Cellular RNA can then be converted into cDNA molecules using dUTP in place or in addition to dTTP. The cDNA molecules containing modified dUMP residues can then be cross-linked to each other and circularized, forming a three-dimensional pseudo-polymer of circular cDNA molecules inside individual cells. Then rolling circle amplification can be used to amplify the cDNA network into a DNA amplicon network. This cell-based DNA amplicon network then stores information about each transcript's identity, location, variation/mutations, etc. The cell-based DNA amplicon matrix can be read using sequencing by ligation (i.e. ABI SoLiD), sequencing by synthesis (i.e. Illumina), or any other proprietary or open sequencing chemistries. Sequencing may be whole genome sequencing or targeted sequencing. Sequencing may be performed by massively parallel array sequencing (e.g., Illumina) or single molecule sequencing (e.g., Pacific Biosciences of California or Oxford Nanopore). Given the three-dimensional nature of the DNA amplicon network, one can use confocal or multi-photon microscopy to sequencing individual amplicons throughout the whole thickness of the amplicon network, enabling one to visualize the cDNA distribution of transcripts between the apical side and the basal side of the cells. Given the tight packing density, one can selectively read different subpopulations sequentially, reducing the density of information read at any given time and extending over time for better spatial resolution.

Example II

Sample Processing and Target Detection within a 3D Matrix

Figure 6:
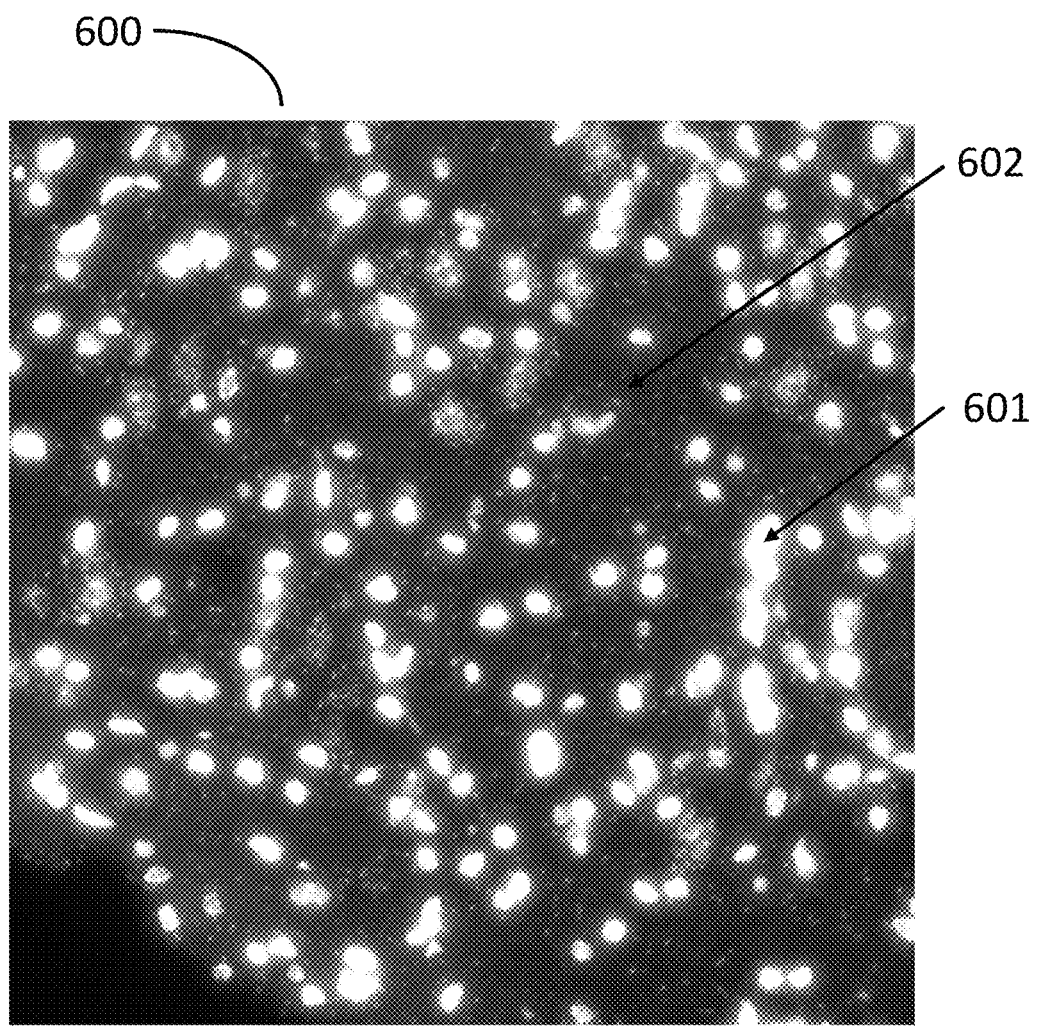
FIG. 6 shows an example image of a tissue sample processed and imaged using methods of the present disclosure.

Mouse brain tissue samples were sectioned onto a glass slide. They were fixed using 4% formaldehyde in PBS for 20 min, followed by quenching in 100 mM glycine for 15 min and a 5 min 1×PBS rinse. Samples were then gradually dehydrated in ethanol and incubated overnight in 100% ethanol. Samples were gradually rehydrated to 1×PBST, and permeabilized in 0.2% TritonX-100. 1 µM tetherable reverse transcription primers were hybridized overnight at 37° C. in a buffer containing 2×SSC and 10% dextran sulfate. Samples were washed for 20 min at 37° C. to remove excess oligonucleotides, embedded in a polyacrylamide matrix, and proteins cleared overnight at 37° C. with 16 U/mL of proteinase K in 4% SDS buffer, pH 7.3. To remove residual hybridization reaction enhancing agents and proteinase, samples were washed for several hours in 1×PBST, replacing buffer every 30 min. The reverse transcription mixture containing 1.25 mM dNTP, 1 U/µL RNase Inhibitor (Enzymatics), and 10 U/µL EnzScript reverse transcriptase (Enzymatics) were added to cleared sections and incubated overnight at 37° C. ssRNA and RNA duplexed with cDNA product were removed via borate buffer-mediated chemical hydrolysis performed at 55° C. for 2 hours, and then DNA padlock oligonucleotide probes were hybridized to ss-cDNA during an overnight incubation at 37° C. in a buffer containing 2×SSC and 10% dextran sulfate. Samples were washed for 20 min 37° C. to remove unbound DNA padlock oligonucleotide probes, then further washed for several hours in 1×PBST, replacing buffer every 30 min, to remove residual hybridization reaction enhancing agents. DNA padlock oligonucleotide probes were ligated by 30 U/µL of T7 ligase (Enzymatics) at room temperature for 60 min, then rolling circle amplification was performed overnight at 30° C. in the presence of 0.5 U/µL phi29 DNA polymerase (Enzymatics), 625 µM dNTPs, and 0.025 µM compaction oligonucleotides. For the DNA amplicon detection, 1 µM fluorescently label oligonucleotides were diluted in 2×SSC and hybridized to the matrix containing the DNA amplicons at 60° C. and washed. Imaging was done using ReadCoor automated fluorescent in situ sequencing device. The 3D image data were processed to identify each amplicon and visualized using a web-browser based software tool for three-dimensional reconstruction of the DNA amplicons within the matrix. FIG. 6 shows an example image of the mouse brain tissue sample 600 processed and imaged using the method described above. Cell nuclei (e.g., 601 of FIG. 6) are shown as bigger bright spots across the image. Sequencing readout of fluorescent signals of amplicons (e.g., 602 of FIG. 6) are shown as smaller and dimmer spots across the image. Shown in the image is the sequencing readout of one sequencing cycle. The sample was subjected to multiple sequencing cycles to determine the sequences of bases for each amplicon.

What is claimed is:

1. A method for identification of a nucleic acid sequence in a biological sample, comprising:
   (a) providing said biological sample comprising a ribonucleic acid (RNA) molecule hybridized to a deoxyribonucleic acid (DNA) molecule in a three-dimensional (3D) matrix, wherein said RNA molecule comprises said nucleic acid sequence, and wherein said DNA molecule comprises an additional nucleic acid sequence that is a reverse complement of said nucleic acid sequence;
   (b) degrading or digesting at least a portion of said RNA molecule hybridized to said DNA molecule, wherein said at least said portion of said RNA molecule is degraded or digested non-enzymatically at conditions suitable for conducting a click reaction; and
   (c) detecting said additional nucleic acid sequence, thereby identifying said nucleic acid sequence.

2. The method of claim 1, wherein said DNA molecule is immobilized to said 3D matrix.

3. The method of claim 2, wherein said DNA molecule comprises a functional moiety, and wherein said DNA molecule is immobilized to said 3D matrix via said functional moiety.

4. The method of claim 1, wherein said RNA molecule is immobilized to said 3D matrix.

5. The method of claim 4, wherein said RNA molecule comprises a functional moiety, and wherein said RNA molecule is immobilized to said 3D matrix via said functional moiety.

6. The method of claim 1, wherein (c) comprises contacting said DNA molecule with a probe.

7. The method of claim 6, wherein said probe comprises a functional moiety, and wherein said probe is immobilized to said 3D matrix via said functional moiety.

8. The method of claim 6, wherein said probe is a padlock probe, wherein said padlock probe comprises 5' and 3' terminal regions complementary to said DNA molecule, and wherein said 5' and 3' terminal regions of said padlock probe are hybridized to said DNA molecule.

9. The method of claim 8, further comprising circularizing said padlock probe by ligating two ends of said padlock probe together, to yield a circularized padlock probe.

10. The method of claim 9, wherein said two ends of said padlock probe are contiguous.

11. The method of claim 9, wherein said two ends of said padlock probe are separated by a gap region comprising at least one nucleotide.

12. The method of claim 11, wherein said gap region comprises from 2 to 500 nucleotides.

13. The method of claim 11, further comprising filling said gap region by incorporating at least one nucleotide in an extension reaction.

14. The method of claim 11, further comprising filling said gap region by at least one additional nucleotide or an oligonucleotide sequence.

15. The method of claim 9, further comprising subjecting said circularized padlock probe to rolling circle amplification (RCA) to generate a nucleic acid molecule using said circularized padlock probe as a template, which nucleic acid molecule comprises a sequence corresponding to said nucleic acid sequence of said RNA molecule.

16. The method of claim 15, further comprising detecting said sequence of said nucleic acid molecule, thereby identifying said nucleic acid sequence of said RNA molecule.

17. The method of claim 1, further comprising, prior to (a), reverse transcribing said RNA molecule to generate said DNA molecule hybridized to said RNA molecule in said biological sample.

18. The method of claim 17, wherein said RNA molecule is reverse transcribed using a reverse transcriptase.

19. The method of claim 17, further comprising, prior to (a), hybridizing a reverse transcription primer to said RNA molecule, wherein said reverse transcription primer comprises a functional moiety, and wherein said DNA molecule is immobilized to said 3D matrix via said functional moiety.

20. The method of claim 17, wherein (b) is performed under a first set of conditions and reverse transcribing said RNA molecule is performed under a second set of conditions, wherein said first set of conditions is different than said second set of conditions.

21. The method of claim 20, wherein said first set of conditions or said second set of conditions is selected from the group consisting of pH, temperature, cofactor concentration, and cation concentration.

22. The method of claim 1, wherein in (b) said at least said portion of said RNA molecule is degraded or digested non-enzymatically in a presence of a metal ion suitable for conducting said click reaction.

23. The method of claim 22, wherein said metal ion is a copper ion.

24. The method of claim 1, wherein said biological sample comprises a plurality of RNA molecules, wherein in (a) said plurality of RNA molecules has a fixed relative 3D spatial relationship.

25. The method of claim 1, wherein (b) comprises degrading said at least said portion of said RNA molecule non-enzymatically by subjecting said at least said portion of said RNA molecule to (1) a pH in a range from 6 to 14, (2) a temperature from 10° C. to 100° C., (3) a heavy metal ion, or (4) a divalent cation.

26. A method for processing a biological sample, comprising:
   (a) providing said biological sample comprising a ribonucleic acid (RNA) molecule in a three-dimensional (3D) matrix, wherein said RNA molecule comprises a nucleic acid sequence;
   (b) hybridizing a primer to said RNA molecule, which primer does not include a functional moiety for immobilization to said 3D matrix;
   (c) using a reverse transcriptase to reverse transcribe said RNA molecule by extending said primer to generate a complementary deoxyribonucleic acid (cDNA) molecule hybridized to said RNA molecule, which cDNA molecule comprises a functional moiety that immobilizes said cDNA molecule to said 3D matrix;
   (d) contacting said cDNA molecule with a probe, which probe comprises an additional functional moiety; and
   (e) covalently or ionically coupling said additional functional moiety to said 3D matrix.

27. The method of claim 26, further comprising degrading said RNA molecule hybridized to said cDNA molecule, to provide said cDNA molecule immobilized to said 3D matrix through said functional moiety.

28. The method of claim 26, wherein said probe comprises a sequence region that is not hybridizable with said cDNA molecule.

29. The method of claim 28, wherein said probe hybridizes to a tethering oligonucleotide comprising said additional functional moiety.

* * * * *